United States Patent
Jones et al.

(10) Patent No.: US 10,588,608 B2
(45) Date of Patent: Mar. 17, 2020

(54) SAMPLING SYSTEMS AND RELATED MATERIALS AND METHODS

(71) Applicant: Progenity Inc., San Diego, CA (US)

(72) Inventors: Mitchell Lawrence Jones, La Jolla, CA (US); Christopher Loren Wahl, La Jolla, CA (US); Aaron Olafur Laurence Philippsen, Victoria (CA); Nicholas David Allan, Victoria (CA); Mark Sasha Drlik, Victoria BC (CA); Ryan Paul McGuinness, Mill Valley, CA (US); Sharat Singh, Rancho Santa Fe, CA (US); Robert S. Magyar, Victoria (CA)

(73) Assignee: Progenity, Inc., San Diego, CA (US)

( * ) Notice: Subject to any disclaimer, the term of this patent is extended or adjusted under 35 U.S.C. 154(b) by 171 days.

(21) Appl. No.: 15/680,430

(22) Filed: Aug. 18, 2017

(65) Prior Publication Data
US 2018/0052084 A1    Feb. 22, 2018

Related U.S. Application Data

(60) Provisional application No. 62/545,129, filed on Aug. 14, 2017, provisional application No. 62/376,688, filed on Aug. 18, 2016.

(51) Int. Cl.
*A61B 5/00* (2006.01)
*A61B 10/00* (2006.01)
(Continued)

(52) U.S. Cl.
CPC ............ *A61B 10/0045* (2013.01); *B01L 3/50* (2013.01); *B01L 3/5023* (2013.01); *B01L 3/5085* (2013.01); *G01N 1/405* (2013.01); *G01N 33/56916* (2013.01); *G01N 33/56938* (2013.01); *G01N 33/56944* (2013.01); *A61B 5/0071* (2013.01); *A61B 5/14539* (2013.01); *A61B 5/42* (2013.01);
(Continued)

(58) Field of Classification Search
CPC .... A61K 2300/00; A61K 45/06; A61K 38/14; A61K 9/0053; A01N 25/28; A61B 1/041; A61B 5/682; A61B 10/04; A61B 1/273; A61B 2562/162; A61B 5/0031; A61B 5/01; A61B 5/073; A61B 5/4238; A61B 5/4255; A61B 5/6861; A61B 5/6873
USPC .......... 600/300, 424, 573, 583; 435/7.9, 6.14
See application file for complete search history.

(56) References Cited

U.S. PATENT DOCUMENTS 6,576,429 B1    6/2003   Hallgren
7,056,673 B2    6/2006   Kamme et al.
(Continued)

FOREIGN PATENT DOCUMENTS

EP          1530950          5/2005
WO    WO 2016/049602    3/2016
WO    WO 2018/050647    3/2018

OTHER PUBLICATIONS

Invitation to Pay Additional Fees for International Application No. PCT/US2017/047481, dated Nov. 24, 2017, 14 pages.
(Continued)

*Primary Examiner* — May A Abouelela
(74) *Attorney, Agent, or Firm* — Fish & Richardson P.C.

(57) ABSTRACT

Sampling systems that include an absorbent material a preservative, such as an analyte preservative, as well as related materials and methods, are disclosed.

33 Claims, 52 Drawing Sheets

(51) Int. Cl.
*B01L 3/00* (2006.01)
*G01N 1/40* (2006.01)
*G01N 33/569* (2006.01)
*A61B 5/145* (2006.01)
*A61B 10/02* (2006.01)

(52) U.S. Cl.
CPC ........... *A61B 10/0038* (2013.01); *A61B 10/02* (2013.01); *A61B 2010/0061* (2013.01); *A61B 2562/162* (2013.01); *B01L 2200/0621* (2013.01); *B01L 2200/0689* (2013.01); *B01L 2200/141* (2013.01); *B01L 2300/042* (2013.01); *B01L 2300/069* (2013.01); *B01L 2300/0636* (2013.01); *B01L 2300/087* (2013.01); *B01L 2300/088* (2013.01); *B01L 2300/0832* (2013.01); *B01L 2300/0877* (2013.01); *B01L 2300/12* (2013.01); *B01L 2300/1883* (2013.01); *B01L 2400/0472* (2013.01); *B01L 2400/0475* (2013.01); *B01L 2400/0633* (2013.01); *B01L 2400/0677* (2013.01)

(56) References Cited

U.S. PATENT DOCUMENTS

| | | | |
|---|---|---|---|
| 7,611,480 B2* | 11/2009 | Levy | A61K 9/0053 422/404 |
| 8,185,185 B2* | 5/2012 | Gilreath | A61B 1/0005 600/407 |
| 8,394,034 B2* | 3/2013 | Iddan | A61B 1/041 600/101 |
| 8,626,268 B2* | 1/2014 | Adler | A61B 1/00009 600/424 |
| 9,131,842 B2* | 9/2015 | Old | A61B 5/0002 |
| 2003/0139661 A1* | 7/2003 | Kimchy | A61B 1/041 600/407 |
| 2004/0254455 A1* | 12/2004 | Iddan | A61B 1/00144 600/424 |
| 2006/0178557 A1* | 8/2006 | Mintchev | A61B 1/041 600/104 |
| 2007/0092401 A1 | 4/2007 | Liao et al. | |
| 2007/0161928 A1* | 7/2007 | Sprenkels | A61B 10/0045 600/575 |
| 2007/0293736 A1* | 12/2007 | Casset | A61N 1/36585 600/300 |
| 2008/0051633 A1 | 2/2008 | Blijevsky | |
| 2008/0194912 A1 | 8/2008 | Trovato | |
| 2008/0208077 A1 | 8/2008 | Iddan et al. | |
| 2008/0294023 A1 | 11/2008 | Rabinovitz et al. | |
| 2009/0131784 A1* | 5/2009 | Betesh | A61B 1/00016 600/424 |
| 2010/0111763 A1 | 5/2010 | Kahn et al. | |
| 2010/0285475 A1* | 11/2010 | Palanisamy | C07K 14/47 435/6.11 |
| 2011/0046458 A1* | 2/2011 | Pinedo | A61B 5/07 600/309 |
| 2011/0125007 A1* | 5/2011 | Steinberg | A61B 1/00158 600/424 |
| 2011/0306055 A1* | 12/2011 | Haince | C12Q 1/34 435/6.14 |
| 2012/0258473 A1 | 10/2012 | Moriya et al. | |
| 2013/0018279 A1 | 1/2013 | Plante et al. | |
| 2013/0022983 A1* | 1/2013 | Grifantini | G01N 33/57419 435/6.12 |
| 2013/0085414 A1* | 4/2013 | Yamatani | A61B 10/0045 600/573 |
| 2014/0113313 A1* | 4/2014 | Moreau | C12Q 1/527 435/7.9 |
| 2014/0206956 A1* | 7/2014 | Rabinovitz | G01N 33/54386 600/302 |
| 2014/0343451 A1* | 11/2014 | Pannell | G01N 33/68 600/562 |
| 2015/0011874 A1 | 1/2015 | Amoako-Tuffour et al. | |
| 2016/0033373 A1 | 2/2016 | Hill et al. | |
| 2016/0038086 A1* | 2/2016 | Wrigglesworth | A61B 5/6861 600/361 |
| 2016/0066855 A1* | 3/2016 | Hyde | A61B 5/6879 600/302 |
| 2016/0213234 A1 | 7/2016 | Poon | |
| 2017/0006202 A1 | 1/2017 | Otani | |
| 2018/0049725 A1 | 2/2018 | Jones et al. | |
| 2018/0160950 A1 | 6/2018 | Rabinovitz et al. | |

OTHER PUBLICATIONS

International Search Report Written Opinion. International Application No. PCT/US2017/047476, dated Jan. 22, 2018, 20 pages.
International Search Report Written Opinion. International Application No. PCT/US2017/047481, dated Jan. 17, 2018, 18 pages.
Invitation to Pay Additional Fees and Where Applicable Protest Fee International Application No. PCT/US2012/047476, dated Nov. 13, 2017, 13 pages.
Dingle et al., "Stable and Noncompetitive RNA Internal Control for Routine Clinical Diagnostic Reverse Transcription-PCR", Journal of Clinical Microbiology, vol. 42(3): 1003-1011, Mar. 2004.
Kane et al., "Fecal Lactoferrin is a Sensitive and Specific Marker in Identifying Intestinal Inflammation", The American Journal of Gastroenterology, 98(6): 1309-1314, 2003.
Kostic et al., "The Gut Microbiome and Disease", Gastroenterology, vol. 146(6): 1489-1499, 2014.
Lehmann et al., "The role and utility of faecal markers in inflammatory bowel disease", Therapeutic Advances in Gastroenterology, vol. 8(1): 23-26, 2015.
Sanschagrin and Yergeau, Next-generation Sequencing of 16S Ribosomal RNA Gene Amplicons, Journal of Visualized Experiments, Issue 90: 51709, Aug. 2014.
Sartor and Mazmanian, "Intestinal Microbes in Inflammatory Bowel Diseases", The American Journal of Gastroenterology Supplements, vol. 1, 12-21, 2012.
Wright et al., "Recent Advances in Characterizing the Gastrointestinal Microbiome in Crohn's Disease: A Systematic Review", Inflammatory Bowel Disease Journal, vol. 21(6): 1219-1228, 2015.
Non-Final Office Action in U.S. Appl. No. 15/680,430, dated Jul. 30, 2019, 21 pages.
Non-Final Office Action in U.S. Appl. No. 15/680,400 dated Oct. 1, 2019, 17 pages.

* cited by examiner

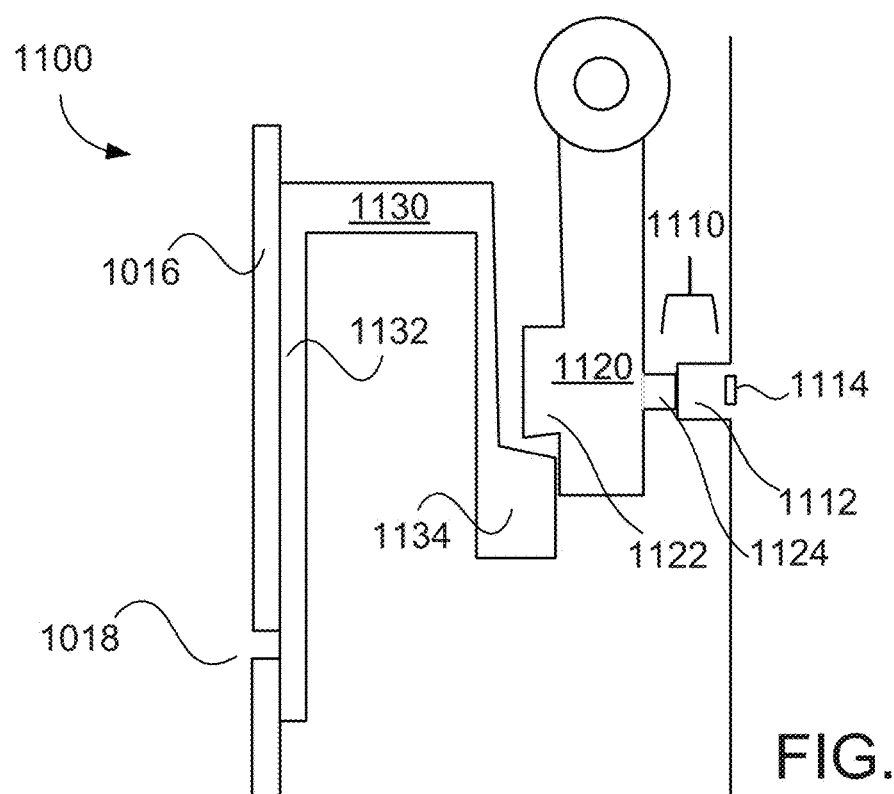
FIG. 12
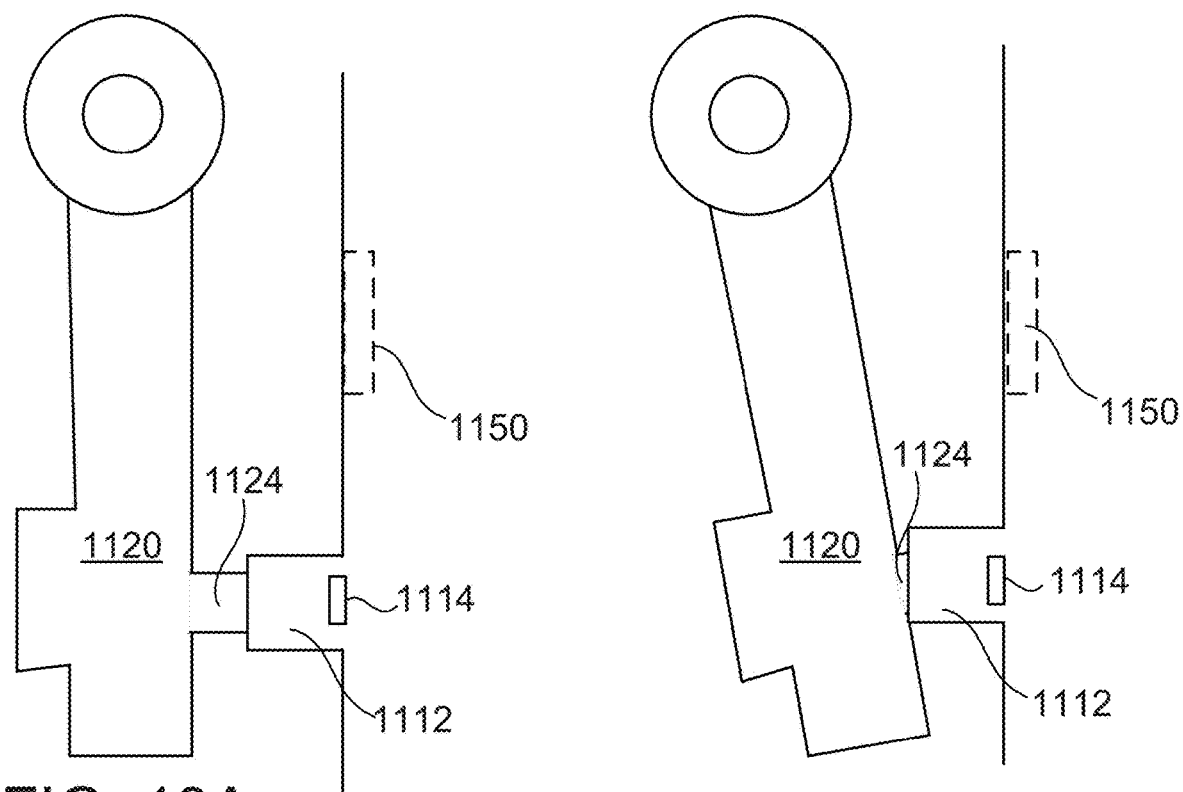
FIG. 13A
FIG. 13B

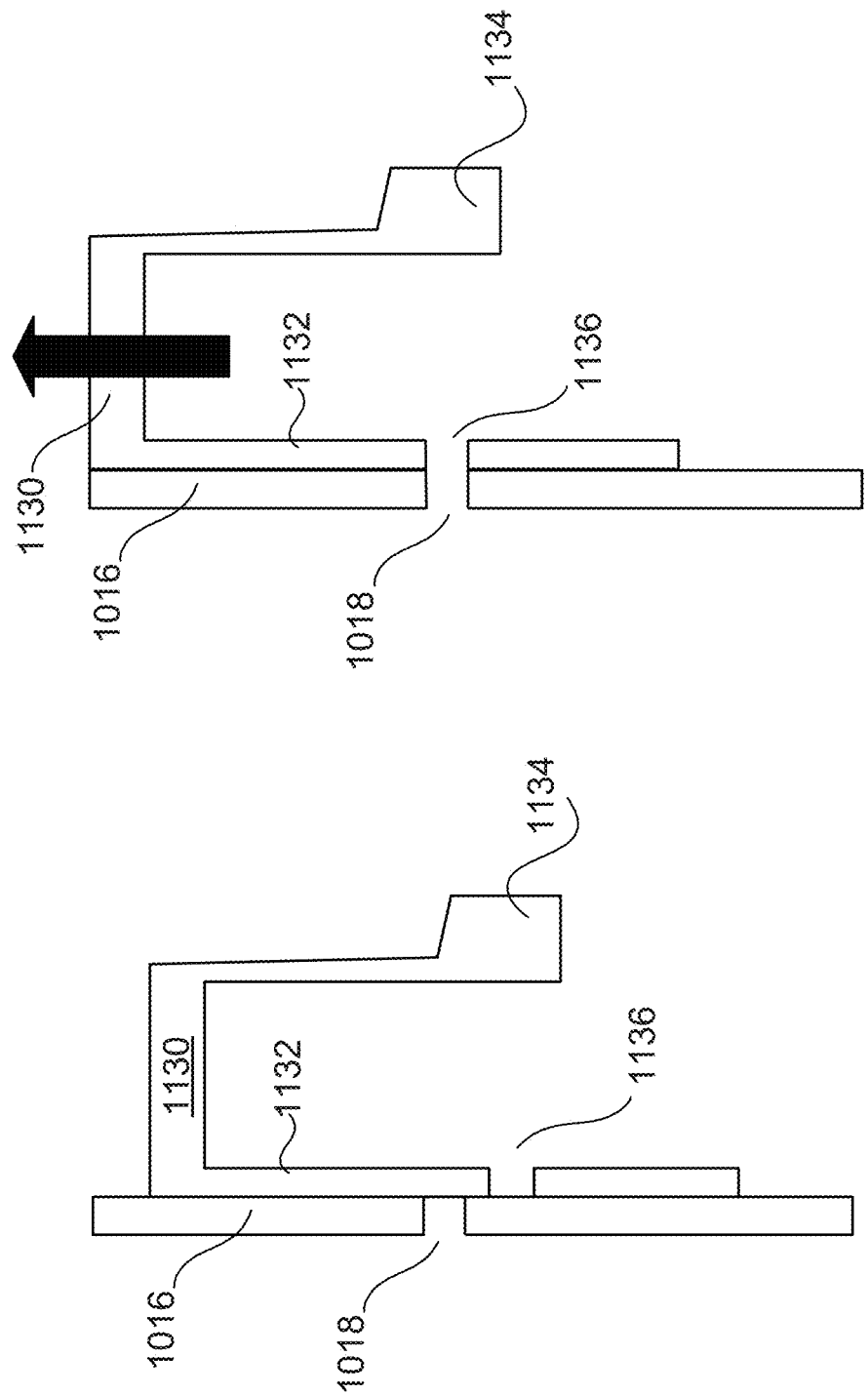

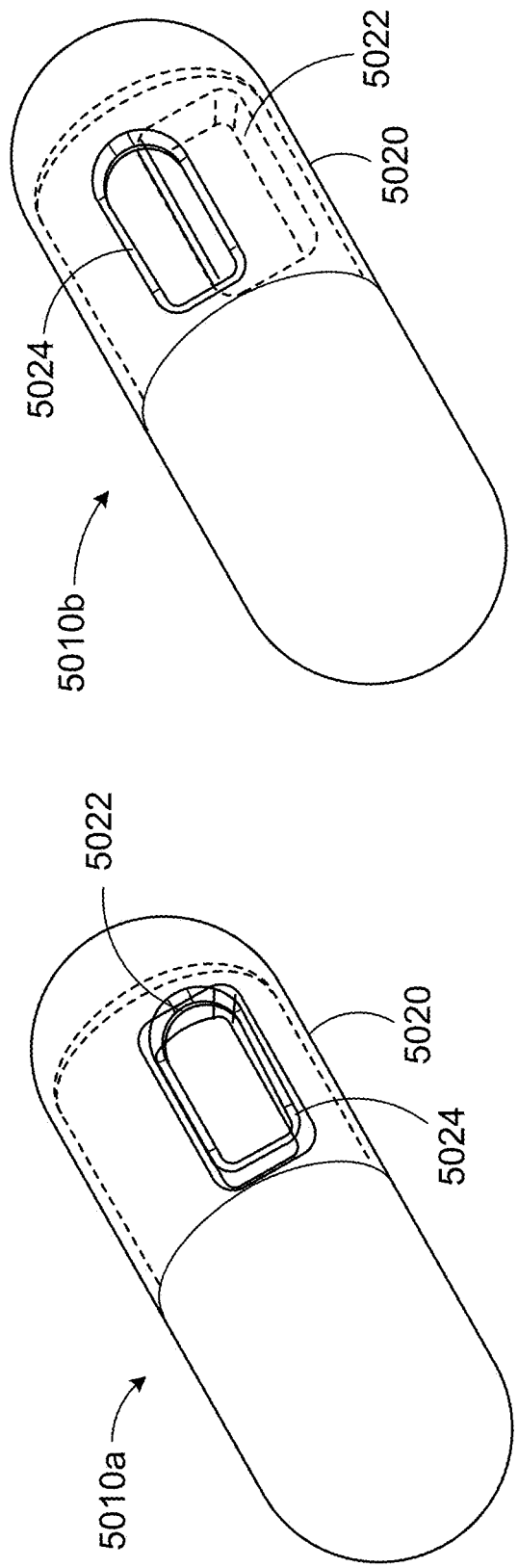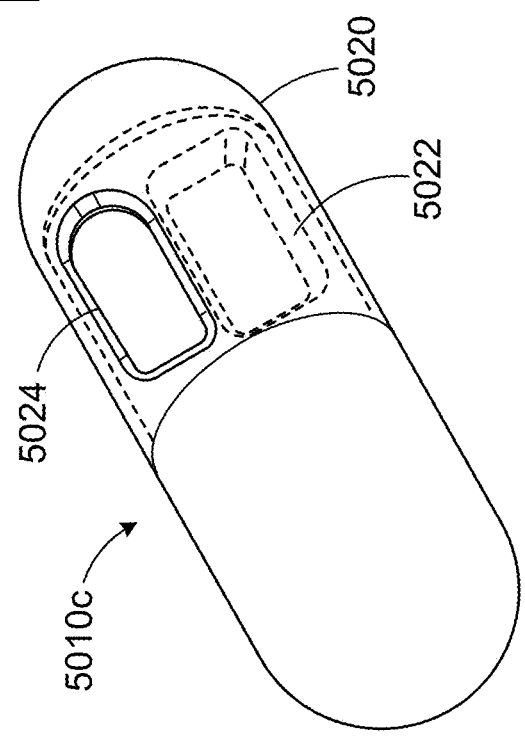
FIG. 33A
FIG. 33B
FIG. 33C

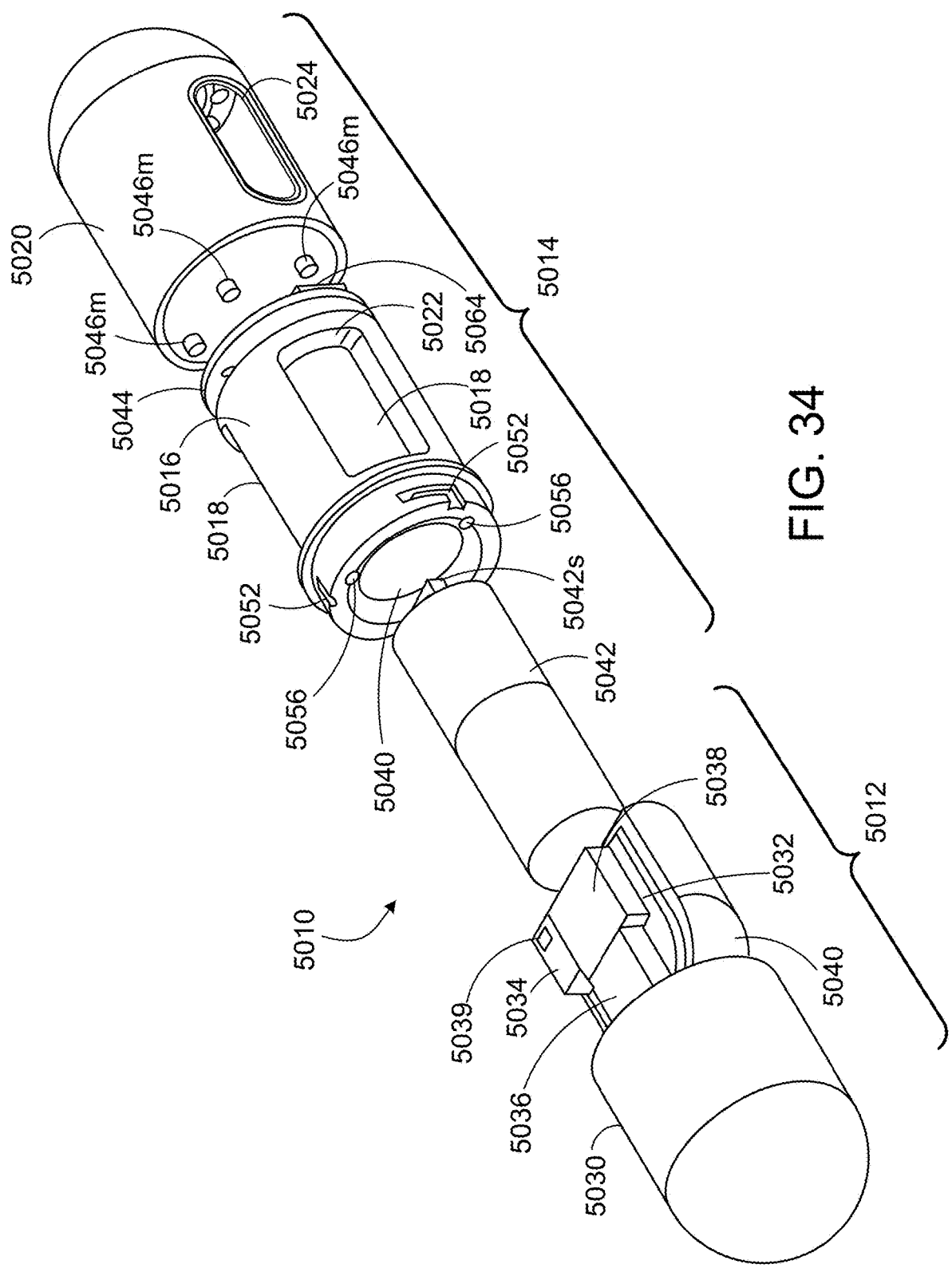

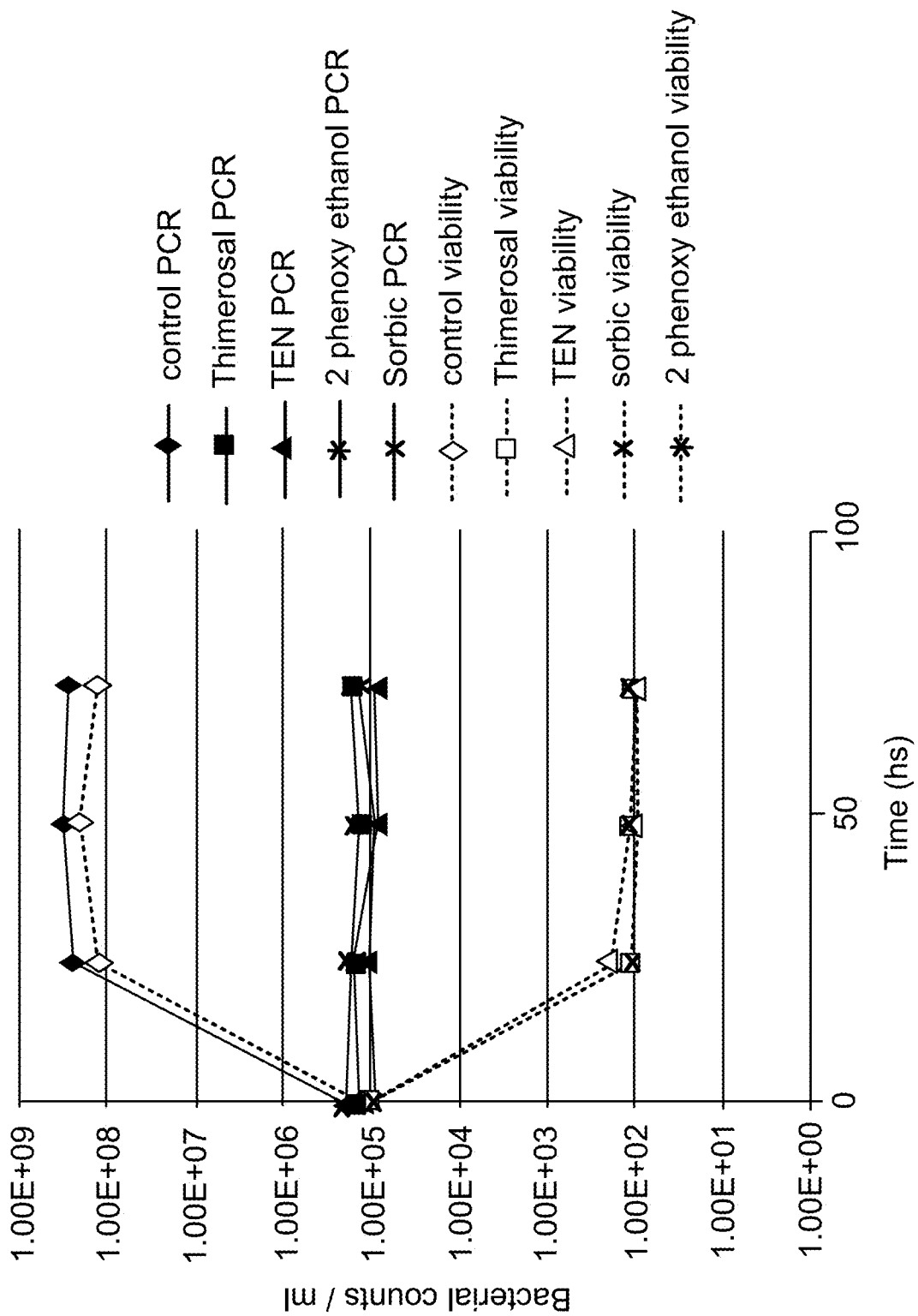

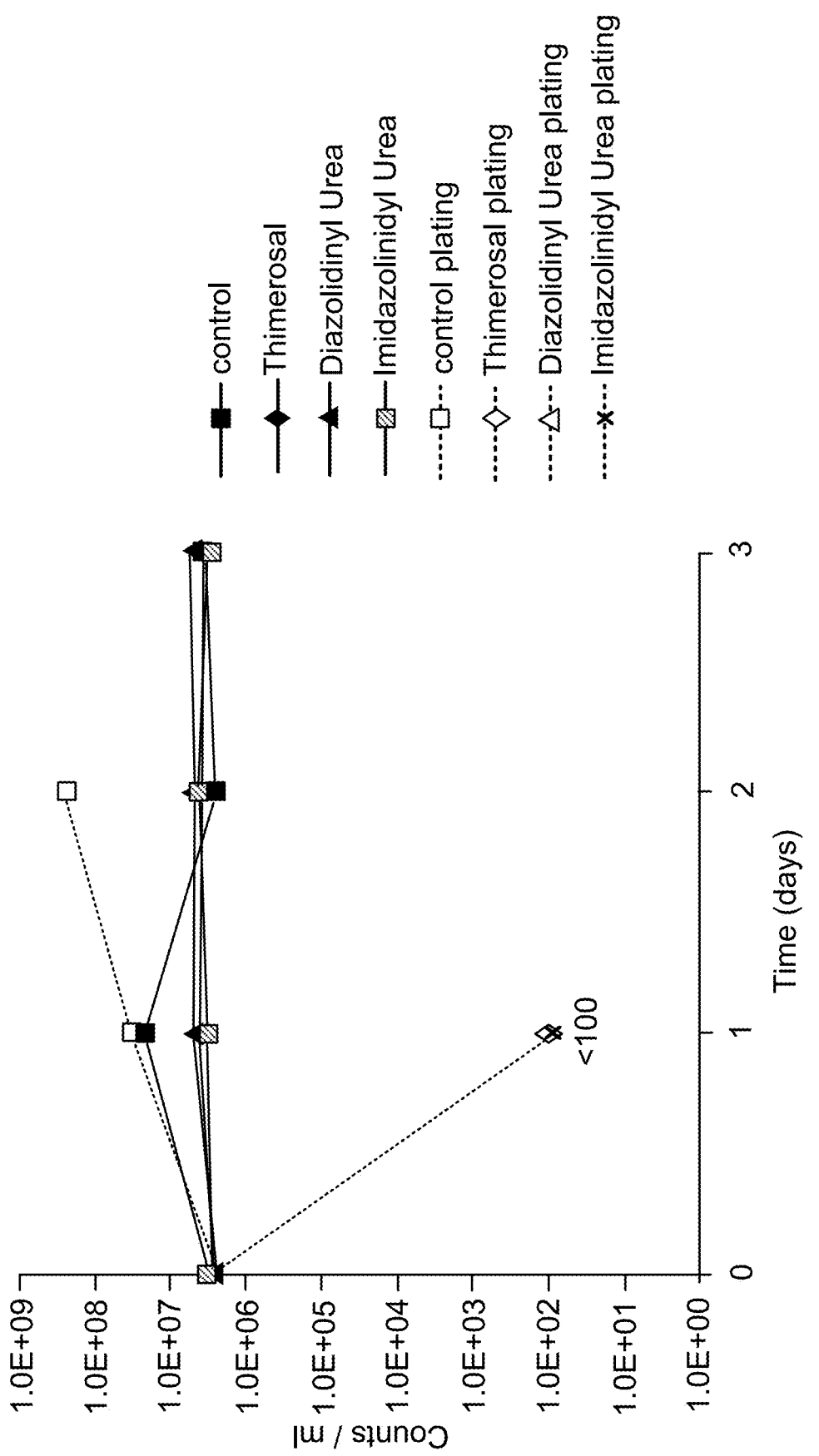

SAMPLING SYSTEMS AND RELATED MATERIALS AND METHODS

CROSS-REFERENCE TO RELATED APPLICATIONS

This application claims priority under 35 U.S.C. § 119 to U.S. Provisional Application No. 62/376,688 filed on Aug. 18, 2016 and U.S. Provisional Application No. 62/545,129 filed on Aug. 14, 2017.

INCORPORATION BY REFERENCE

This application incorporates by reference the following patent applications: U.S. Ser. Nos. 14/460,893; 15/514,413; 62/376,688; 62/385,344; 62/385,553; 62/478,955; 62/434,188; 62/434,320; 62/431,297; 62/434,797; 62/480,187; 62/502,383; 62/540,873; and 62/545,129.

FIELD

The disclosure also relates to sampling systems that include an absorbent material a preservative, such as an analyte preservative.

BACKGROUND

The gastrointestinal (GI) tract generally contains a wealth of information regarding an individual's body. For example, contents in the GI tract may provide information regarding the individual's metabolism. An analysis of the contents of the GI tract may also provide information for identifying relationships between the GI content composition (e.g., relationship between bacterial and biochemical contents) and certain diseases and disorders.

SUMMARY

In one general aspect, the disclosure provides ingestible devices that can obtain a sample when in the GI tract of a subject. The devices are designed to provide a high degree of control over when and where a sample is taken. The devices can be designed to allow analysis/assaying of the sample while the device is still present in the subject, and/or can be designed for the sample to be analyzed/assayed after the device exits the subject. The devices allow for careful control over the amount of sample that is taken in by the device. The disclosure also provides related systems and methods.

In another general aspect, the disclosure relates to sampling systems that include an absorbent material and a preservative, such as an analyte preservative. The sampling systems can be configured to fit within an ingestible device. For example, a sampling system can be an integral portion of an ingestible device. The disclosure also provides related systems and methods.

In one general aspect, the disclosure provides an ingestible device having an opening between an interior of the ingestible device and an exterior of the ingestible device. The ingestible device includes a chamber, and a multi-stage valve system in the interior of the ingestible device. The multi-stage valve system has first, second and third states. The first state of the multi-stage valve system is different from the second and third states of the multi-stage valve system. The second state of the multi-stage valve system is different from the first and third states of the multi-stage valve system. When the multi-stage valve system is in its first state, the opening prevents fluid communication between the interior of the ingestible device and the exterior of the ingestible device. When the multi-stage valve system is in its second state, the opening allows fluid communication between the interior of the ingestible device and the exterior of the ingestible device. When the multi-stage valve system is in its third state, the opening prevents fluid communication between the interior of the ingestible device and the exterior of the ingestible device.

In some embodiments, the multi-stage valve system includes an actuator system having first, second and third states. When the actuator system is in its first state, the multi-stage valve system is in its first state. When the actuator system is in its second state, the multi-stage valve system is in its second state. When the actuator system is in its third state, the multi-stage valve system is in its third state.

In some embodiments, the actuator system includes first and second members.

In some embodiments, when the multi-stage valve system is in its first stage, the first member holds the multi-stage system in its first state, and, when the multi-stage system is in its second stage, the second member holds the valve multi-stage system in its second state.

In some embodiments, the first member includes a first chamber including wax, and the second member includes a second chamber including wax.

In some embodiments, when the actuator system is in its first state, the wax in the first chamber is solid, and, when the actuator system is configured so that, when the actuator is changing from its first state to its second stage in its second state, at least a portion of the wax in the first chamber is liquid.

In some embodiments, the ingestible further includes a device configured to heat the wax in the first chamber.

In some embodiments, when the actuator system is in its second state, the wax in the second chamber is solid, and, when the actuator system is configured so that, when the actuator is changing from its second state to its second stage in its third state, at least a portion of the wax in the second chamber is liquid.

In some embodiments, the ingestible device further includes a device configured to heat the wax in the second chamber.

In some embodiments, the multi-stage valve system further includes a trigger mechanically coupled with the actuator system.

In some embodiments, the trigger has first, second and third states. When the actuator system is in its first state, the trigger is in its first state. When the actuator system is in its second state, the trigger is in its second state. When the actuator system is in its third state, the trigger is in its third state.

In some embodiments, the valve system further includes a gate mechanically coupled to the actuator system.

In some embodiments, the gate has first, second and third states. When the actuator system is in its first state, the gate is in its first state. When the actuator system is in its second state, the gate is in its second state. When the actuator system is in its third state, the gate is in its third state.

In some embodiments, the gate has an opening. When the gate is in its first state, the opening of gate and the opening of the ingestible device are not aligned. When the gate is in its second state, the opening of gate and the opening of the ingestible device are aligned. When the gate is in its third state, the opening of gate and the opening of the ingestible device are not aligned.

In some embodiments, the multi-stage valve system further includes a biasing system mechanically coupled to actuator system.

In some embodiments, the biasing system includes first and second biasing members.

In some embodiments, the first member includes a first spring, and the second member includes a second spring.

In some embodiments, the ingestible device further includes a sampling system configured so that, when the valve system is in its second stage, the exterior of the ingestible device is in fluid communication with the sampling system.

In some embodiments, the sampling system includes a plurality of absorbent members.

In some embodiments, the sampling system includes a biomarker preservative.

In some embodiments, the ingestible device further includes an analytical system configured to analyze a sample in the interior of the ingestible device.

In some embodiments, the ingestible device further includes a microprocessor configured to control at least one system of the ingestible device.

In one general aspect, the disclosure provides an ingestible device having an opening between an interior of the ingestible device and an exterior of the ingestible device. The ingestible device includes a chamber, and a multi-stage valve system in the interior of the ingestible device. The multi-stage valve system includes: an actuator system including a first member; a trigger including a first peg and a first lip; a gate including a protrusion, and a gate leg having an opening; and a biasing system including first and second biasing members. When the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, when the multi-stage valve system is in a second stage different from the first stage: the first lip does not contact the protrusion; and the opening in the gate leg is aligned with the opening in the ingestible device.

In some embodiments, a position of the trigger is different when the multi-stage valve system is in its second stage compared to when the multi-stage valve system is in its first stage.

In some embodiments, a position of the gate is different when the multi-stage valve system is in its second stage compared to when the multi-stage valve system is in its first stage.

In some embodiments the actuator system includes a second member, and the trigger includes a second peg and a second lip. When the multi-stage valve system is in a second stage different from the first stage: the first biasing member applies a force to the trigger so that the second peg contacts the second member; the second member opposes the force applied to the trigger by the first biasing member; the second biasing member applies a force to the gate so that the protrusion contacts the second lip; the second lip opposes the force applied to the gate by the second biasing member; and the opening in the gate leg is aligned with the opening in the ingestible device.

In some embodiments, when the multi-stage valve system is in a third stage different from the first and second stages: the second lip does not contact the protrusion; and the opening in the gate leg is not aligned with the opening in the ingestible device.

In some embodiments, a position of the trigger is different when the multi-stage valve system is in its third stage compared to when the multi-stage valve system is in its first stage and its second stage.

In some embodiments, a position of the gate is different when the multi-stage valve system is in its third stage compared to when the multi-stage valve system is in its second stage.

In some embodiments, the ingestible device further includes a sampling system configured so that, when the valve system is in its second stage, the exterior of the ingestible device is in fluid communication with the sampling system.

In some embodiments, the sampling system includes a plurality of absorbent members.

In some embodiments, the sampling system includes a biomarker preservative.

In some embodiments, the ingestible device further includes an analytical system configured to analyze a sample in the interior of the ingestible device.

In some embodiments, the ingestible device further includes a microprocessor configured to control at least one system of the ingestible device.

In one general aspect, the disclosure provides an ingestible device having an opening between an interior of the ingestible device and an exterior of the ingestible device. The ingestible device includes a chamber, and a sampling system in the interior of the ingestible device. The sampling system includes a first absorbent member, and a second absorbent member different from the first absorbent member. The sampling system is configured so that fluid that flows from the exterior of the ingestible device to the interior of the ingestible device enters the first absorbent member. The sampling system is configured to allow fluid to flow from the first absorbent member to the second absorbent member.

In some embodiments, the second absorbent member has a first end and a second end opposite the first end. The sampling system is configured to allow fluid to flow from the first absorbent member to the first end of the second absorbent member.

In some embodiments, the ingestible device further includes a third absorbent member different from the first and second absorbent members.

In some embodiments, the sampling system is configured to allow fluid to flow from the second absorbent member to the third absorbent member.

In some embodiments, the sampling system is configured to: prevent fluid from flowing directly from the first end of the second member to the third member; and allow fluid to flow from second end of the second absorbent member to the third absorbent member.

In some embodiments, the ingestible device further includes a blocking member between the second and third absorbent members, wherein the blocking member is configured to prevent the flow of fluid from the second absorbent to the third absorbent member.

In some embodiments, the sampling system further includes a fourth absorbent member different from the first, second and third absorbent members, and the sampling system is configured to allow fluid to flow from the second absorbent member to the fourth absorbent member.

In some embodiments, the sampling system further includes a fourth absorbent member different from the first, second and third absorbent members.

In some embodiments, the sampling system includes an analyte preservative.

In some embodiments, the sampling system further includes a cell filter between the first and second absorbent members.

In some embodiments, further includes a multi-stage valve system in the interior of the ingestible device.

In some embodiments, the multi-stage valve system has first, second and third states. The first state of the multi-stage valve system is different from the second and third states of the multi-stage valve system. The second state of the multi-stage valve system is different from the first and third states of the multi-stage valve system. When the multi-stage valve system is in its first state, the opening prevents fluid communication between the interior of the ingestible device and the exterior of the ingestible device. When the multi-stage valve system is in its second state, the opening allows fluid communication between the interior of the ingestible device and the exterior of the ingestible device. When the multi-stage valve system is in its third state, the opening prevents fluid communication between the interior of the ingestible device and the exterior of the ingestible device.

In some embodiments, the multi-stage valve system includes: an actuator system including a first member; a trigger including a first peg and a first lip; a gate including a protrusion, and a gate leg having an opening; and a biasing system including first and second biasing members. When the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device further includes an analytical system configured to analyze a sample in the sampling system.

In some embodiments, the ingestible device further includes a microprocessor configured to control at least one system of the ingestible device.

In one general aspect, the ingestible device has an opening between an interior of the ingestible device and an exterior of the ingestible device. The ingestible device includes: a chamber; and a sampling system in the interior of the ingestible device configured to absorb a fluid that enters the interior of the ingestible device via the opening. The sampling system includes an absorbent member and at least one preservative at least partially absorbed in the absorbent member.

In some embodiments, the preservative is at least one analyte preservative.

In some embodiments, the analyte preservative includes a preservative for at least one of a nucleic acid, a small molecule, or a protein.

In some embodiments, the analyte preservative includes a preservative for at least one nucleic acid, small molecule, or protein that is a biomarker of at least one GI disorder.

In some embodiments, the analyte preservative is a surfactant.

In some embodiments, the analyte preservative is a stabilizer.

In some embodiments, the analyte preservative includes a member selected from the group consisting of a nuclease inhibitor, an RNase inhibitor, and a protease inhibitor.

In some embodiments, the analyte preservative includes an acid having a pKa of from three to seven.

In some embodiments, the analyte preservative includes a paraben.

In some embodiments, the surfactant includes polysorbate.

In some embodiments, the stabilizer includes trehalose or dextran.

In some embodiments, the paraben includes a member selected from the group consisting of parahydroxybenzoate, an ester of parahydroxybenzoic acid, and propyl paraben.

In some embodiments, the analyte preservative includes a protease inhibitor.

In some embodiments, the protease inhibitor includes a member selected from the group consisting of serine protease inhibitors, metalloprotease inhibitors, aminopeptidase inhibitors, cysteine peptidase inhibitor, and aspartyl protease inhibitors.

In some embodiments, the analyte preservative includes an acid.

In some embodiments, the analyte preservative includes at least one member selected from the group consisting of sorbic acid and citric acid.

In some embodiments, the preservative includes at least one bacteria preservative.

In some embodiments, the bacteria preservative reduces bacterial growth and multiplication.

In some embodiments, the bacteria preservative includes a bactericidal or bacteriostatic preservative.

In some embodiments, the bacteria preservative includes a preservative for at least one bacterium associated with at least one GI disorder.

In some embodiments, the bacteria preservative includes a member selected from the group consisting of sorbic acid, citric acid, propyl paraben, nisin, dimethyl dicarbonate, ethylenediaminetetraacetic acid (EDTA), sodium azide, hydroxyurea, fusidic acid, diazolidinyl urea, imidazolidinyl urea, salicylic acid, barium and nickle chloride, metallic copper, thimerosal, 2-phenoxyethanol, and ProClin.

In some embodiments, the bacteria preservative is sorbic acid, thimerosal, 2-phenoxyethanol, diazolinidyl urea, or imidazolinidyl urea.

In some embodiments, the absorbent member includes at least one analyte preservative in addition to the at least one bacteria preservative.

In some embodiments, the analyte preservative is a nucleic acid preservative.

In some embodiments, the nucleic acid preservative is a DNAse inhibitor or an RNase inhibitor.

In some embodiments, the sampling system includes a plurality of different preservatives.

In some embodiments, the sampling system includes: a first absorbent member; and a second absorbent member different from the first absorbent member. The sampling system is configured so that fluid that flows from the exterior of the ingestible device to the interior of the ingestible device enters the first absorbent member. The sampling system is configured to allow fluid to flow from the first absorbent member to the second absorbent member.

In some embodiments, the sampling system further includes a cell filter between the first and second absorbent members.

In some embodiments, the sampling system further includes a cell filter. In some embodiments, the ingestible further includes an analytical system configured to analyze a sample in the sampling system.

In some embodiments, the ingestible further includes a microprocessor configured to control at least one system of the ingestible device.

In some embodiments, the ingestible further includes a multi-stage valve system in the interior of the ingestible device.

In some embodiments: the multi-stage valve system has first, second and third states; the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the multi-stage valve system includes: an actuator system including a first member; a trigger including a first peg and a first lip; a gate including a protrusion, and a gate leg having an opening; and a biasing system including first and second biasing members. When the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device further includes an analytical system configured to analyze a sample in the sampling system.

In one general aspect, the disclosure provides a method, that includes collecting a sample into a sampling system of an ingestible device. The sampling system includes an absorbent member and at least one preservative at least partially absorbed in the absorbent member.

In some embodiments, the ingestible device is an ingestible device is an ingestible device as disclosed herein.

In one general aspect, the disclosure provides a sampling system that includes: an absorbent member; and at least one preservative at least partially absorbed in the absorbent member. The absorbent member is configured to absorb a fluid.

In some embodiments, the preservative is at least one analyte preservative.

In some embodiments, the analyte preservative includes a preservative for at least one of a nucleic acid, a small molecule, or a protein.

In some embodiments, the analyte preservative includes a preservative for at least one nucleic acid, small molecule, or protein that is a biomarker of at least one GI disorder.

In some embodiments, the analyte preservative is a surfactant.

In some embodiments, the analyte preservative is a stabilizer.

In some embodiments, the analyte preservative includes a member selected from the group consisting of a nuclease inhibitor, an RNase inhibitor, and a protease inhibitor.

In some embodiments, the analyte preservative includes an acid having a pKa of from three to seven.

In some embodiments, the analyte preservative includes a paraben.

In some embodiments, the surfactant includes polysorbate.

In some embodiments, the stabilizer includes trehalose or dextran.

In some embodiments, the paraben includes a member selected from the group consisting of parahydroxybenzoate, an ester of parahydroxybenzoic acid, and propyl paraben.

In some embodiments, the analyte preservative includes a protease inhibitor.

In some embodiments, the protease inhibitor includes a member selected from the group consisting of serine protease inhibitors, metalloprotease inhibitors, aminopeptidase inhibitors, cysteine peptidase inhibitor, and aspartyl protease inhibitors.

In some embodiments, the analyte preservative includes an acid.

In some embodiments, the analyte preservative includes at least one member selected from the group consisting of sorbic acid and citric acid.

In some embodiments, the preservative includes at least one bacteria preservative.

In some embodiments, the bacteria preservative reduces bacterial growth and multiplication.

In some embodiments, the bacteria preservative includes a bactericidal or bacteriostatic preservative.

In some embodiments, the bacteria preservative includes a preservative for at least one bacterium associated with at least one GI disorder.

In some embodiments, the bacteria preservative includes a member selected from the group consisting of sorbic acid, citric acid, propyl paraben, nisin, dimethyl dicarbonate, ethylenediaminetetraacetic acid (EDTA), sodium azide, hydroxyurea, fusidic acid, diazolidinyl urea, imidazolidinyl urea, salicylic acid, barium and nickle chloride, metallic copper, thimerosal, 2-phenoxyethanol, and ProClin.

In some embodiments, the bacteria preservative is sorbic acid, thimerosal, 2-phenoxyethanol, diazolidinyl urea, or imidazolinidyl urea.

In some embodiments, the absorbent member includes at least one analyte preservative in addition to the at least one bacteria preservative.

In some embodiments, the analyte preservative is a nucleic acid preservative.

In some embodiments, the nucleic acid preservative is a DNAse inhibitor or an RNase inhibitor.

In some embodiments, the sampling system includes a plurality of different preservatives.

In some embodiments, the sampling system includes: a first absorbent member; and a second absorbent member different from the first absorbent member. The sampling system is configured so that fluid that flows from the exterior of the ingestible device to the interior of the ingestible device enters the first absorbent member. The sampling system is configured to allow fluid to flow from the first absorbent member to the second absorbent member.

In some embodiments, the sampling system further includes a cell filter between the first and second absorbent members.

In some embodiments, the sampling system further includes a cell filter.

In some embodiments, the fluid includes a GI fluid.

In some embodiments, the sampling system is configured to fit within an ingestible device.

In some embodiments, the sampling system is configured to fit within an ingestible device that does not include analytical instrumentation.

In one general aspect, the disclosure provides a method that includes collecting a sample into a sampling system which includes an absorbent member and at least one preservative at least partially absorbed in the absorbent member.

In some embodiments, the sampling system is a sampling system as disclosed herein.

In some aspects, an ingestible device is provided herein. The ingestible device includes a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In at least some embodiments, the sampling chamber is configured to hold a sample obtained from a gastrointestinal (GI) tract of a body.

In at least some embodiments, the ingestible device further comprising a mechanical actuator coupled to at least one moveable valve having at least an open position and a closed position, wherein the at least one moveable valve in the closed position prevents fluid from entering the sampling chamber and prevents the sample from exiting the sampling chamber.

In at least some embodiments, the ingestible device further comprising a microprocessor configured to control the mechanical actuator to move the at least one moveable valve into the open position.

In at least some embodiments, the at least one moveable value comprises: a first moveable valve coupled to the mechanical actuator, wherein the first movable valve in the closed position prevents fluid from entering the sampling chamber via the first opening and prevents the sample from exiting the sampling chamber via the first opening; and a second movable valve coupled to the mechanical actuator, wherein the second moveable valve in the closed position prevents fluid from entering the sampling chamber via the second opening and prevents the sample from exiting the sampling chamber via the second opening.

In at least some embodiments, the first moveable valve in the closed position is contained in a first portion of the curved chamber located between the sampling chamber and the first opening; the second moveable valve in the closed position is contained in a second portion of the curved chamber located between the sampling chamber and the second opening; and the first portion of the curved chamber, the second portion of the curved chamber, and the mechanical actuator are oriented in a substantially straight line, such that the mechanical actuator is configured to simultaneously move the first moveable valve and the second moveable valve.

In at least some embodiments, the first movable valve and the second moveable valve are rotary valves, and the mechanical actuator is configured to simultaneously rotate the first movable valve and the second moveable valve between the closed position and the open position.

In at least some embodiments, the first moveable valve and the second moveable valve are pin valves, the mechanical actuator is configured to simultaneously move the first moveable valve and the second moveable valve linearly, and the mechanical actuator comprises at least one of (1) a linear actuator and (2) a rotary actuator coupled to a lead screw.

In at least some embodiments, the ingestible further comprises an element positioned within the curved chamber proximate to the second opening that restricts fluid from entering the curved chamber via the second opening, the element comprising at least one of a hydrophobic material, an air permeable membrane and a one-way valve.

In at least some embodiments, the ingestible device comprises a sensor within or proximate to the sampling chamber for detecting at least one of (1) a property of the sample, and (2) a result of an assay technique applied to the sample.

In at least some embodiments, the ingestible device comprises at least one sub-chamber connected to the curved chamber, the at least one sub-chamber being configured to hold a sample obtained from a gastrointestinal (GI) tract of a body and isolate the sample from the sampling chamber.

In at least some embodiments, the ingestible device further comprises a plurality of sub-chambers connected to the curved chamber, each of the plurality of sub-chambers being configured to obtain a sample from a gastrointestinal (GI) tract of a body at a different time.

In at least some embodiments, the ingestible device further comprises a plurality of sub-chambers connected to the curved chamber, each of the plurality of sub-chambers being configured to obtain a sample from a gastrointestinal (GI) tract of a body from a different portion of the gastrointestinal (GI) tract.

In some aspects, another ingestible device is provided herein. The ingestible devices includes a housing defined by a first end, a second end substantially opposite from the first end, a wall extending longitudinally from the first end to the second end, and an opening; a sampling chamber within the housing, wherein the sampling chamber contains an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In at least some embodiments, the ingestible device comprises a microprocessor configured to control the heating element to generate heat. In at least some embodiments, the ingestible device comprises a barrier within the sampling chamber positioned between the absorptive material and the inlet port, the barrier covering a surface of the absorptive material.

In at least some embodiments, the barrier separates the absorptive material from a remaining portion of the sampling chamber including the inlet port.

In at least some embodiments, the barrier comprises: a first portion proximal to the inlet port and comprising a flexible membrane, and a second portion adjacent to the first portion and comprising a rigid material.

In at least some embodiments, at least a portion of the absorptive material adjacent to the flexible membrane absorbs at least a portion of the sample and expands, causing the flexible membrane to reseal the inlet port.

In at least some embodiments, a portion of the sampling chamber between the second portion of the barrier and a wall of the sampling chamber forms a testing area, and a sensor within or proximate to the sampling chamber is configured to detect at least one of (1) a property of the sample within the testing area, and (2) a result of an assay technique applied to the sample within the testing area.

In at least some embodiments, the first portion of the barrier and the second portion of the barrier do not allow the sample to pass through the barrier and contact the absorptive material.

In at least some embodiments, the barrier comprises a third portion adjacent to the second portion, the third portion comprising a semi-permeable membrane.

In at least some embodiments, the semi-permeable membrane allows at least a portion of the sample to pass through the semi-permeable membrane and contact the absorptive material.

In at least some embodiments, the semi-permeable membrane is rigid.

In at least some embodiments, the single use sealing device is a breakable membrane.

In at least some embodiments, the single use sealing device is a plug.

In at least some embodiments, the plug comprises a material with a melting point between 38 degrees Celsius and 80 degrees Celsius, the heating element comprises an electrically conductive element warmed by ohmic heating, and the heating element heats the plug to at least the melting point.

In at least some embodiments, the inlet port has a cross-sectional area less than 50 square millimeters.

In at least some embodiments, the ingestible device comprises at least one sub-chamber connected to the sampling chamber, the at least one sub-chamber being configured to hold a second sample obtained from a gastrointestinal (GI) tract of a body and isolate the second sample from the sampling chamber.

In at least some embodiments, the ingestible device comprises a plurality of sub-chambers connected to the sampling chamber, each of the plurality of sub-chambers being configured to obtain a different sample from a gastrointestinal (GI) tract of a body at a different time.

In at least some embodiments, the ingestible device comprises a plurality of sub-chambers connected to the sampling chamber, each of the plurality of sub-chambers being configured to obtain a different sample from a gastrointestinal (GI) tract of a body from a different portion of the gastrointestinal (GI) tract.

In some aspects, another ingestible device is provided herein. The ingestible device includes a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In at least some embodiments, the ingestible device comprises a mechanical actuator coupled to the moveable valve; and a microprocessor configured to control the mechanical actuator to move the moveable valve to the open position.

In at least some embodiments, the moveable valve is a pin valve, the mechanical actuator comprises at least one of (1) a linear actuator and (2) a rotating actuator coupled to a lead screw, and the pin valve moves linearly to switch between the open position and the closed position.

In at least some embodiments, the moveable valve is a rotary valve, the mechanical actuator is configured to rotate the rotary valve, and the rotary valve rotates to switch between the open position and the closed position.

In at least some embodiments, the mechanical actuator comprises at least one of (1) a linear actuator and (2) a rotating actuator coupled to a lead screw, and the moveable valve comprises a flexible diaphragm that moves from the open position to the closed position by using the mechanical actuator to apply pressure across a first surface of the flexible diaphragm.

In at least some embodiments, the ingestible devices comprise a spring mechanism positioned proximate to the flexible diaphragm, wherein the spring mechanism applies a counter-pressure across a second surface of the flexible diaphragm that is opposite the first surface, such that the flexible diaphragm is in the open position when the mechanical actuator does not apply pressure across the first surface.

In at least some embodiments, the exit port comprises a gas permeable membrane to allow the gas to exit the sampling chamber.

In at least some embodiments, the exit port comprises a one-way valve configured to allow gas to exit the sampling chamber and prevent gas from re-entering the sampling chamber.

In at least some embodiments, the exit port is connected to an outlet port on the housing, the outlet port comprising at least one of a gas permeable membrane, a one-way valve, and a hydrophobic channel.

In at least some embodiments, the ingestible device includes a hydrophilic sponge within the sampling chamber that is configured to absorb the sample.

In at least some embodiments, the ingestible device includes a sensor within or proximate to the sampling chamber for detecting at least one of (1) a property of the sample, and (2) a result of an assay technique applied to the sample.

In at least some embodiments, the exit port is connected to a volume within the ingestible device, the volume being located outside of the sampling chamber and containing gas.

In at least some embodiments, the exit port is connected to a sealed vacuum chamber with an internal pressure lower than the pressure contained within at least one of the inlet region and the sampling chamber, the sealed vacuum chamber capable of being unsealed, thereby reducing the pressure in the sampling chamber and drawing the sample into the sampling chamber.

In at least some embodiments, moving the moveable valve from the closed position to the open position causes a volume of the inlet region to increase.

In at least some embodiments, moving the moveable valve from the open position to the closed position causes a volume of the inlet region to decrease.

In at least some embodiments, the ingestible device comprises at least one sub-chamber connected to the inlet region, the at least one sub-chamber being configured to hold a second sample obtained from a gastrointestinal (GI) tract of a body and isolate the second sample from the sampling chamber.

In at least some embodiments, the ingestible device comprises a plurality of sub-chambers connected to the inlet region, each of the plurality of sub-chambers being configured to obtain a different sample from a gastrointestinal (GI) tract of a body at a different time.

In at least some embodiments, the ingestible device comprises a plurality of sub-chambers connected to the inlet region, each of the plurality of sub-chambers being configured to obtain a different sample from a gastrointestinal (GI) tract of a body from a different portion of the gastrointestinal (GI) tract.

In some aspects, another ingestible device is provided herein. The ingestible device includes a housing defined by a first end, a second end substantially opposite from the first end, a wall extending longitudinally from the first end to the second end, and an opening; a sampling chamber within the housing having an entry port; an inlet region connecting the opening in the housing to the entry port of the sampling chamber; and a moveable pump comprising a first portion that is shaped to fit within the opening and a second portion that is shaped to fit within the inlet region; and a mechanical actuator configured to move the moveable pump to an open position and a fully closed position, wherein: the moveable pump in the open position positions the first portion of the moveable pump at a distance away from the opening, allowing a sample to enter the inlet region via the opening; and the moveable pump in the fully closed position positions the first portion of the moveable pump within the opening and positions the second portion of the moveable pump adjacent to the entry port, preventing the sample from exiting the inlet region via the opening and the entry port.

In at least some embodiments, the mechanical actuator is further configured to move the moveable pump to a partially closed position, wherein the moveable pump in the partially closed position positions a surface of the first portion of the moveable pump adjacent to the opening, thereby sealing off the opening such that the sample is prevented from exiting the inlet region via the opening.

In at least some embodiments, the partially closed position positions the second portion to be away from the entry port, thereby unsealing the entry port such that the sample is allowed to exit the inlet region via the entry port.

In at least some embodiments, the ingestible device comprises a microprocessor configured to control the mechanical actuator to move the moveable pump between the fully closed position and the open position.

In at least some embodiments, the mechanical actuator comprises at least one of (1) a linear actuator and (2) a rotating actuator coupled to a lead screw, and the mechanical actuator is usable to move the moveable pump linearly between the fully closed position and the open position.

In at least some embodiments, the ingestible device comprises an exit port on an opposite end of the sampling chamber from the entry port, wherein the exit port is configured to allow gas to exit the chamber and prevent at least a portion of a sample from exiting the chamber.

In at least some embodiments, the exit port comprises a gas permeable membrane to allow the gas to exit the sampling chamber.

In at least some embodiments, the exit port comprises a one-way valve configured to allow gas to exit the sampling chamber and prevent gas from re-entering the sampling chamber.

In at least some embodiments, the exit port is connected to an outlet port on the housing, the outlet port comprising at least one of a gas permeable membrane, a one-way valve, and a hydrophobic channel.

In at least some embodiments, the exit port is connected to a volume within the ingestible device, the volume being located outside of the sampling chamber and containing gas.

In at least some embodiments, the ingestible device comprises a hydrophilic sponge within the sampling chamber that is configured to absorb the sample.

In at least some embodiments, the ingestible device comprises a sensor within or proximate to the sampling chamber for detecting at least one of (1) a property of the sample, and (2) a result of an assay technique applied to the sample.

In at least some embodiments, the ingestible device comprises at least one sub-chamber connected to the inlet region, the at least one sub-chamber being configured to hold a second sample obtained from a gastrointestinal (GI) tract of a body and isolate the second sample from the sampling chamber.

In at least some embodiments, the ingestible device comprises a plurality of sub-chambers connected to the inlet region, each of the plurality of sub-chambers being configured to obtain a different sample from a gastrointestinal (GI) tract of a body at a different time.

In at least some embodiments, the ingestible device comprises a plurality of sub-chambers connected to the inlet region, each of the plurality of sub-chambers being configured to obtain a different sample from a gastrointestinal (GI) tract of a body from a different portion of the gastrointestinal (GI) tract.

BRIEF DESCRIPTION OF THE DRAWINGS

FIG. 12 illustrates a valve system.

FIGS. 13A and 13B illustrate a portion of a two-stage valve system in its first and second stages, respectively.

FIGS. 15A and 15B illustrate a portion of a two-stage valve system in its first and second stages, respectively.

FIGS. 33A-33C show illustrate operation of ingestible device 5010.

FIG. 34 illustrates an exploded view of the components of ingestible device.

DETAILED DESCRIPTION

To provide an overall understanding of the disclosure, certain illustrative embodiments will now be described, including various systems and methods for obtaining samples using ingestible devices. In particular, techniques are described that allow an ingestible device to obtain a sample from within a gastrointestinal (GI) tract. These samples may include any of the fluids, solids, particulates, or other substances found within the GI tract. However, it will be understood by one of ordinary skill in the art that the systems and methods described herein may be adapted and modified as is appropriate for the applications being addressed, and that the systems and methods described herein may be employed in other suitable applications, and that such other additions and modifications will not depart from the scope of the present disclosure. Generally, the ingestible devices described herein may comprise actuators, sensors, valves, chambers, logic devices, telemetry systems, microcontrollers or other devices and processors that may be configured using a combination of hardware, firmware, and software to carry out one or more of the methods described herein.

Figure 1:
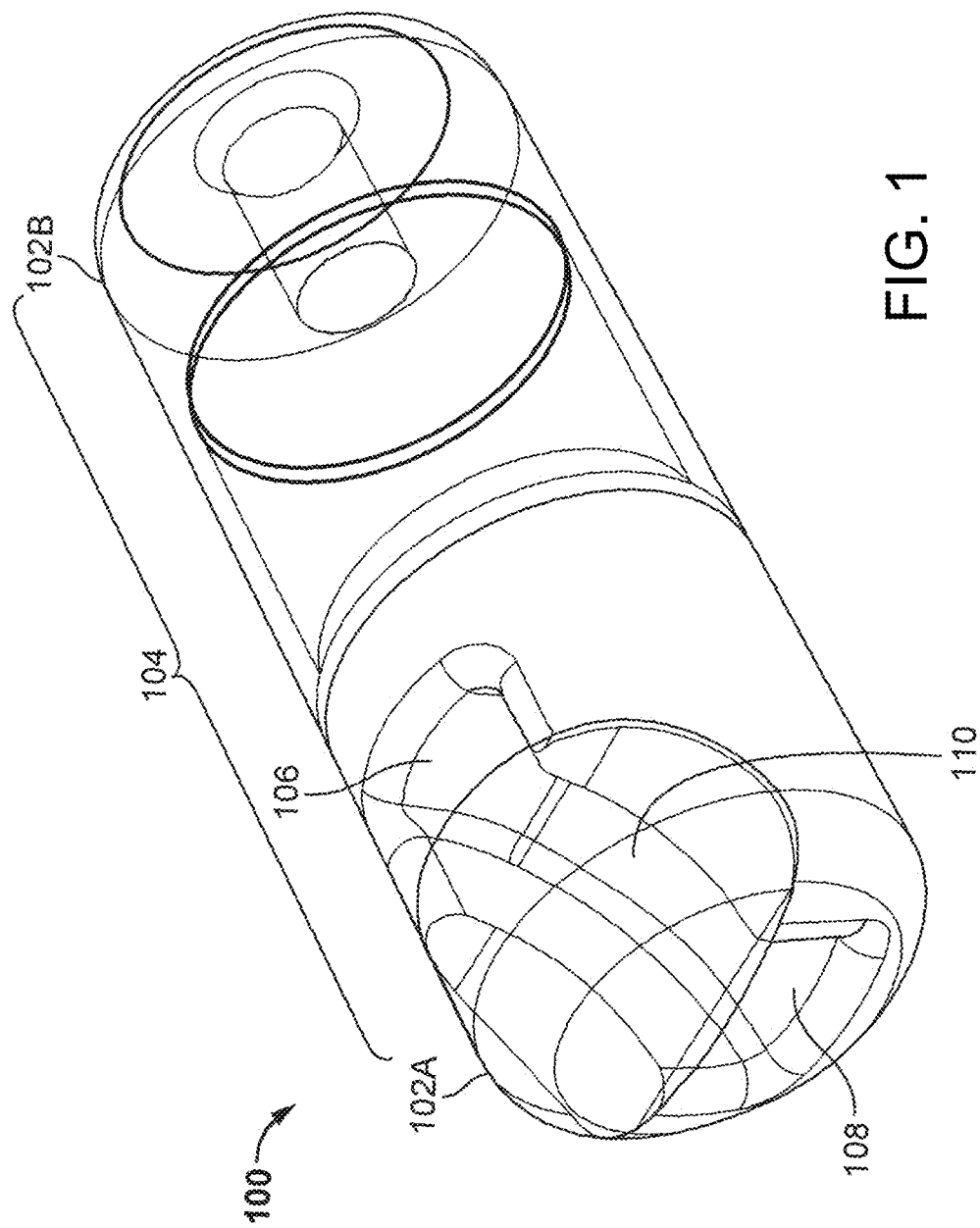
FIG. 1 shows an illustrative embodiment of an ingestible device with multiple openings in the housing.

FIG. 1 illustrates an example ingestible device 100 with multiple openings in the housing. The ingestible device 100 has an outer housing with a first end 102A, a second end 102B, and a wall 104 extending longitudinally from the first end 102A to the second end 102B. Ingestible device 100 has a first opening 106 in the housing, which is connected to a second opening 108 in the housing. The first opening 106 of the ingestible device 100 is oriented substantially perpendicular to the second opening 108, and the connection between the first opening 106 and the second opening 108 forms a curved chamber 110 within the ingestible device 100.

The overall shape of the ingestible device 100, or any of the other ingestible devices discussed in this disclosure, may be similar to an elongated pill or capsule. This may make the ingestible device 100 easy to consume, and allow it to travel easily through the GI tract. As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts. In certain portions of the GI tract, such as the stomach, the ingestible device 100 may be free to move or rotate in any direction. In other portions of the GI tract, the movement of the ingestible device 100 may be restricted. For example, in the relatively narrow confines of the small intestine, the walls of the small intestine may squeeze down on the ingestible device, forcing the ingestible device 100 to orient itself longitudinally along the length of the small intestine. In this case, the walls of the small intestine wrap around the longitudinally extending wall 104 of the ingestible device 100, and the ingestible device 100 travels through the small intestine with one of the ends 102A or 102B in front.

For illustrative purposes, the ingestible device 100 of FIG. 1 shows the first opening 106 located in a portion of the wall 104 and oriented radially, and the second opening 108 located near the first end 102A and oriented longitudinally. However, in some embodiments, the exact location and orientation of the first opening 106 and the second opening 108 may be different from that shown in FIG. 1. During transit through the GI Tract, natural contractions within the small intestine may apply pressure radially to different portions of the wall 104 of the ingestible device 100, which may force solids or fluids into the first opening 106. As new material (e.g., fluid and solid particulates from the small intestine or other portions of the GI tract) enters the curved chamber 110 through the first opening 106, older material already located in the curved chamber 110 may be naturally forced out of the curved chamber 110 through the second opening 108.

In some embodiments, a portion of the curved chamber 110 may be used as a sampling chamber, which may hold samples obtained from the GI tract. In some embodiments the curved chamber 110 is subdivided into sub-chambers, each of which may be separated by a series of one or more valves or interlocks. For example, sub-chambers may be used to retain multiple samples within different portions of the curved chamber 110. In some embodiments, the curved chamber 110 is connected to other chambers within the ingestible device 100, or other openings located on the housing of the ingestible device 100. This may allow new samples to be acquired in the curved chamber 110 while older samples of interest are still stored within the ingestible device 100. In some embodiments, the ingestible device 100 is equipped with sensors to detect the properties a sample contained in the sampling chamber, or the results of an assay technique applied to the sample. In some embodiments, the ingestible device 100 is configured to obtain and retain a sample within the sampling chamber, which may be retrieved at a later time.

In some embodiments, the first opening 106, the second opening 108, or the curved chamber 110 include one or more of a hydrophilic or hydrophobic material, a sponge, a valve, or an air permeable membrane. For example, a one-way valve may prevent material from entering the curved chamber 110 through the second opening 108. As an alternate example, placing an air permeable membrane within the curved chamber 110 near the second opening 108 may allow unwanted gasses and air bubbles to pass through the air permeable membrane and exit the curved chamber 110, while solid or liquid samples may be prevented from passing through the air permeable membrane, and are retained within the curved chamber 110. The air permeable membrane may also prevent solid or liquid samples from entering the curved chamber 110 through the second opening 108.

The use of a hydrophilic material or sponge may allow samples to be retained within the curved chamber 110, and may reduce the amount of pressure needed for fluid to enter through the first opening 106 and dislodge air or gas in the curved chamber 110. Examples of hydrophilic materials that may be incorporated into the ingestible device 100 include hydrophilic polymers such as polyvinyl alcohol, polyvinyl pyrrolidone, and the like. Similarly, materials that have undergone various types of treatments, such as plasma treatments, may have suitable hydrophilic properties, and may be incorporated into the investible device 100. Sponges may be made of any suitable material or combination of materials, such as fibers of cotton, rayon, glass, polyester, polyethylene, polyurethane, and the like. Sponges generally may be made from commercially available materials, such as those produced by Porex®.

As discussed in more detail below, in some embodiments, the sponges may be treated in order to change their absorbency or to help preserve samples.

In some embodiments, the sponges may be cut or abraded to change their absorbency or other physical properties.

Hydrophobic materials located near the second opening 108 may repel liquids, discouraging liquid samples from entering or exiting the curved chamber 110 through the second opening 108. This may serve a similar function as an air permeable membrane. Examples of hydrophobic materials which may be incorporated into the ingestible device 100 include polycarbonate, acrylics, fluorocarbons, styrenes, certain forms of vinyl, and the like.

The various materials listed above are provided as examples, and are not limiting. In practice, any type of suitable hydrophilic, hydrophobic, or sample preserving material may be used in the ingestible device 100, and the teachings discussed in relation to ingestible device 100 may be incorporated into any of the other ingestible devices described in this disclosure. Various methods for taking samples, controlling the movement of samples, or removing unwanted gasses, are discussed in detail in relation to FIGS. 2-9, and any of the various structures or techniques described in connection with FIGS. 2-9 may be incorporated into the ingestible device 100.

Figure 2:
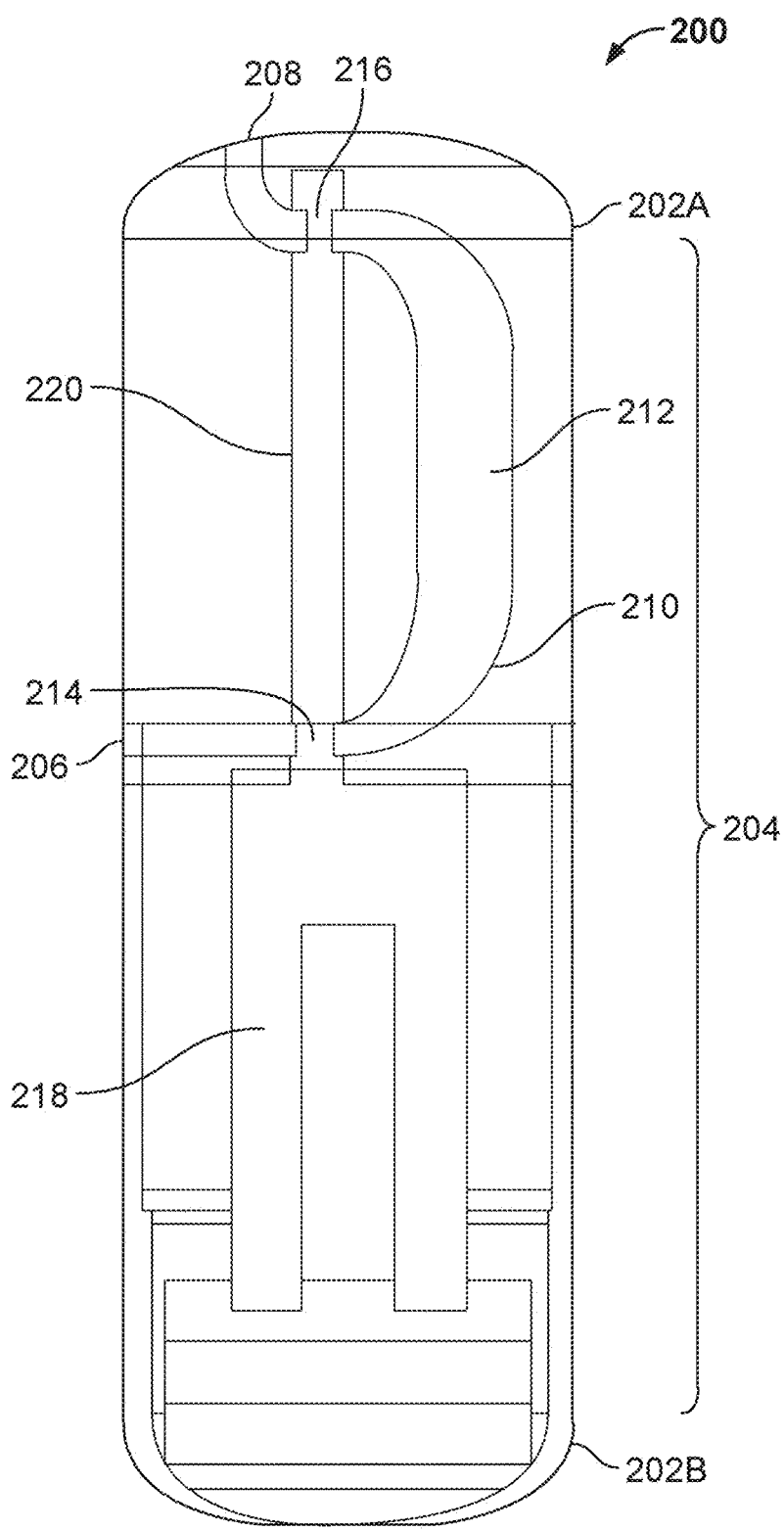
FIG. 2 shows another illustrative embodiment of an ingestible device, including various modifications that may be made to the ingestible device of FIG. 1.

FIG. 2 illustrates an example ingestible device 200 with multiple openings in the housing and various modifications that may be made to the ingestible device 100. Similar to the ingestible device 100, the ingestible device 200 has an outer housing with a first end 202A, a second end 202B, and a wall 204 extending longitudinally from the first end 202A to the second end 202B. Also similar to the ingestible device 100, the ingestible device 200 has a first opening 206 in the housing, which is connected to a second opening 208 in the housing. The connection between the first opening 206 and the second opening 208 forms a curved chamber 210 within the ingestible device 200.

In the ingestible device 200, a portion of the curved chamber 210 forms a sampling chamber 212. In some embodiments, the ingestible device 200 may include a sensor (not shown) within or proximate to the sampling chamber. This sensor may be used to detect a property of the sample. In some embodiments, an assay technique is applied to a sample within the sampling chamber, and the sensor may be used to detect the results of the assay technique. A first valve 214 is located between the first opening 206 and the sampling chamber 212. Similarly, a second valve 216 is located between the second opening 208 and the sampling chamber 212. In some embodiments, the valves 214 and 216 prevent a fluid from entering or exiting the sampling chamber 212, or may be used to isolate a sample within the sampling chamber 212.

The ingestible device 200 includes a mechanical actuator 218 coupled to the valves 214 and 216. In some embodiments, the mechanical actuator 218 is used to move one or both of the valves 214 and 216 between an open and a closed position. In some embodiments, the mechanical actuator 218 is controlled by a microcontroller, microprocessor, or other circuitry inside the ingestible device 200. In an open position, the first valve 214 may allow a sample to pass in and out of the sampling chamber 212 through the portion of the curved chamber 210 connected to the first opening 206. Similarly, in an open position, the second valve 216 may allow a sample to pass in and out of the sampling chamber 212 from the portion of the curved chamber 210 connected to the second opening 208. When the valves 214 and 216 are in the closed positions, they may not allow a sample to pass into or out of the sampling chamber 212.

In some embodiments, the valves 214 and 216 are rotary valves, pin valves, flap valves, butterfly valves, ball valves, plug valves, or any other suitable type of one-way or two-way valves, and may be the same or different types of valves. In some embodiments, one or both of the valves 214 and 216 are automatic valves that reseal themselves after a sample has been obtained, similar to the osmotic valve mechanism discussed in relation to FIG. 3. In some embodiments, one or both of the valves 214 and 216 include a pumping mechanism, such as the pumping mechanism discussed in relation to FIG. 9. For illustrative purposes, the ingestible device 200 is depicted with both of the valves 214 and 216 as moveable two-way valves coupled to the mechanical actuator 218. However, in some embodiments, the mechanical actuator 218 is coupled to only one of the valves, and the other valve may be replaced with a passive one-way valve. For example, the mechanical actuator 218 may be coupled to only the first valve 214, and the second valve 216 may be replaced with a passive one-way valve that allows gases, fluids, or solids to exit the sampling chamber 212 through the portion of the curved chamber 210 connected to the second opening 208. This may restrict fluid from entering the sampling chamber 212 from the second opening 208, but allow unwanted material to be removed from the sampling chamber 212 as the sample is obtained.

In some embodiments, the ingestible device 200 may be able to detect the approximate location of the ingestible device 200 within the GI tract. For example, it may be possible to use various combinations of light emitting diodes and sensors positioned along the ingestible device 200 to determine whether the device is in the stomach, small intestine, or large intestine. Methods for determining the location of an ingestible device within a gastrointestinal tract are described in greater detail in PCT Application No. PCT/US15/52500 filed 25 Sep. 2015, which is hereby incorporated by reference herein in its entirety. In these embodiments, the ingestible device 200 may be configured to use the mechanical actuator 218 to move the valves 214 and 216 into an open position in response to determining that the ingestible device 200 has reached a predetermined location within the GI tract. For example, a microcontroller on board the ingestible device 200 may be configured to open the valves 214 and 216 only when the ingestible device 200 is within the small intestine, thereby obtaining a sample from within the small intestine.

For illustrative purposes, the ingestible device 200 is depicted with the mechanical actuator 218, the first valve 214, and the second valve 216 oriented in a substantially straight line, with a single shaft 220 being used to couple the mechanical actuator 218 to the valves 214 and 216. However, in some embodiments, the orientation and/or positioning of the valves 214 and 216 relative to the position of the mechanical actuator 218 may be different than that shown, and the coupling of the mechanical actuator 218 to the valves 214 and 216 may also be different. In some embodiments, the mechanical actuator 218 simultaneously moves the valves 214 and 216. For example, in some embodiments the valves 214 and 216 are rotary valves, and they may be simultaneously opened and closed by rotating the shaft 220 that extends from the mechanical actuator 218 along the length of the ingestible device 200. As an alternate example, the valves 214 and 216 may be pin valves, and the pins may be attached to the shaft 220 that extends from the mechanical actuator 218 along the length of the ingestible device 200. In this case, the mechanical actuator 218 may open and close the valves by moving the shaft 220 linearly. This may be accomplished either by configuring mechanical actuator 218 to be a linear actuator, such as a solenoid. Alternately, the mechanical actuator 218 may be a rotary actuator, and the rotation may be converted into a linear motion. One skilled in the art will understand that this may be done any number of ways, for example, by coupling the mechanical actuator 218 to a ball screw mechanism, a threaded lead nut and lead screw mechanism, a rack and pinion mechanism, or the like.

In some embodiments, the ingestible device 200 does not include the second valve 216 at all. In this case, fluids and solids contained within the sampling chamber 212 may be free to exit through the second opening 208. Alternately, the second valve 216 near the second opening 208 may be replaced by an air-permeable membrane, which may allow gasses and unwanted air bubbles to exit the sampling chamber 212 through the second opening 208, while still retaining fluids and/or solids within the sampling chamber 212. Alternately, the second valve 216 near the second opening 208 may be replaced with a hydrophobic material. Similar to an air permeable membrane, an appropriately positioned hydrophobic material may be used to line the walls of the curved chamber 210 proximate to the second opening 208, which may allow gasses or unwanted air bubbles to exit the sampling chamber 212 through the second opening 208, while restricting some fluids from entering or exiting the sampling chamber 212 through the second opening 208. In some embodiments, one or more of the above described mechanisms may be combined in the same ingestible device. For example, the ingestible device 200 may implement the second valve 216 as a two-way valve, and also have hydrophobic material and an air-permeable membrane located near the second opening 208.

In some embodiments, the curved chamber 210 is connected to one or more sub-chambers (not shown). Each of these sub-chambers may be configured to hold one or more samples, and isolate the samples from both the sampling chamber 212, and the other sub-chambers. For example, each sub-chamber may be connected to the curved chamber 210 through a one-way valve, allowing samples to enter the sub-chamber from the curved chamber 210, but preventing the obtained samples from exiting the sub-chamber and re-entering either the curved chamber 210 or the sampling chamber 212. In general, any type of valve or other suitable mechanism may be used to isolate samples contained in the sub-chambers. In some embodiments, the ingestible device 200 distributes different samples into different sub-chambers at different times, or from different locations of the GI tract. For example, the ingestible device 200 may obtain a sample from the duodenum and distribute it into a first sub-chamber, and the ingestible device 200 may later obtain a sample from the ileum and distribute it into a second sub-chamber. In some embodiments, different types of assay techniques or diagnostics are applied to some of the samples contained in the different sub-chambers.

Figure 3:
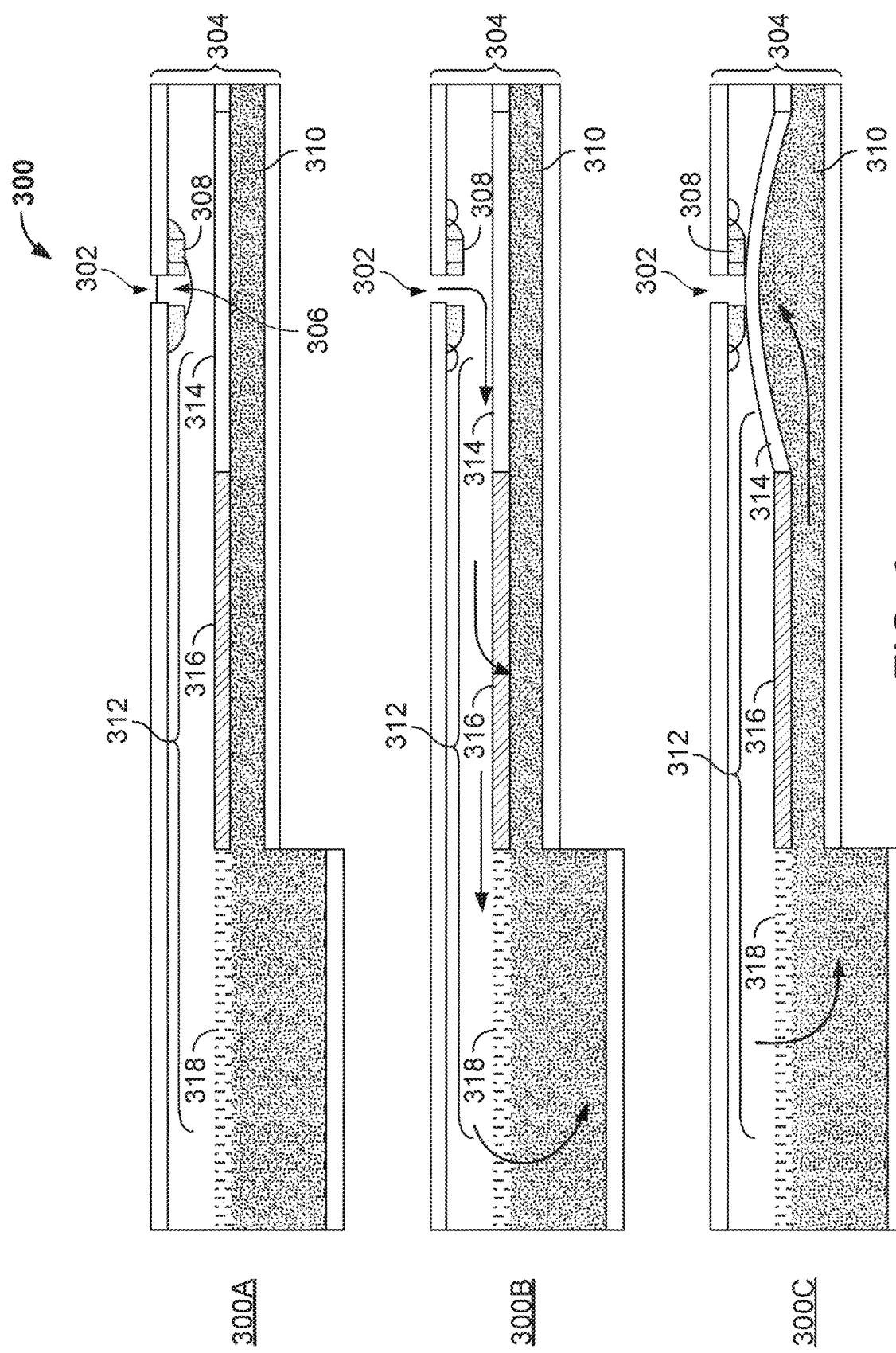
FIG. 3 shows an illustrative valve design that may be used to obtain a sample with an ingestible device.

FIG. 3 illustrates an example of an osmotic valve mechanism 300, which may be incorporated into an ingestible device in order to obtain samples. The osmotic valve mechanism 300 may be used in an ingestible device that features a first end, a second end, and a wall extending longitudinally between the first end and the second end, similar to the shape of the ingestible devices 100 (FIG. 1) and 200 (FIG. 2).

The osmotic valve mechanism 300 includes an inlet port 302, which is connected to a sampling chamber 304. In some embodiments, the inlet port 302 connects sampling chamber 304 directly or indirectly to an opening in the housing of an ingestible device.

The initial state of the osmotic valve mechanism 300 is shown in diagram 300A. As shown in diagram 300A, the inlet port 302 of the osmotic valve mechanism 300 is sealed using a single use sealing device 306 positioned within the inlet port 302. The single use sealing device 306 is positioned adjacent to a heating element 308. When it is time for the osmotic valve mechanism 300 to be opened (which may be determined by a localization mechanism that determines the ingestible device is located in a desirable portion of the GI tract), the heating element 308 applies heat to the sealing device 306, causing the sealing device 306 to deform and unseal the inlet port 302.

Figure 4:
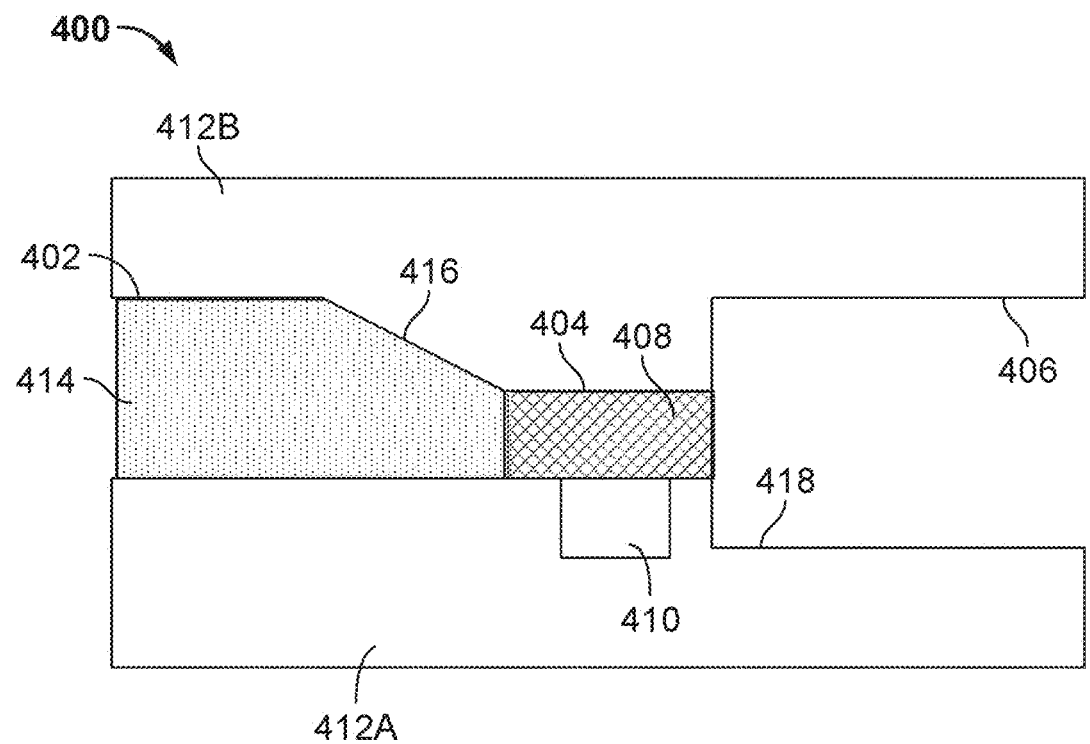
FIGS. 4 and 5 illustrate how the valve in FIG. 3 may be operated in order to obtain a sample.
Figure 5:
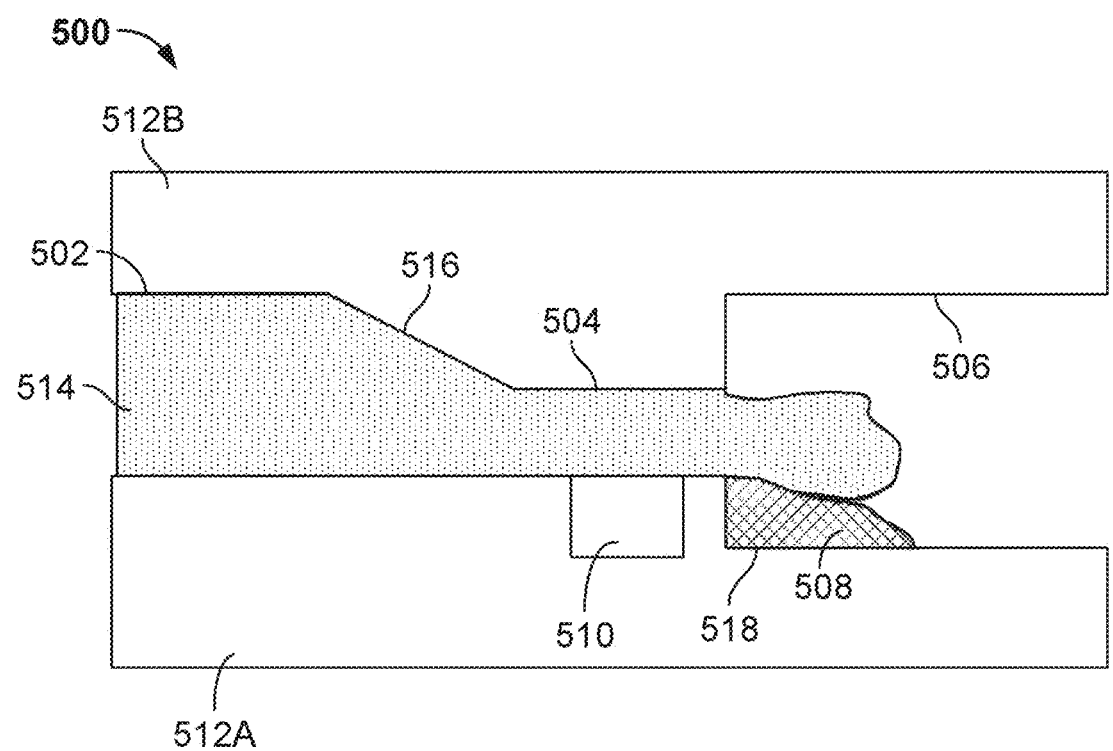

In some embodiments, the sealing device 306 may be a plug made out of a material that is meltable, deformable, and/or destroyable through the use of the heating element 308, such as wax. For example, in one embodiment, the heating element 308 may be a resistive heater that undergoes ohmic heating as an electrical current is passed through it, and the sealing device 306 is a wax plug. In some embodiments, the type of wax used to form the wax plug has a melting point between 38 degrees and 80 degrees Celsius, which is above the ambient temperature of a human body, but which may be easily achieved using the heating element 308. Some embodiments of the osmotic valve mechanism 300 may use a sealing device 306 that is melted or deformed at temperatures outside of the range described above, but practical considerations may be made to ensure that the osmotic valve mechanism 300 does not cause unwanted damage or burning to the GI tract. In some embodiments, a microprocessor is configured to control the heating element 308, causing it to generate heat. For example, the microprocessor may be configured to activate the heating element 308 once the ingestible device reaches a particular location within the GI tract. An example mechanism for unsealing the inlet port 302 is described in greater detail in relation to FIGS. 4 and 5. Although FIGS. 3, 4, and 5 depict the sealing device 306 as a type of plug, any type of suitable sealing device may be used. For example, in some embodiments, the sealing device includes a breakable membrane, which may be destroyed when heat is applied to the membrane. In some embodiments, the osmotic valve mechanism 300 does not include a heating element 308, and the sealing device 306 is melted, deformed, destroyed, or dislodged from the inlet port 302 by a mechanical actuator, or through electromagnetic fields. For example, the sealing device 306 may be a membrane that will rupture when a sufficiently large electrical current or magnetic field is applied to the membrane.

Inside the sampling chamber 304 of the osmotic valve mechanism 300 is an absorptive material 310, and at least a portion of the absorptive material 310 is located near the inlet port 302. The absorptive material 310 may include any suitable sponge material or hydrophilic material, such as any of the materials described in relation to FIG. 1. The portion of the absorptive material 310 located near the inlet port 302 may have a tendency to expand when it comes into contact with fluids. The osmotic valve mechanism 300 has a barrier 312 inside the sampling chamber 304, which is divided into three portions. The first portion of the barrier 312 is a flexible membrane 314, the second portion of the barrier 312 adjacent to the flexible membrane 314 is a rigid portion 316, and the third portion of the barrier 312 adjacent to the rigid portion 316 is a semi-permeable membrane 318.

The barrier 312 within the sampling chamber 304 is positioned between the inlet port 302 and the absorptive material 310, covering a surface of the absorptive material 310. When the inlet port 302 is unsealed, a sample (e.g., a fluid sample containing solid particulates taken from the GI tract) enters the sampling chamber 304 through the inlet port 302, and begins to fill the sampling chamber 304. The absorptive material 310 may have a natural tendency to expand when it comes into contact with a fluid sample. However, by covering a surface of the absorptive material 310, the barrier 312 may allow only certain portions of absorptive material 310 to expand. The barrier 312 may also direct the flow of a fluid sample as it enters the sampling chamber 304, and allow the fluid sample to come into contact with only certain parts of the absorptive material 310.

Diagram 300B shows the osmotic valve mechanism 300 shortly after the inlet port 302 is unsealed. Once the inlet port 302 is unsealed, the sampling chamber 304 may be opened, and a sample may enter the sampling chamber 304 through the inlet port 302. In some embodiments, the sample cannot cross the flexible membrane 314 and contact the absorptive material 310. As a result, the flexible membrane 314 may be used to guide the sample as it enters the sampling chamber 304. Similarly, in some embodiments the sample cannot cross the rigid portion 316 of the barrier 312, and the rigid portion 316 may also be used to guide the sample as it enters the sampling chamber 304. The semi-permeable membrane 318 allows at least a portion of the sample to pass through the semi-permeable membrane and contact the absorptive material 310. This may allow the sample to be absorbed by the absorptive material 310 after the sample has filled the top portion of the sampling chamber 304, which in turn may cause the absorptive material 310 to begin to expand.

Diagram 300C shows the state of the osmotic valve mechanism 300 after the absorptive material 310 has absorbed a portion of the sample. The portion of the absorptive material 310 under the flexible membrane 314 expands when the absorptive material 310 absorbs the sample. As the absorptive material 310 expands, the flexible membrane 314 is forced up against the inlet port 302, effectively sealing the inlet port 302 from the sampling chamber 304. In some embodiments, the rigid portion 316 prevents the portion of the absorptive material 310 under the rigid portion 316 from expanding. In some embodiments, the semi-permeable membrane 318 may be rigid, and prevent the portion of the absorptive material 310 adjacent to the semi-permeable membrane 318 from expanding.

After the absorptive material 310 expands, causing the inlet port 302 to be resealed, a portion of the sample may be confined within the sampling chamber 304. Once a sample has been properly confined, it may be possible to apply a wide range of assay techniques or diagnostics to the sample. In some embodiments, the portion of the sampling chamber 304 between the rigid portion 316 and the wall of the sampling chamber forms a testing area. For example, a sensor may be placed within or proximate to the sampling chamber 304 in order to study the portion of the sample contained within the testing area located above the rigid portion 316. This sensor may be used to study properties of the sample, or it may be used to detect the results of an assay technique applied to the sample.

Diagram 300C is shown for illustrative purposes only, and is not limiting. In some embodiments, the osmotic valve mechanism 300 does not include the barrier 312, or one or more portions of the barrier 312 are excluded or rearranged within the sampling chamber 304. For example, the location of the rigid portion 316 and the semi-permeable membrane 318 may be reversed, or the rigid portion 316 may be removed and the semi-permeable membrane 318 extended so that it connects directly with the flexible membrane 314. When the osmotic valve mechanism 300 does not include a barrier 312 or does not include the flexible membrane 314, a portion of the absorptive material 310 near the inlet port 302 may expand and clog the inlet port 302, effectively resealing the inlet port 302.

In some embodiments, the material used to form the absorptive material 310 expands at a controlled rate, which may ensure that sufficient time has passed for the sample to enter the sampling chamber 304 and for the sampling chamber 304 to be filled before the inlet port 302 is resealed. This may be particularly useful for embodiments where the osmotic valve mechanism 300 does not include a flexible membrane 314 and/or the semi-permeable membrane 318. In some embodiments, a portion of the absorptive material 310 is covered by a dissolvable film or membrane, which may prevent the absorptive material 310 from expanding until a sufficient amount of time has passed for the film to dissolve.

In some embodiments, the sampling chamber 304 is connected to one or more sub-chambers (not shown). Each of these sub-chambers may be configured to hold samples, and isolate the samples from both the sampling chamber 304, and the other sub-chambers. For example, each sub-chamber may be connected to the sampling chamber 304 through a one-way valve, allowing samples to enter the sub-chamber from the sampling chamber, but preventing the obtained samples from exiting the sub-chamber. As an alternate example, each of the sub-chambers may employ a sealing device, heating element, and absorptive material arranged similar to osmotic valve mechanism 300. In these embodiments, each of the sub-chambers may be opened by activating their respective heating elements, and may be automatically sealed off from the sampling chamber 304 after a sufficient amount of the sample has been obtained. In general, any type of valve or other suitable mechanism may be used to isolate samples contained in the sub-chambers. In some embodiments, similar to ingestible device 200, an ingestible device employing multiple sub-chambers in conjunction with the osmotic valve mechanism 300 may distribute different samples into different sub-chambers at different times, or from different locations of the GI tract.

It will be understood by one skilled in the art that variations of the osmotic valve mechanism 300 may be combined with any of the other ingestible devices described in this disclosure. For example, in some embodiments of the ingestible device 200 shown and described in relation to FIG. 2, one or both of the valves 214 and 216 may be replaced with certain embodiments of the osmotic valve mechanism 300. One or both of the valves 214 and 216 may include a sealing device that can be destroyed or deformed (e.g., by the mechanical actuator 218 or through a heating element), and one or both of the valves 214 and 216 may be automatically resealed by the expansion of absorptive material located within the sampling chamber 212.

FIGS. 4 and 5 illustrate in detail how some embodiments of the osmotic valve mechanism 300 (FIG. 3) may be operated in order to obtain a sample.

FIG. 4 shows a detailed view of an inlet port 400, which may be incorporated into osmotic valve mechanism 300, prior to being unsealed. The inlet port 400 features an exterior portion 402, which is separated by a middle portion 404 from an interior portion 406. The middle portion 404 of the inlet port 400 contains a sealing device 408, which may be the same as sealing device 306 shown and described in relation to FIG. 3. A heating element 410 is located near the middle portion 404, and adjacent to the sealing device 408. The sides of the inlet port 412A and 412B form the shape of the inlet port 400, and may be constructed from an insulating material, such as insulating ceramic, or polymers such as polyamide-imide, polyphenylene sulfide, polyphenylene oxide, and the like. For illustrative purposes, the exterior portion 402 of the inlet port 400 is depicted as being filled with a sample 414, which may be a fluid sample obtained from the GI tract. However, in some embodiments, the inlet port 400 may be operated regardless of whether a sample 414 is actually contained in the exterior portion 402. The exterior portion 402 and the interior portion 406 are wider than the middle portion 404. A sloped wall 416 gradually reduces the width of the exterior portion 402, to transition from the wider width of the exterior portion 402 to the narrower width of the middle portion 404. This configuration may reduce the overall volume of the sealing device 408 (compared to a configuration with a wider middle portion 404), and reduce the surface area of the sealing device 408 exposed to the sample 414, which may reduce the amount of heat lost from the sealing device 408 to the sample 414. In turn, this may make it easier to raise the temperature of the sealing device 408 using the heating element 410. In some embodiments, the geometry of the inlet port 400 may allow an air pocket (not shown) to form in the exterior portion 402, separating the sealing device 408 from fluid contained within the GI tract. This may act as an insulating barrier around the sealing device 408, and also make it easier to raise the temperature of the sealing device 408 using the heating element 410. Moreover, the larger width of the interior portion 406 relative to the middle portion 404 forms a remnant capture area 418, which may hold the remnants of the sealing device 408 after the inlet port 400 is unsealed.

In some embodiments, the exterior portion 402 of the inlet port 400 may be connected directly or indirectly to an opening in the housing of an ingestible device. In some embodiments, there is nothing to restrict a sample from entering the opening, and, at any given time, the exterior portion 402 of the inlet port 400 may be filled with a fluid sample 414 gathered from whatever portion of the GI tract the ingestible device is located within.

Sealing device 408 prevents the fluid sample 414 contained within the exterior portion 402 of the inlet port 400 from entering the interior portion 406 of the inlet port 400. For simplicity, FIGS. 4 and 5 depict the sealing device 408 as a plug, which forms a seal that may be broken by using a heating element 410. However, in some embodiments the sealing device 408 may be any other type of breakable seal or valve used within the middle portion 404 to separate the exterior portion 402 of the inlet port 400 and the interior portion 406 of the inlet port 400.

In some embodiments, the heating element 410 may be operated by a microcontroller. For example, the microcontroller may be configured to operate the heating element 410 and unseal the inlet port 400 when the ingestible device is in a certain portion of the GI tract. The sides of the inlet port 412A and 412B may be formed from an insulating material, which may shield the ingestible device and the fluid sample 414 from the heat generated by the heating element 410. This may also help to focus the heat produced by heating element 410 in the direction of the sealing device 408, and may reduce the total amount of power to drive the heating element 410 to melt, deform, or destroy the sealing device 408.

In some embodiments, the dimensions of the inlet port 400 are chosen such that a fluid sample 414 is naturally drawn into the exterior portion 402, and ultimately through the middle portion 404 into the interior portion 406, through capillary action. Typically, the cross-section of the exterior portion 402, the middle portion 404, and the interior portion 406 will be square, circular, or rectangular, but any type of cross-section may be used. The overall cross-sectional area of the exterior portion 402, the middle portion 404, and the interior portion 406 of the inlet port 400 is typically less than 50 square millimeters given the size constraints of the ingestible device, with 0.2 to 2 square millimeters being common. However, the cross-sectional areas listed above are only examples, and any cross-sectional area may be chosen in order to better draw in samples from the different portions of the GI tract. One skilled in the art will understand that the exact shape and dimensions will depend on the physical properties of the sample to be acquired, and some embodiments may use cross-sections other than the ones mentioned above.

FIG. 5, shows a detailed view of an inlet port 500, which may be incorporated into osmotic valve mechanism 300, after it has been unsealed.

After the heating element 510 has heated the sealing device 508 sufficiently, the sealing device 508 may deform, melt, or otherwise be destroyed, effectively unsealing the inlet port 500. Once the inlet port 500 is unsealed, the fluid sample 514 is able to flow naturally from the exterior portion 502 of the inlet port 500 to the interior portion 506 of the inlet port 500 through the middle portion 504. Similar to the embodiments described in relation to FIG. 4, the sides 512A and 512B of the inlet port may be made of an appropriate insulating material, and form the shape of the inlet port 500, the exterior portion 502 with the sloped wall 516, the middle portion 504, and the interior portion 506 along with the remnant capture area 518. As the fluid sample 514 enters the interior portion 506 of the inlet port 500, the natural flow of the fluid sample 514 may carry any of the remnants of the sealing device 508 into the remnant capture area 518 located within the interior portion 506. In some embodiments, once the melted or deformed remnants of the sealing device 508 cease to be in contact with the heating element 510 and instead come into contact with the insulating material that make up the walls of the remnant capture area 518, the remnants of the sealing device 508 re-solidifies or re-forms along the walls of the remnant capture area 518. As a result, the remnant capture area 518 may provide a location for the re-solidified remnants of the sealing device 508 to be stored, and may prevent the remnants of the sealing device 508 from impeding the flow of the sample 514.

In some embodiments, electromagnetic forces are used to attract the remnants of the sealing device 508 to the remnant capture area 518. For example, the sealing device (e.g., the sealing device 408) may be made from a magnetic material, and an induced or permanent magnetic field may be used to attract the remnants of the sealing device 508 to the remnant capture area 518. This magnetic field may be applied after the heating element 510 is activated, and until the remnants of the sealing device 508 re-solidify or re-form within the remnant capture area 518.

It will be understood that the embodiments described by FIGS. 3, 4, and 5, are merely illustrative, and they may be modified and combined with other techniques for drawing in or pumping fluid samples without departing from the spirit and scope of this disclosure. For example, to encourage samples to be drawn into the sampling chamber 304, the sampling chamber 304 may contain a low-pressure vacuum, and samples may be forcibly drawn into the sampling chamber 304 when the inlet port 302 is unsealed. A similar effect may also be produced by connecting the sampling chamber 304 to a sub-chamber containing a low-pressure vacuum, or by using by using a mechanical actuator to either pump the fluid samples or to increase the volume of the sampling chamber 304. In some embodiments, the geometry and relative size of the exterior portions 402 and 502, the middle portions 404 and 504, and interior portions 406 and 506, may be different from those depicted in FIGS. 4 and 5. For example, the different portions 402, 404, 406, 502, 504, and 506 may have a uniform width, and the sloped walls 416 and 516 and/or the remnant capture areas 418 and 518 are not included. As another example, a sloped wall may be used to form the remnant capture areas 418 and 518.

Figure 6:
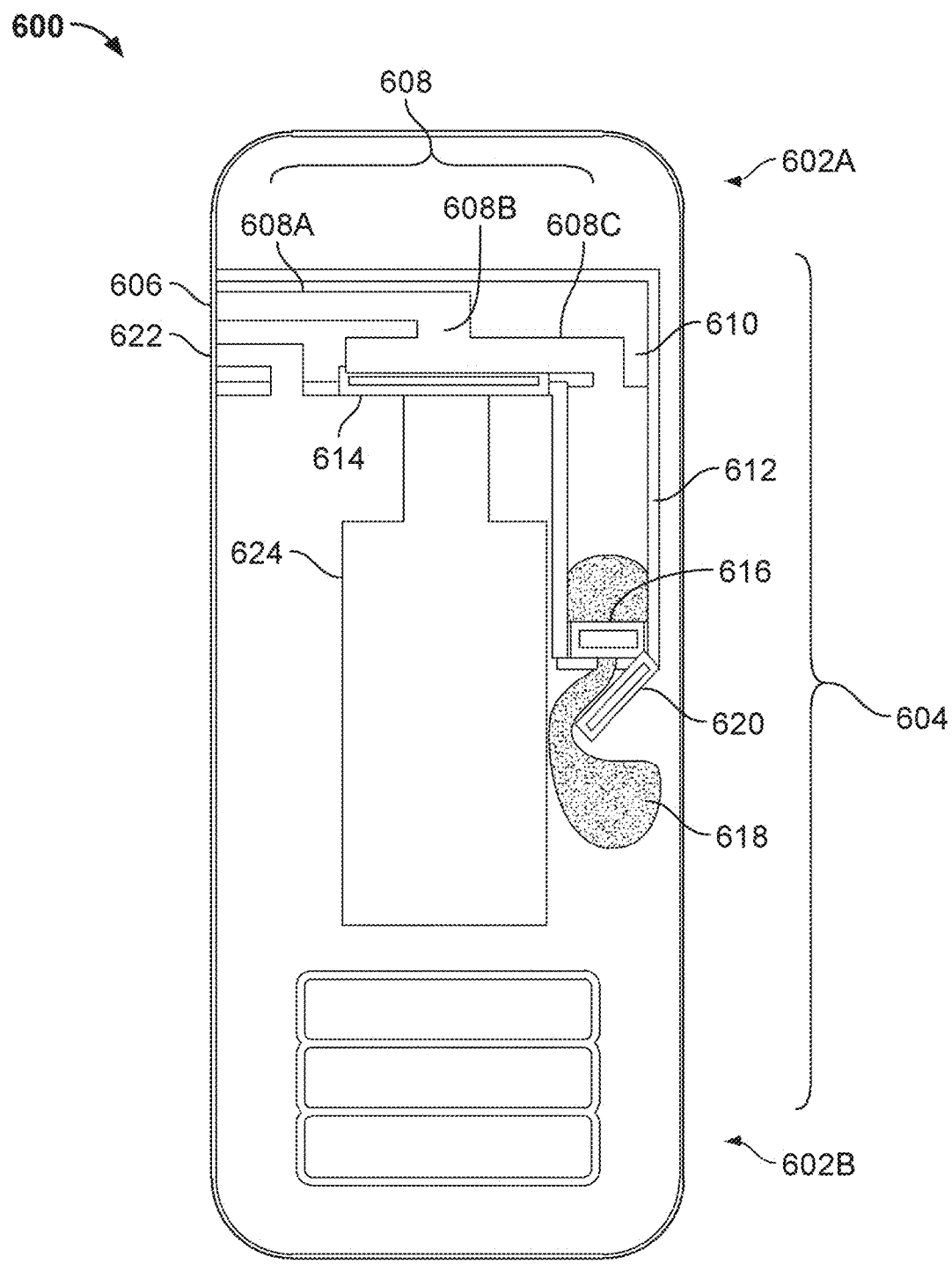
FIG. 6 shows an illustrative embodiment of an ingestible device with a sampling chamber that includes an exit port.

FIG. 6 illustrates another example of an ingestible device 600 with a sampling chamber that includes an exit port. Similar to the ingestible devices 100 and 200, the ingestible device 600 is designed to have an outer housing with a first end 602A, a second end 602B, and a wall 604 extending longitudinally from the first end 602A to the second end 602B. The ingestible device 600 has an opening 606 in the housing, which allows samples to enter the ingestible device 600 from the surrounding environment. The ingestible device 600 has an inlet region 608 connected to the opening 606. The inlet region 608 is connected to an entry port 610 of a sampling chamber 612. The inlet region 608 is divided into three portions. A first portion 608A of the inlet region 608 is connected to the opening 606 and a second portion 608B, and a third portion 608C is connected to the entry port 610 of the sampling chamber 612. The second portion 608B connects the first portion 608A to the third portion 608C, and may contain a moveable valve 614 that is used to prevent samples from flowing through the inlet region 608, and isolate the first portion 608A of the inlet region 608 from the third portion 608C of the inlet region 608.

The ingestible device 600 has a mechanical actuator 624 coupled to the moveable valve 614. In some embodiments, a microprocessor or microcontroller is configured to control the mechanical actuator 624 and move the moveable valve 614 between an open and a closed position. For example, the microcontroller may be configured to move the moveable valve 614 into an open position after the ingestible device reaches a particular location within the GI tract. In some embodiments, the mechanical actuator may be driven by a set of batteries or other power source located within the ingestible device 600. When the moveable valve 614 is moved into an open position, a sample may be allowed to flow through the inlet region 608, and enter the sampling chamber 612 through the entry port 610. When the moveable valve 614 is in a closed position, the sample is prevented from flowing through the inlet region 608 and reaching the sampling chamber 612 from the opening 606.

For illustrative purposes, FIG. 6 depicts the moveable valve 614 as a diaphragm valve, which uses a mechanical actuator 624 to move a flexible diaphragm in order to seal or unseal an aperture in the second portion 608B of the inlet region 608, which may effectively block or unblock the inlet region 608. However, it will be understood that, in some embodiments, the moveable valve 614 may be a different type of valve. For example, in some embodiments the moveable valve 614 may be replaced by a pumping mechanism, such as the pumping mechanism described in relation to FIG. 9. As another example, in some embodiments the moveable valve 614 is replaced with an osmotic valve, similar to the embodiments described in relation to FIGS. 3, 4, and 5. Several examples of other different valve types are described in relation to FIG. 7.

The sampling chamber 612 of the ingestible device 600 has an exit port 616 located on the opposite end of the sampling chamber 612 from the entry port 610. In general, the exit port 616 may be located anywhere within the sampling chamber 612. The exit port 616 is configured to allow air or gas 618 to exit the sampling chamber 612, while preventing at least a portion of the sample obtained by the ingestible device 600 from exiting the sampling chamber 612. For example, the exit port 616 may include a gas-permeable membrane, which allows the gas 618 to exit the sampling chamber 612, but which would prevent a liquid or solid sample from leaving the sampling chamber 612 through the exit port 616. Allowing the gas 618 to exit the sampling chamber 612 may prevent pressure from building up within the sampling chamber 612 as the sample enters through the entry port 610. This may result in the sample being drawn into the sampling chamber 612 more easily, and result in increasing the overall volume of the sample able to be collected by the ingestible device 600, and increasing the ease with which the sample is brought into the sampling chamber 612.

The ingestible device 600 includes a one-way valve 620 as part of the exit port 616. This valve may prevent the gas 618 from re-entering the sampling chamber 612. However, in some embodiments the one-way valve 620 may be excluded from the ingestible device 600. In some embodiments, the exit port 616 includes a gas permeable membrane. This gas permeable membrane may lose its permeability when it is placed in contact with the sample. For example, the gas permeable membrane may include a spongy material that allows the gas 618 to exit the sampling chamber 612 through the exit port 616. Once the spongy material becomes moist through contact with the sample, it may become no longer gas permeable, or the permeability may be greatly reduced, thereby preventing the gas 618 from reentering the sampling chamber 612. In some embodiments, the gas permeable membrane may include expanded polytetrafluoroethylene, polypropylene, or the like. In some embodiments, the material used to make the gas permeable membrane may be filter-like, as opposed to sponge-like materials. Generally, the gas permeable membrane may be made of any material that allow gas to permeate, but which prevents liquid from flowing through the membrane due to sufficient resistance or surface tension effects.

In the ingestible device 600, the exit port 616 is connected to a volume within the housing of ingestible device 600 outside of the sampling chamber. Depending on the manufacturing process used to produce the ingestible device 600, the volume within the housing of the ingestible device 600 may contain air or some other type of gas.

The ingestible device 600 includes an outlet port 622, which is connected to the volume within housing of the ingestible device 600. The outlet port 622 may provide a path for the gas 618 to exit the ingestible device 600 and be released into the environment surrounding the ingestible device 600. This may be advantageous when the volume of gas 618 is relatively large, since it may prevent pressure from building up within the housing of the ingestible device 600. In some embodiments, the ingestible device 600 does not include an outlet port 622, and the gas 618 stays inside the volume of the ingestible device 600. In some embodiments, the outlet port 622 is directly or indirectly connected to the exit port 616, for example, by a tube or channel. In some embodiments, the exit port 616 leads directly from the sampling chamber 612 to an opening in the ingestible device 600, and the exit port 616 may effectively replace the outlet port 622. In some embodiments, the outlet port 622 may contain a gas permeable membrane, a one-way valve, a hydrophobic channel, or some other mechanism to avoid unwanted material, (e.g., fluids and solid particulates from within the GI tract), from entering the ingestible device 600 through the outlet port 622.

In some embodiments, the ingestible device 600 may include a sensor within or proximate to the sampling chamber 612. For example, this sensor may be used to detect various properties of a sample contained within the sampling chamber 612, or this sensor may be used to detect the results of an assay technique applied to the sample contained within the sampling chamber 612.

In some embodiments, a hydrophilic sponge is located within the sampling chamber 612, and the hydrophilic sponge may be configured to absorb the sample as the sample enters the sampling chamber 612. In some embodiments, the hydrophilic sponge fills a substantial portion of the sampling chamber 612, and holds the sample for an extended period of time. This may be particularly advantageous if the sample is collected from the ingestible device 600 after the ingestible device 600 exits the body. In some embodiments, the hydrophilic sponge is placed on only certain surfaces or fills only certain portions of the sampling chamber 612. For example, it may be possible to line certain walls (or all walls) of the sampling chamber 612 with a hydrophilic sponge to assist in drawing in the sample, while leaving some (or none) of the walls of the sampling chamber 612 uncovered. Leaving walls uncovered may allow the use of diagnostics or assay techniques that involve a relatively un-obscured optical path. An example of such an embodiment is described in detail in relation to FIG. 8. In some embodiments, the sponge material may be placed on all walls of the sampling chamber 612. This may prevent unwanted ambient light from entering the sampling chamber 612, which may be useful for certain types of low light detection assays. In some embodiments, an opaque material is used to cover some or all sides of the sampling chamber 612. This may also prevent unwanted ambient light from entering the sampling chamber 612.

In some embodiments, the ingestible device 600 may include a sealed vacuum chamber connected to the exit port 616, or connected directly or indirectly to the sampling chamber 612. The sealed vacuum chamber may have an internal pressure that is substantially lower than ambient pressure of the sampling chamber 612 and/or the inlet region 608. In these embodiments, the ingestible device 600 unseals the vacuum chamber in order to reduce the pressure within the sampling chamber. This change in pressure may force the sample to be sucked into the sampling chamber, or allow the sample to be drawn into the sampling chamber quickly.

For simplicity, FIG. 6 depicts only a single sampling chamber 612, but it will be understood that the inlet region 608 may be connected to multiple sampling chambers arranged throughout the device, each of which may be controlled independently through the use of one or more valves. For example, in some embodiments there may be one or more sub-chambers connected to the inlet region 608. Each of the sub-chambers may be configured to hold samples gathered from within the GI tract, and keep those samples isolated. In general, any type of valve or other suitable mechanism may be used to isolate samples contained in the sub-chambers, including any of the valves or mechanisms described in relation to FIGS. 1-5. In some embodiments, the ingestible device 600 distributes different samples into each of the different sub-chambers at different times, or from different locations within the GI tract. For example, the ingestible device 600 may accomplish this by opening up a valve to connect the interior of inlet region 608 to the appropriate sub-chamber before opening up the inlet region 608 to draw in the sample from the opening 606 in the housing.

Figure 7:
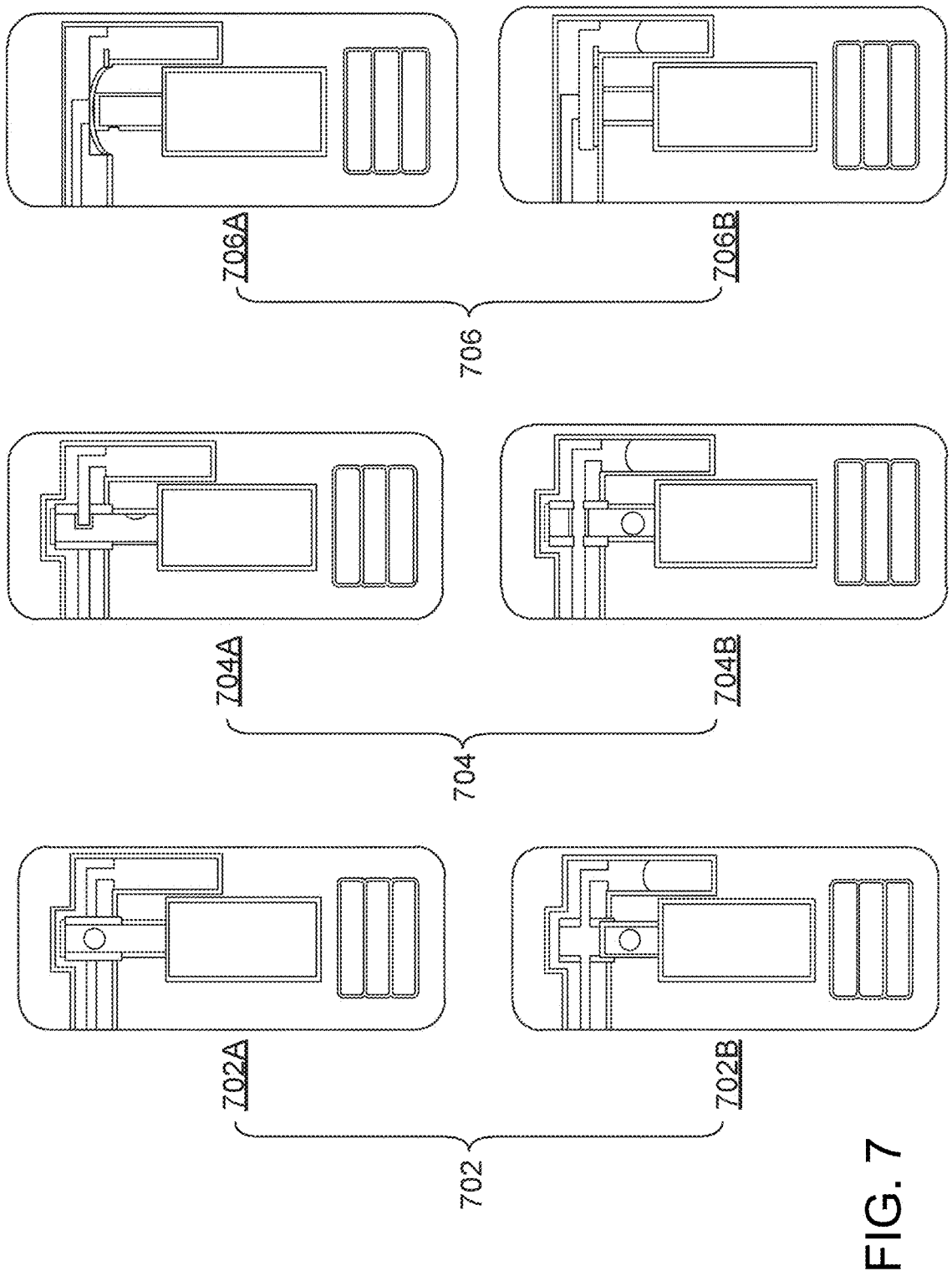
FIG. 7 shows different illustrative valve designs that may be incorporated into an ingestible device.

FIG. 7 depicts different types of moveable valves that may be incorporated into an ingestible device, such as the ingestible devices 100, 200 or 600. The ingestible device 702 illustrates how a pin valve may be used as a moveable valve (e.g., as moveable valve 614 of ingestible device 600 (FIG. 6)), with diagram 702A showing the pin valve in a closed position, and diagram 702B showing the pin valve in an open position. In the ingestible device 702, a mechanical actuator may be configured to move the pin valve linearly in order to switch between an open position and a closed position. For example, in diagram 702A, the ingestible device 702 has a pin inserted into the inlet port, thereby preventing the sample from flowing into the sampling chamber from the opening in the ingestible device 702. In diagram 702B, the ingestible device 702 has a pin that has been removed from the inlet port, allowing the sample to flow freely into the sampling chamber from the opening in the ingestible device 702. In order to generate linear motion, the mechanical actuator may be a linear actuator, such as a solenoid. Alternately, the mechanical actuator may be a rotary actuator, and the rotation may be converted into a linear motion. One skilled in the art will understand that this may be done any number of ways, for example, by coupling the mechanical actuator to a ball screw mechanism, a threaded lead nut and lead screw mechanism, a rack and pinion mechanism, or the like.

Ingestible device 704 illustrates how a rotary valve may be used as a moveable valve (e.g., as moveable valve 614 of ingestible device 600 (FIG. 6)), with diagram 704A showing the rotary valve in a closed position, and diagram 704B showing the rotary valve in an open position. In diagram 704A, the ingestible device 704 has a rotary pin oriented such that the sample is prevented from entering the sampling chamber from the opening in the ingestible device 704. In diagram 704B, the ingestible device 704 has a rotary pin that has been rotated into an orientation where the sample is free to flow into the sampling chamber from the opening in the ingestible device 704. In order to operate the rotary valve, the mechanical actuator in ingestible device 704 may be a rotatory actuator, which is capable of rotating the rotary pin to switch between the open position and the closed position.

Ingestible device 706 illustrates how a flexible diaphragm, or diaphragm valve, may be used as a moveable valve (e.g., as moveable valve 614 of ingestible device 600 (FIG. 6)), with diagram 706A showing the diaphragm valve in a closed position, and diagram 706B showing the diaphragm valve in an open position. In diagram 706A, the ingestible device 706 has a diaphragm valve in a closed position, with the flexible diaphragm being pressed against an aperture in the inlet region due to the pressure generated by the mechanical actuator against the flexible diaphragm. This may effectively block a sample from flowing through the inlet region, and thereby preventing a sample from entering the sampling chamber from the opening in the ingestible device 706. In diagram 706B, the ingestible device 706 has a diaphragm valve in an open position, with the pressure removed from the flexible diaphragm. The diaphragm returns to a position away from the aperture in the inlet region, allowing a sample to flow freely into the sampling chamber from the opening the in ingestible device 706.

In some embodiments, ingestible device 706 has a spring mechanism near the diaphragm or in direct contact with the diaphragm. The spring mechanism may apply pressure to the diaphragm to oppose the pressure applied by the mechanical actuator, which may cause the flexible diaphragm to be moved into an open position when the mechanical actuator is not applying pressure to the flexible diaphragm. Additionally, this may ensure that the diaphragm valve remains open when the mechanical actuator is not applying pressure across the flexible diaphragm.

In some embodiments, moving the mechanical actuator from a closed position to an open position causes a volume of the inlet region within the ingestible device to increase. This may cause the pressure within the inlet region to be reduced, generating suction to draw a sample into the inlet region. Similarly, moving the mechanical actuator from an open position to a closed position may cause the volume of the inlet region to be reduced. This may cause the pressure within the inlet region to be increased, pushing the sample out of the inlet region. Depending on the design of the inlet region, the mechanical actuator, and the moveable valve, this may push the sample into the sampling chamber rather than pushing the sample back through the opening in the ingestible device. An example of such a design is described in greater detail in relation to FIG. 9.

Figure 8:
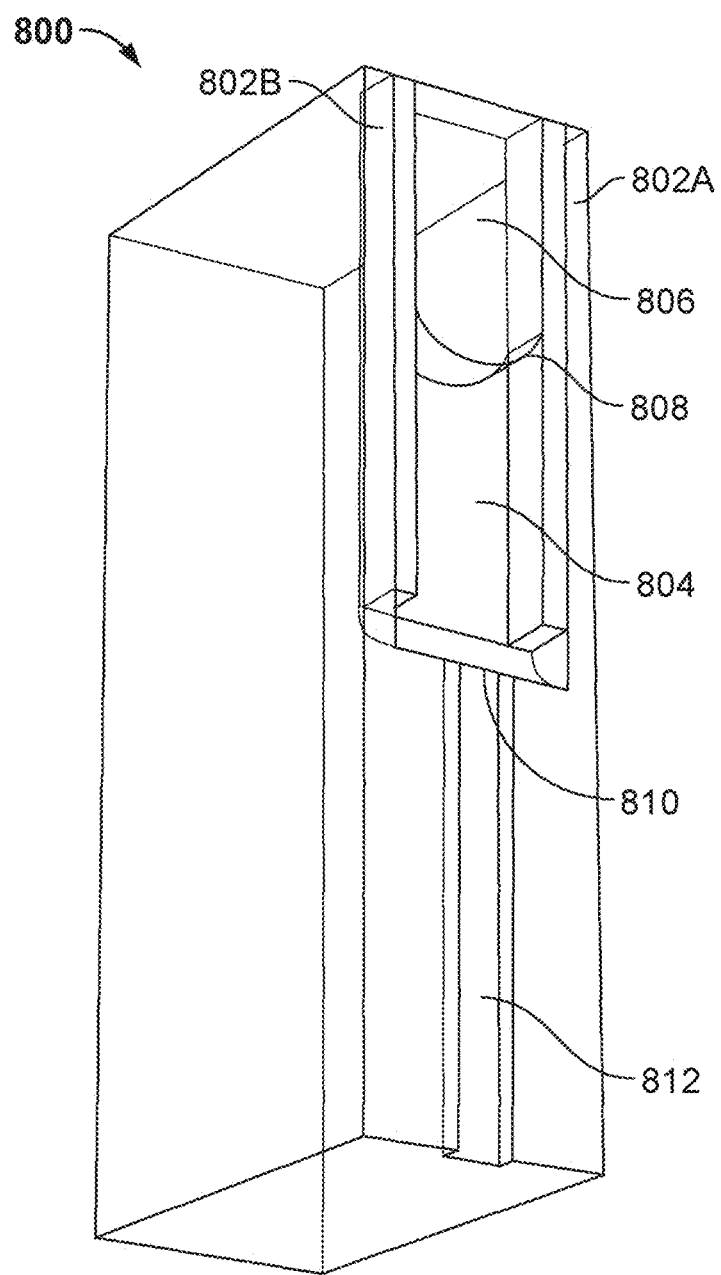
FIG. 8 shows an illustrative sampling chamber that may be incorporated into an ingestible device.

FIG. 8 illustrates an example of a sampling mechanism that may be incorporated into an ingestible device, such as the ingestible devices 100, 200, 600, and 702-706. The sampling mechanism 800 is partially lined with hydrophilic sponges 802A and 802B. In between the hydrophilic sponges 802A and 802B is a testing region 804 within the sampling mechanism 800. The hydrophilic sponges 802A and 802B attract a liquid or fluid sample 806, and may draw the sample 806 into the sampling mechanism 800. As the hydrophilic sponges 802A and 802B are saturated with the sample 806, a meniscus 808 is formed at the end of the sample 806, between the hydrophilic sponges 802A and 802B. This system may be useful for acquiring particularly viscous samples, which may have difficulty flowing into the sampling mechanism 800 naturally.

The sampling mechanism 800 includes an exit port 810 connected to a channel 812. As the sample 806 is drawn into the sampling mechanism 800, air or gas contained in the sampling mechanism 800 may be pushed out of the sampling mechanism 800 through the exit port 810 and into the channel 812. This may avoid gas being trapped within the sampling mechanism 800, which in turn may avoid pressure building inside of the sampling mechanism 800 and preventing the sample 806 from being drawn into the testing region 804.

In some embodiments, the sampling mechanism 800 may not include an exit port 810 or a channel 812, and any air or gas in the sampling mechanism 800 may be allowed to remain within the sampling mechanism 800. In some embodiments, the sampling mechanism 800 may be filled with a low pressure vacuum, attached to a pump or other mechanism to create a vacuum, or attached to a sealed chamber containing a low pressure vacuum that may be unsealed. The use of a vacuum may allow the sampling mechanism 800 to forcibly draw in a sample.

In some embodiments, an ingestible device may include sensors or diagnostics to study the sample 806 contained within the sampling mechanism 800. Because there is no sponge material on the front and back walls of the testing region 804, information about the sample 806 contained within the testing region 804 may be gathered by using sensors and/or assay techniques that involve a clear optical path, which would otherwise be obscured by a sponge (e.g., the hydrophilic sponges 802A and 802B). For example, light sources and/or optical sensors may be placed near the front and/or back walls in order to test optical properties of the sample, or to detect the results of certain assay techniques.

It will be understood by those skilled in the art that the sampling mechanism 800 depicted in FIG. 8 is merely illustrative, and the general techniques described in relation to FIG. 8 may be applied to a wide range of different chambers, channels, and fluid pathways, and incorporated into a wide range of different ingestible devices. Furthermore, in some embodiments, the overall geometry of FIG. 8 and the positioning of the sponges and the testing area may be altered. For example, the sponge may be formed in the shape of hollow tubes, with testing areas located in the middle of each tube. In this case, there would be a clear optical path from one end of the tube to the other.

Figure 9:
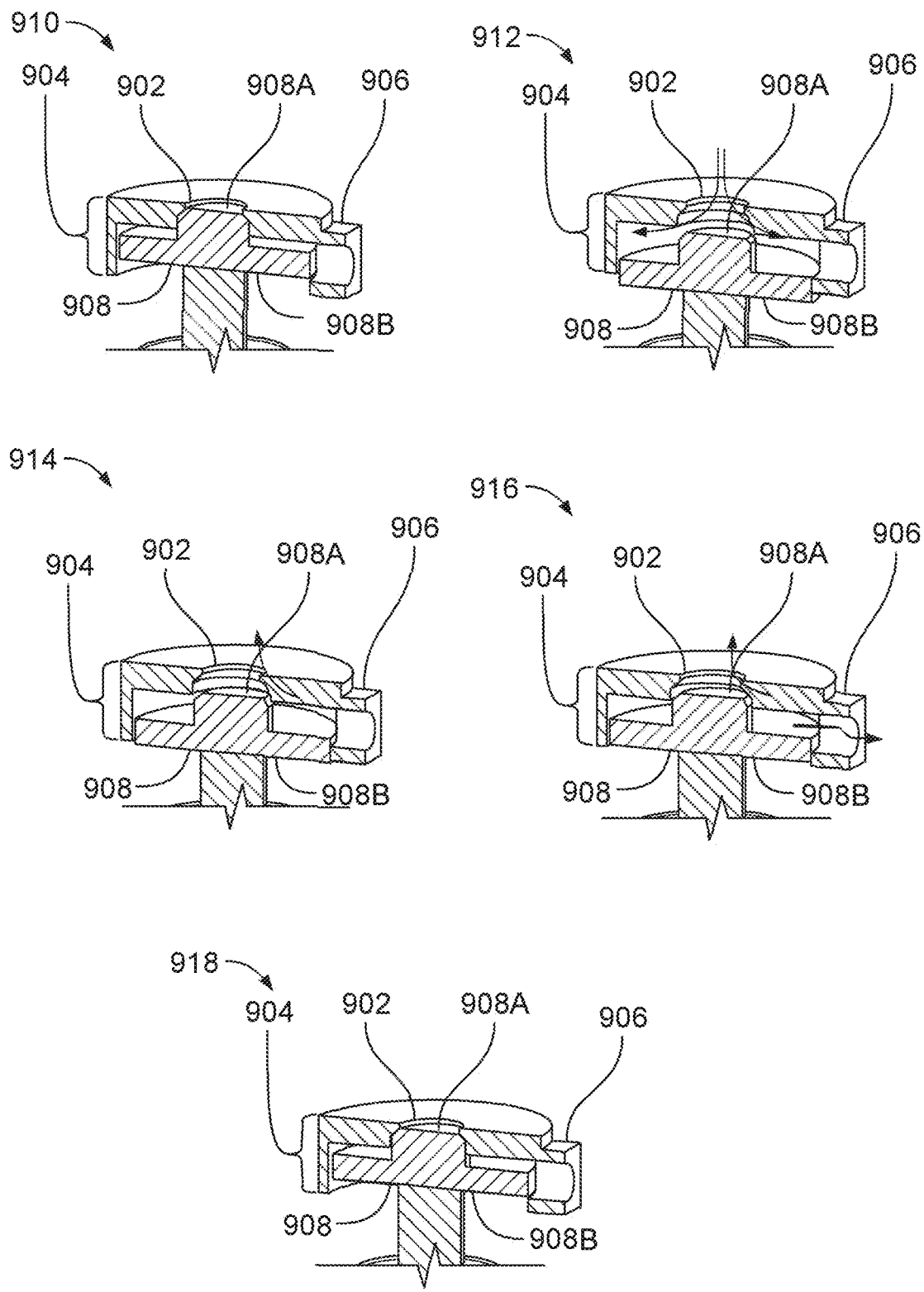
FIG. 9 shows an illustrative pumping mechanism that may be incorporated into an ingestible device.

FIG. 9 illustrates a pumping mechanism 900 that may be incorporated into an ingestible device, including certain embodiments of ingestible devices 100, 200, 600, and 702-706. For illustrative purposes, the pumping mechanism 900 may be described in the context of an ingestible device similar to ingestible device 600 (FIG. 6). When it is incorporated into an ingestible device similar to ingestible device 600, the pumping mechanism 900 may function as a moveable valve (e.g., moveable valve 614 of ingestible device 600), and control the ability of samples to flow between the opening 606 in the housing and the entry port 610 of the sampling chamber 612. Additionally, the pumping chamber 904 of the pumping mechanism 900 may form part of the second portion 608B of the inlet region 608. However, the general structure and principles of pumping mechanism 900 are not limited to the ingestible devices described in this disclosure, and they may be applied to a wide range of ingestible devices.

Pumping mechanism 900 is designed to draw in a sample through a first opening 902 into a pumping chamber 904, and push a portion of the sample out of the pumping chamber 904 through a second opening 906. In some embodiments, the first opening 902 may be connected directly or indirectly to an opening in the housing of an ingestible device. For example, an inlet region (e.g., the first portion 608A of the inlet region 608 of the ingestible device 600 (FIG. 6)) may connect an opening in the housing of an ingestible device (e.g., the opening 606 in the housing of ingestible device 600 (FIG. 6)) to the first opening 902. In some embodiments, the second opening 906 is connected directly or indirectly to a sampling chamber of an ingestible device. For example, the second opening 906 may be connected to an entry port of a sampling chamber (e.g., connected via the third portion 608C of the inlet region 608 to the entry port 610 of the sampling chamber 612 of the ingestible device 600 (FIG. 6)).

The pumping mechanism 900 features a moveable pump head 908 contained within the pumping chamber 904. The protrusion 908A of the moveable pump head 908 is shaped to fit within the first opening 902, or otherwise block the first opening 902. The base 908B of the moveable pump head 908 is able to cover the second opening 906 or otherwise block the second opening 906. Moreover, the protrusion 908A and the base 908B of the moveable pump head 908 are sized and oriented from each other in such a manner such that when the protrusion 908A blocks the first opening 902, the base 908B may simultaneously block the second opening 906 or leave the second opening 906 unblocked. Furthermore, when the base 908B blocks the second opening 906, the protrusion 908A may always be configured to also block the first opening 902.

As the moveable pump head 908 is moved up and down, the openings 902 and 906 may be sealed or unsealed, switching the pumping mechanism 900 across an open position, a partially closed position, and a closed position. In the open position (as is shown in the diagram 912), both the first opening 902 and the second opening 906 are unsealed or open. In the partially closed position (as is shown in the diagram 914, the moveable pump head 908 is positioned to only seal the first opening 902, while leaving the second opening 906 open. Finally, in the closed position (as is shown in the diagrams 910 and 918), both the first opening 902 and the second opening 906 are sealed.

In some embodiments, the moveable pump head 908 may be connected to a mechanical actuator (e.g., the mechanical actuator 624 of the ingestible device 600 (FIG. 6)), which may be configured to move the moveable pump head 908 linearly up and down. For example, the moveable pump head 908 may be located on the end of a shaft that is attached to the mechanical actuator. In some embodiments, the mechanical actuator and the positioning of the moveable pump head 908 may be controlled by a microcontroller or microprocessor located within the ingestible device. For example, a microcontroller may be configured to move the pump head 908 and begin pumping a sample through the pumping chamber 904 only after the ingestible device has reached a particular location within the GI tract.

Diagram 910 depicts the pumping mechanism 900 in a fully closed position. When the pumping mechanism 900 is in the fully closed position, the protrusion 908A of the moveable pump head 908 may be positioned within the first opening 902, and the base 908B of the moveable pump head 908 may be positioned adjacent to the second opening 906. In the fully closed position, the positioning of the moveable pump head 908 may effectively prevent a sample from entering or exiting the pumping chamber 904 from the openings 902 or 906.

Diagram 912 depicts the pumping mechanism 900 in an open position. When the pumping mechanism 900 is in the open position, the moveable pump head 908 is moved away from the first opening 902, moving the protrusion 908A of the moveable pump head 908 out of the first opening 902, and moving the base 908B of the moveable pump away from the second opening 906. In this position, the pumping mechanism 900 may allow one or more samples to enter the pumping chamber 904 through the first opening 902, and exit the pumping chamber 904 through the second opening 906. Because the effective volume of the pumping chamber 904 increases when the moveable pump head 908 is moved away from the first opening 902, the pumping mechanism 900 may draw a sample into the sampling chamber through the first opening 902 when transitioning from a closed position depicted in the diagram 910 to an open position depicted in the diagram 912. In some embodiments, a one-way valve may be incorporated into an ingestible device to prevent samples from being drawn into the pumping chamber 904 through the second opening 906 when the pumping mechanism 900 transitions between the closed position and the open position. This may ensure that the only sample entering the pumping chamber 904 is drawn in through the first opening 902.

Diagram 914 depicts the pumping mechanism 900 in a partially closed position. When the pumping mechanism 900 is in the partially closed position, the protrusion 908A of the moveable pump head 908 is positioned adjacent to the first opening 902, or just inside the first opening 902. In this position, the protrusion 908A of the moveable pump head 908 effectively seals off the first opening 902, preventing any of the sample remaining in the pumping chamber 904 from exiting pumping chamber 904 via the first opening 902. In this position, the base 908B of the moveable pump head 908 is positioned away from the second opening 906. This may allow any sample remaining in the pumping chamber 904 to exit the pumping chamber 904 through the second opening 906. For example, if the second opening 906 is connected to an entry port of a sampling chamber (e.g., connected via the third portion 608C of the inlet region 608 to the entry port 610 of the sampling chamber 612 of the ingestible device 600 (FIG. 6)), this may allow the sample to flow freely from the pumping mechanism 900 into the sampling chamber via the entry port.

Diagram 916 depicts the pumping mechanism 900 as it transitions between the partially closed position to the fully closed position. As the pumping mechanism 900 moves into the fully closed position, the moveable pump head 908 forces any of remaining sample contained within the pumping chamber 904 out of the pumping chamber 904 through the second opening 906. As this happens, the protrusion 908A of the moveable pump head 908 remains within the first opening 902, blocking it off and preventing the sample from exiting the pumping chamber 904 through first opening 902. By comparison, the base 908B of the moveable pump head 908 does not fully cover the second opening 906, and the sample is free to exit the pumping chamber 904 through the second opening 906. In combination, this may result in a majority of the sample remaining in the sampling chamber being forced through the second opening 906 as the pumping mechanism 900 moves from the partially closed position depicted in diagram 914 to the fully closed position depicted in diagram 918.

Diagram 918 depicts the pumping mechanism 900 in the fully closed position, similar to diagram 910. As noted before, in the fully closed position the moveable pump head 908 is positioned to seal off the openings 902 and 906, which may prevent a sample from entering or exiting the pumping chamber 904 from the openings 902 or 904. In general, the pumping mechanism 900 may cycle between the closed position depicted in diagrams 910 and 918 and the open position depicted in diagram 912 any number of times in order to draw additional samples into the pumping chamber 904 through the first opening 902, and force the samples out of the pumping chamber 904 through the second opening 906.

Although FIG. 9 depicts the protrusion 908A of the moveable pump head 908 located in the center of the moveable pump head 908, the location of the protrusion 908A may be anywhere on the moveable pump head 908. For example, the protrusion 908A of the moveable pump head 908 and the first opening 902 may be positioned on the side of the pumping chamber 904. In some embodiments, the moveable pump head 908 is split into two pieces, which may be controlled by one or more actuators. For example, the protrusion 908A and the base 908B may be two separate pieces, each of which is moved using a different actuator. This may allow the first opening 902 to be sealed and unsealed independently from the volume of the pumping mechanism 900 being increased or decreased.

For illustrative purposes, the diagrams 910-918 depict the base 908B of the moveable pump head 908 being used to cover or otherwise block the second opening 906. However, in some embodiments, the moveable pump head 908 may not cover, fit within, or otherwise block the second opening 906, and it will be understood by one skilled in the art that the second opening 906 does not need to be partially or fully blocked in order to push a sample through the second opening 906. For example, the moveable pump head 908 may not include a base 908B at all. Instead, the moveable pump head 908 may be made of a flexible material that forms a seal with the underside of the pumping chamber 904. In this case, the moveable pump head 908 may be moved up and down in a manner similar to a plunger in order to change the effective volume of the pumping chamber 904. When the volume decreases, the sample is at least partially forced out of the pumping chamber 904 through the second opening 906.

In general, incorporating the pumping mechanism 900 into an ingestible device may not impair the function of the openings, ports, valves, membranes, sampling chambers, or other structures of the ingestible device, and any of the teachings or embodiments described in conjunction with the ingestible devices 100, 200, 600, or 702-706 may be combined in different embodiments of an ingestible device along with the pumping mechanism 900. For example, the pumping mechanism 900 may replace the first valve 214 in the ingestible device 200 (FIG. 2), and may be used to force the sample into the sampling chamber 212. As an alternate example, the pumping mechanism 900 may be used to force samples into the sampling chamber 304 of the osmotic valve mechanism 300 (FIG. 3). As another example, the pumping mechanism 900 may be incorporated into an embodiment of the ingestible device 600 (FIG. 6) where the exit port 616 is not included, and the pumping mechanism 900 may be used to force the sample into the sampling chamber 612 despite the pressure that may result from air or gas 618 being trapped within the sampling chamber 612.

Figure 10:
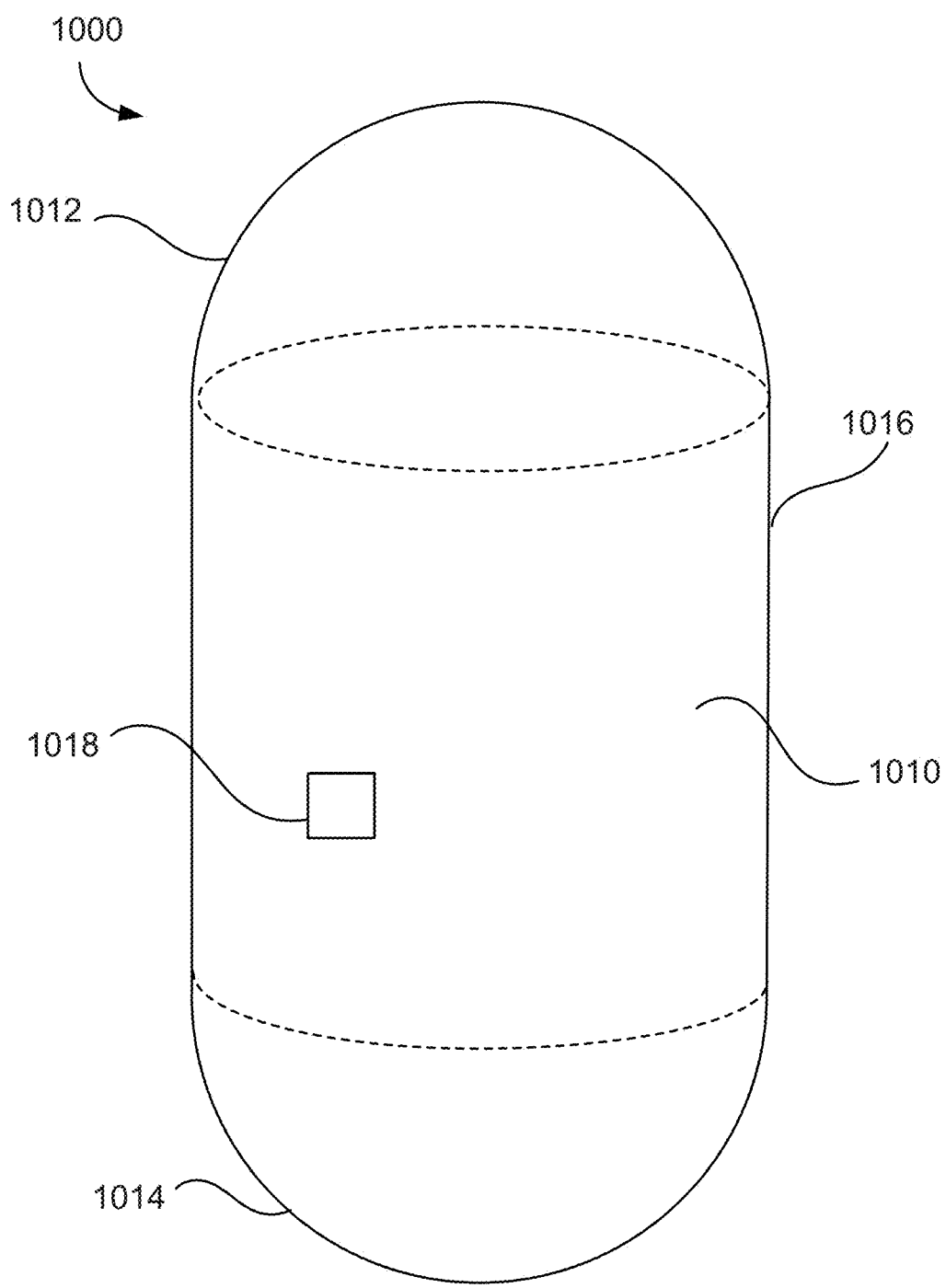
FIG. 10 shows a highly schematic representation of an ingestible device.

FIG. 10 illustrates, in a highly schematic fashion, an ingestible device 1000 having a housing 1010 that includes a first end 1012 and a second end 1014 opposite first end 1012. Housing 1010 also includes a wall 1016 that connects first end 1012 and second end 1014. Wall 1016 has an opening 1018 that allows fluid from an exterior of the ingestible device 1000 (e.g., from the GI tract) and into an interior of ingestible device 1000.

Figure 11:
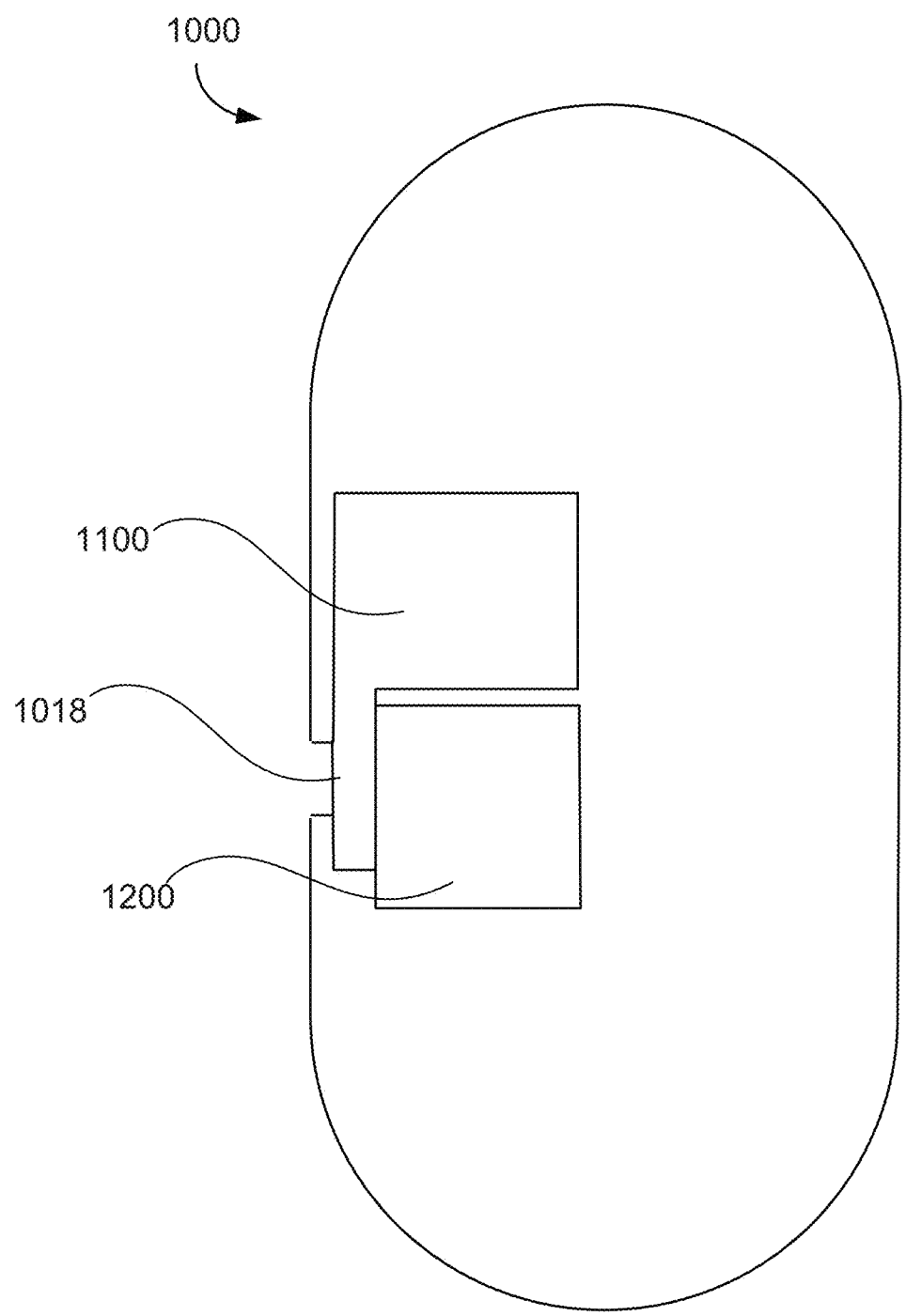
FIG. 11 shows a highly cross-section of an ingestible device including a valve system and a sampling system.

FIG. 11 depicts a cross-sectional view of a portion of the interior of ingestible device 1000. As shown in FIG. 11, the interior of ingestible device 1000 includes a valve system 1100 and a sampling system 1200. Valve system 1100 is depicted as having a portion that is flush with the opening 1018 so that valve system 1100 prevents fluid exterior to ingestible device 1000 from entering sampling system 1200. However, as described in more detail below with reference to FIGS. 12-16, valve system 1100 can change position so that valve system 1100 allows fluid exterior to ingestible device 1000 to enter sampling system 1200.

Figure 16:
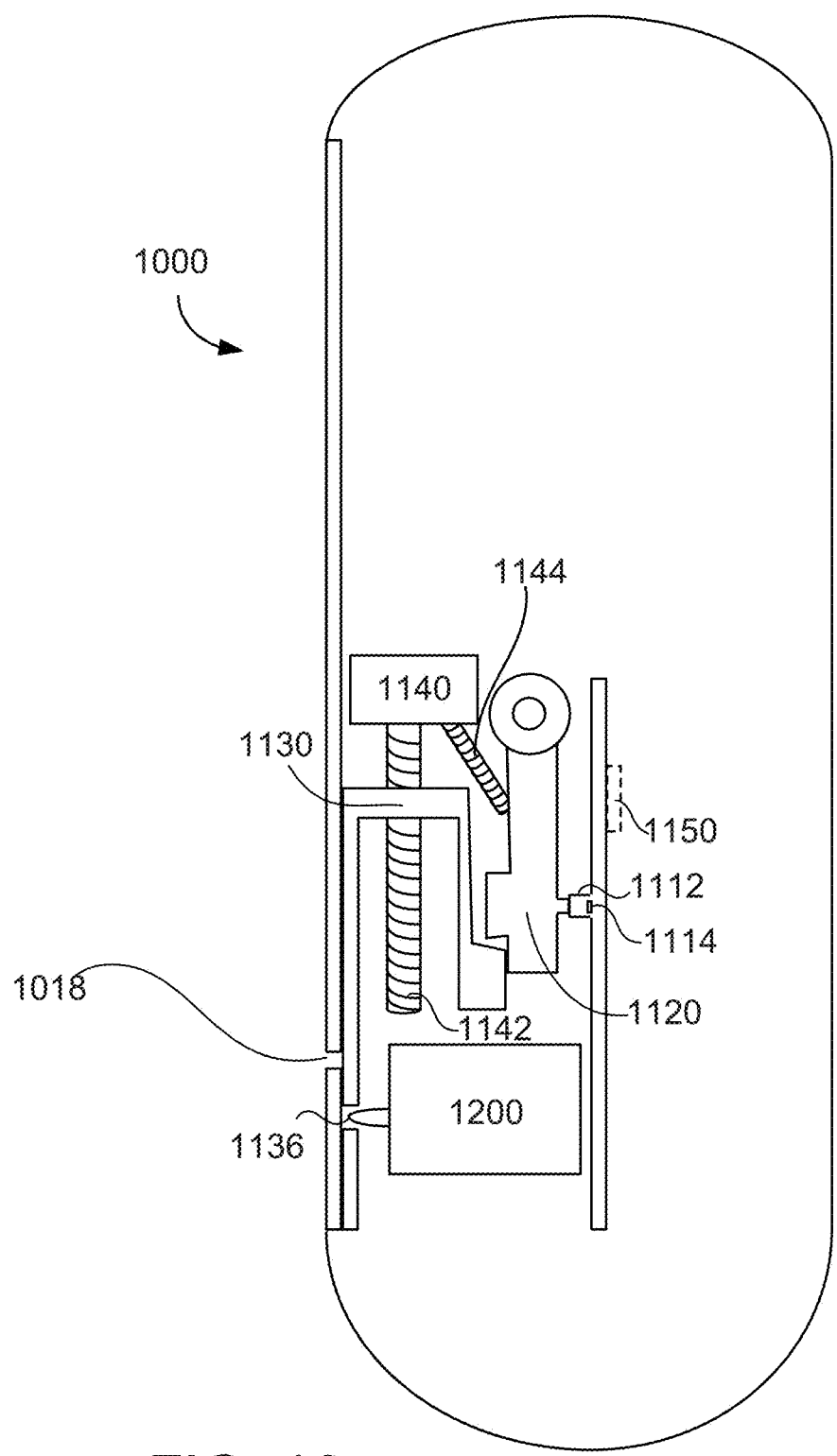
FIG. 16 illustrates a more detailed view of an ingestible device including a valve system and a sampling system.

FIGS. 12 and 16 illustrate valve system 1100 in more detail. As shown in FIG. 12, valve system 1100 includes an actuation mechanism 1110, a trigger 1120, and a gate 1130. In FIGS. 12 and 16, a leg 1132 of gate 1130 is flush against, and parallel with, housing wall 1016 so that gate leg 1132 covers opening 1018 to prevent fluid exterior to ingestible device 1000 (e.g., fluid in the GI tract) from entering the interior of ingestible device 1000. A protrusion 1134 of gate 1130 engages a lip 1122 of trigger 1120. A peg 1124 of trigger 1120 engages a wax pot 1112 of actuation mechanism 1110. Referring to FIG. 16, a biasing mechanism 1140 includes a compression spring 1142 that applies an upward force on gate 1130. Biasing mechanism 1140 also includes a torsion spring 1144 that applies a force on trigger 1120 in the counter-clockwise direction. In FIGS. 12 and 16, the force applied by torsion spring 1144 is counter-acted by the solid wax in pot 1112, and the force applied by compression spring 1142 is counter-acted by lip 1122.

FIG. 13A and FIG. 13B show an embodiment of the manner in which actuation mechanism 1110 actuates movement of trigger 1120. Similar to FIGS. 12 and 16, FIG. 13A shows a configuration in which peg 1124 applies a force against solid wax pot 1112 due to torsion spring 1144, and in which the solid nature of wax pot 1112 resists the force applied by peg 1124. A control unit 1150 is in signal communication with valve system 1100. During use of ingestible device 1000, a control unit 1150 receives a signal, indicating that the position of valve system 1100 should change, e.g., so that ingestible device 1000 can take a sample of a fluid in the GI tract. Control unit 1150 sends a signal that causes a heating system 1114 of actuation system 1100 to heat the wax in pot 1112 so that the wax melts. As shown in FIG. 13B, the melted wax is not able to resist the force applied by peg 1124 so that, under the force of torsion spring 1144, trigger 1120 moves in a counter-clockwise fashion.

Figures 14A, 14B:
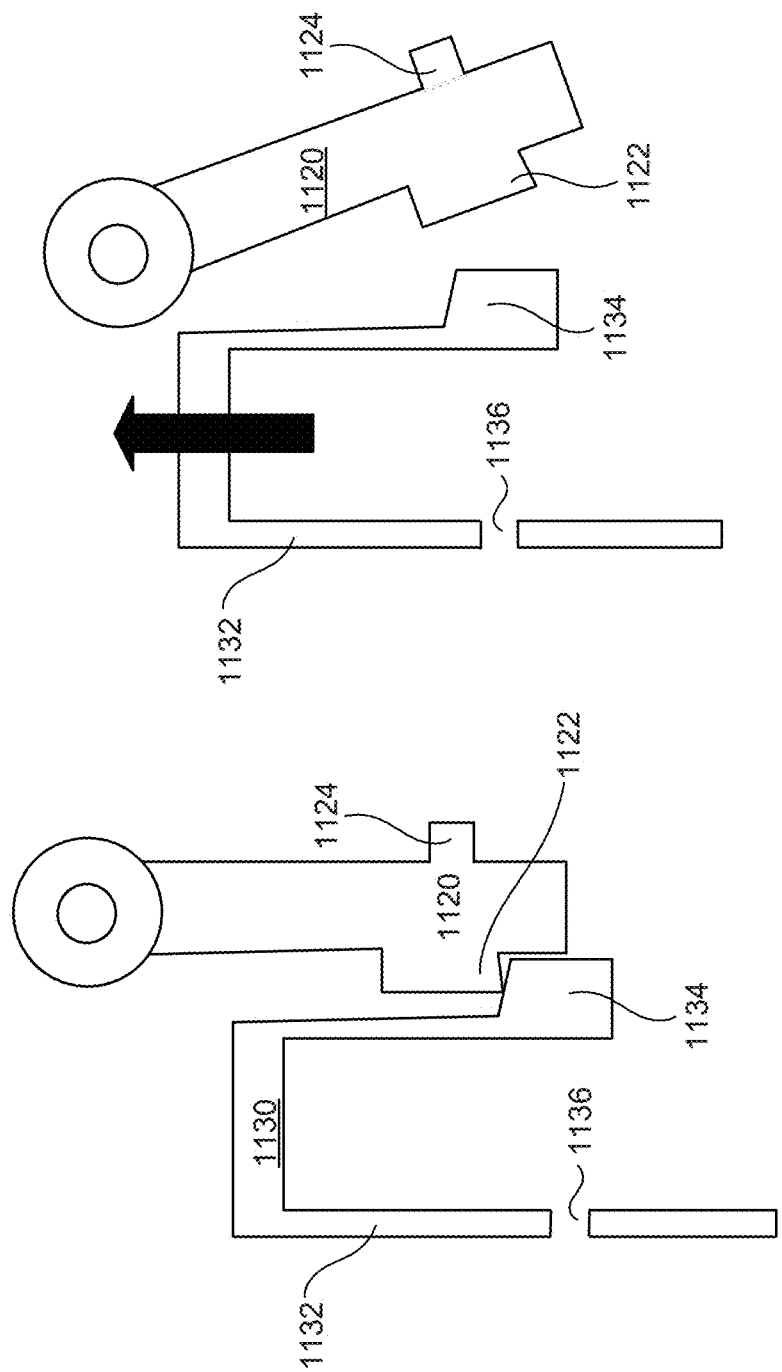
FIGS. 14A and 14B illustrate a portion of a two-stage valve system in its first and second stages, respectively.

FIGS. 14A and 14B illustrate the interaction of trigger 1120 and gate 1130 before and after actuation. As shown in FIG. 14A, when wax pot 1302 is solid (corresponding to the configuration shown in FIG. 13A), protrusion 1134 engages lip 1122, which prevents the force of compression spring 1142 from moving gate 1130 upward. As shown in FIG. 14B, when the wax in pot 1112 melts (FIG. 13B), trigger 1120 moves counter-clockwise, and lip 1122 disengages from protrusion 1134. This allows the force of compression spring 1142 to move gate 1130 upward. As seen by comparing FIG. 14A to FIG. 14B, the upward movement of gate 1130 results in an upward movement of an opening 1136 in gate leg 1132.

FIGS. 15A and 15B illustrate the impact of the upward movement of opening 1136 on the ability of ingestible device 1000 to obtain a sample. As shown in FIG. 15A, when the wax in pot 1112 is solid (FIGS. 13A and 14A), opening 1136 in is not aligned with opening 1018 in wall 1016 of ingestible device 1000. Instead, gate leg 1132 covers opening 1018 and blocks fluid from entering the interior of ingestible device 1000. As shown in FIG. 15B, when the wax in pot 1112 is melted and trigger 1120 and gate 1130 have moved (FIGS. 13B and 14B), opening 1136 in gate 1130 is aligned with opening 1018 in wall 1016. In this configuration, fluid that is exterior to ingestible device 1000 (e.g., in the GI tract) can enter the interior of ingestible device 1000 via openings 1018 and 1036.

Figure 17A:
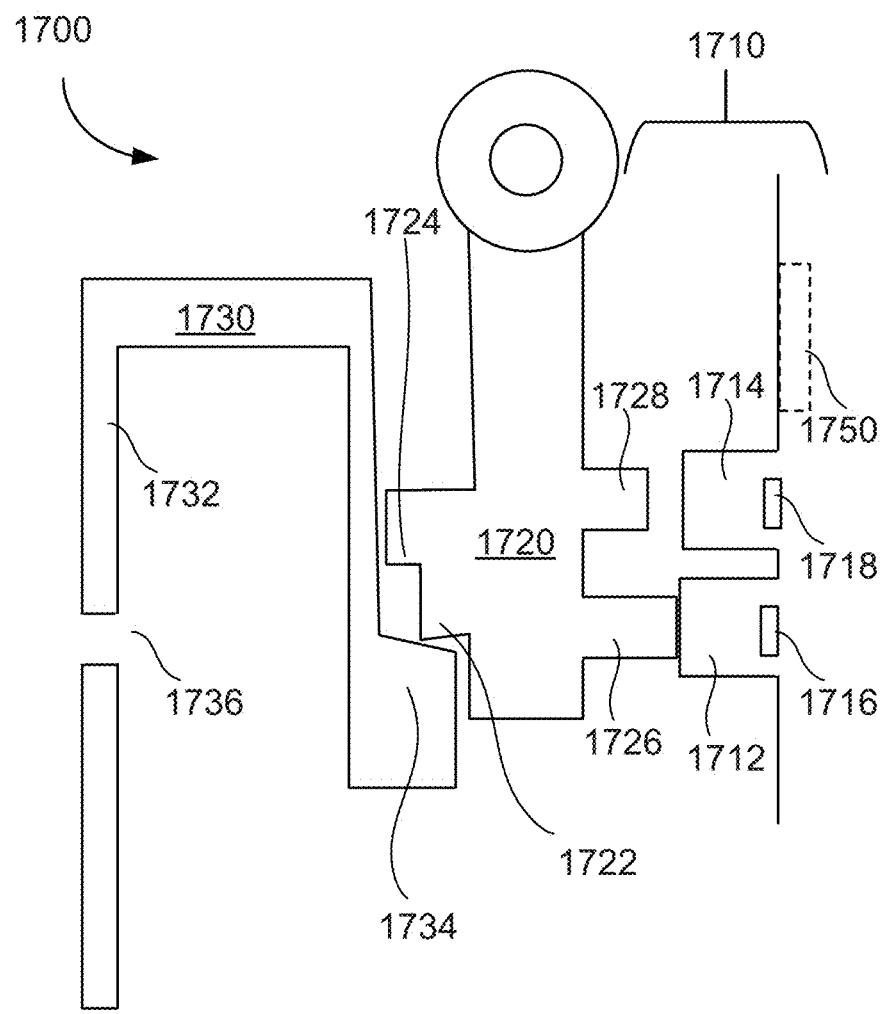
FIGS. 17A-17C illustrate a portion of a three-stage valve system in its first, second and third stages, respectively.
Figure 17C:
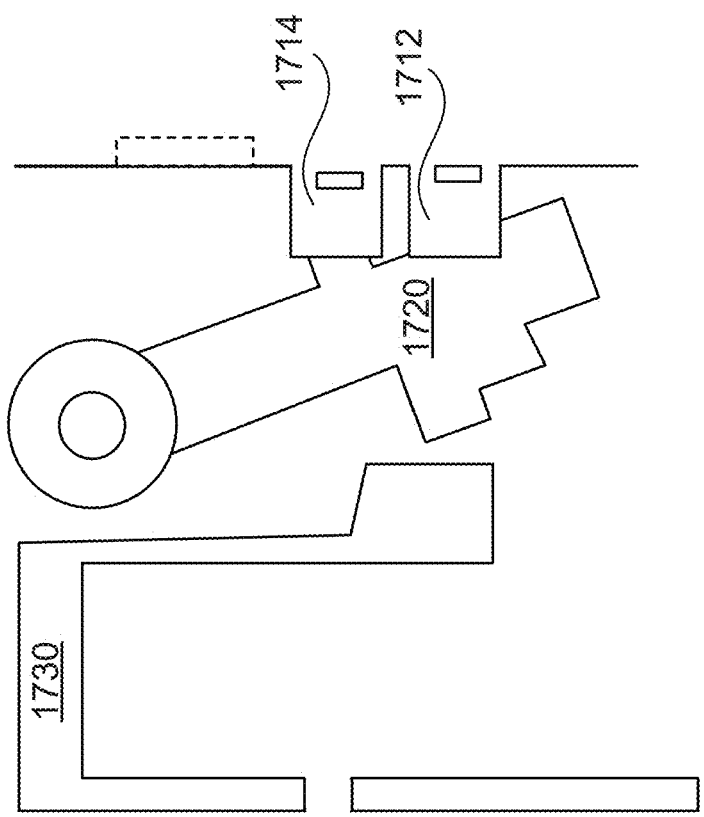
Figure 17B:
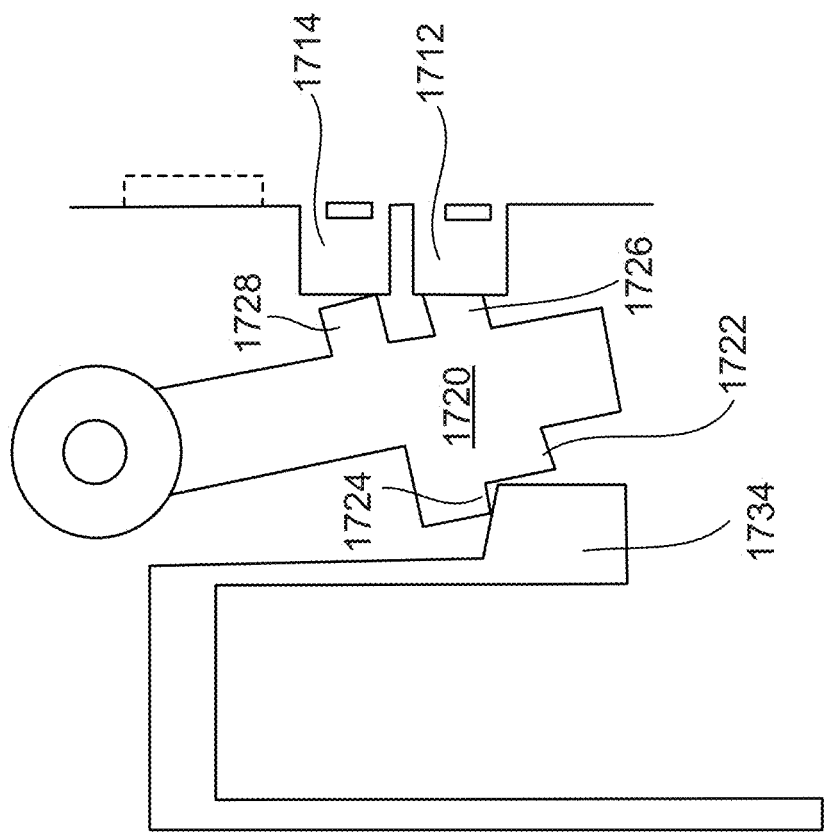
Figure 18C:
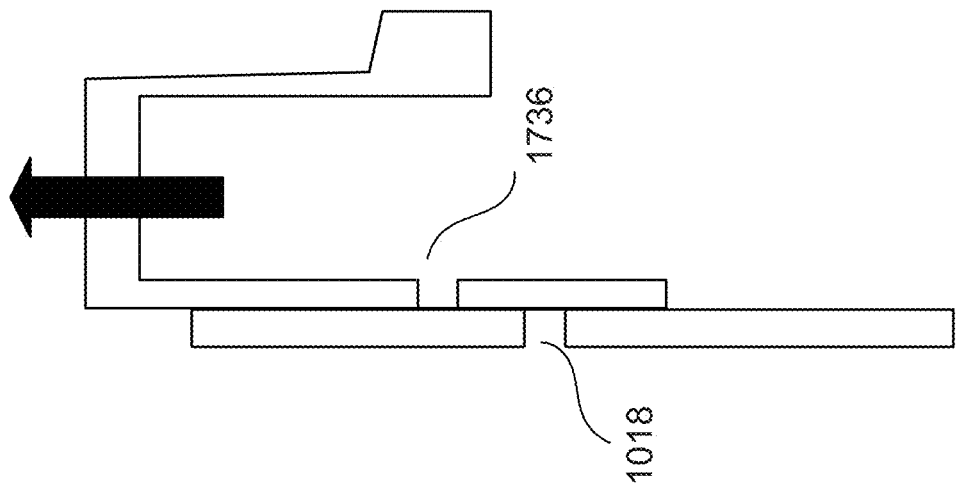
FIGS. 18A-18C illustrate a portion of a three-stage valve system in its first, second and third stages, respectively.
Figure 18B:
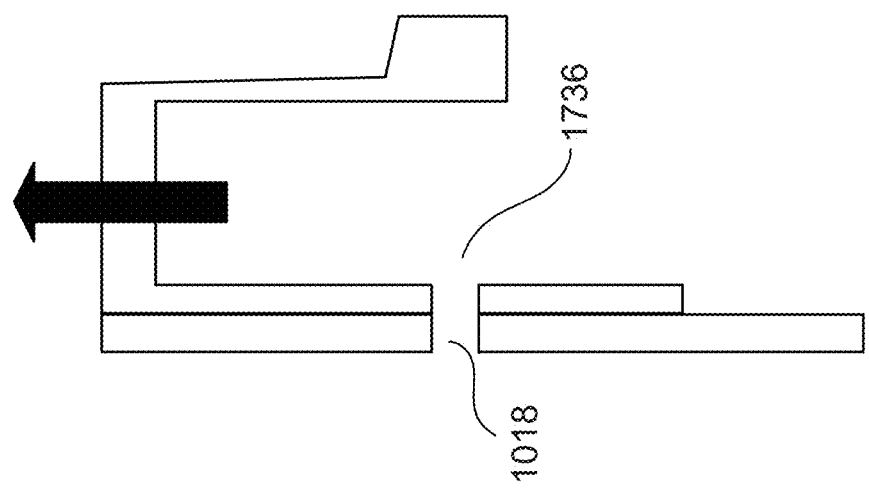
Figure 18A:
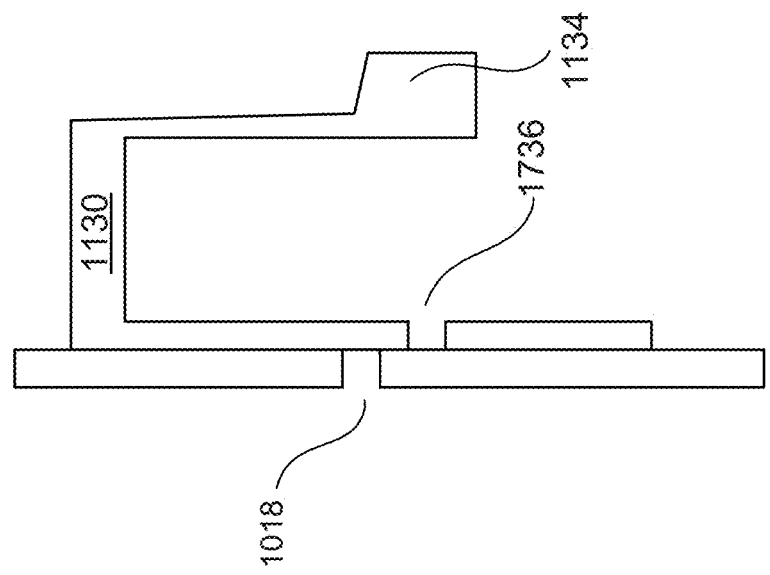
Figure 19A:
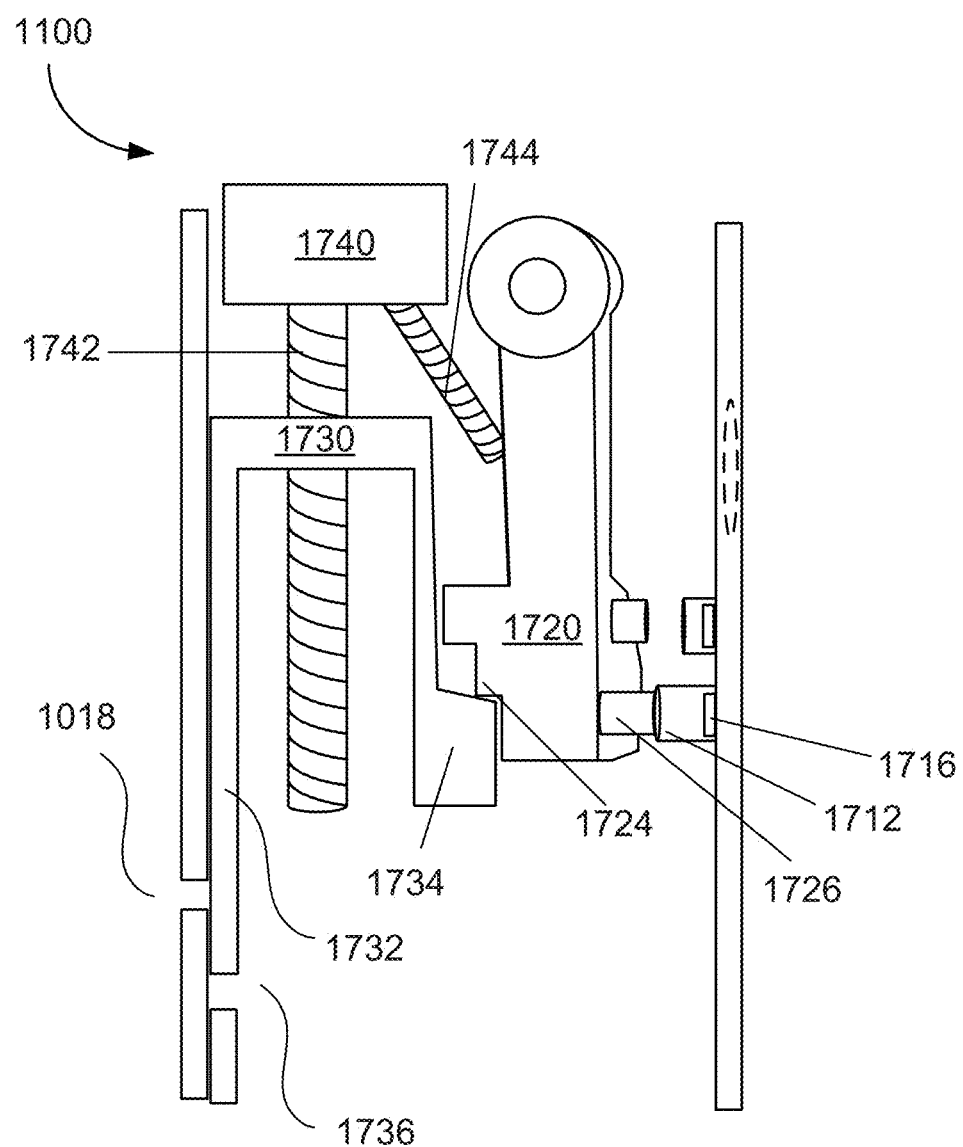
FIGS. 19A-19C illustrate a portion of a three-stage valve system in its first, second and third stages, respectively.
Figure 19B:
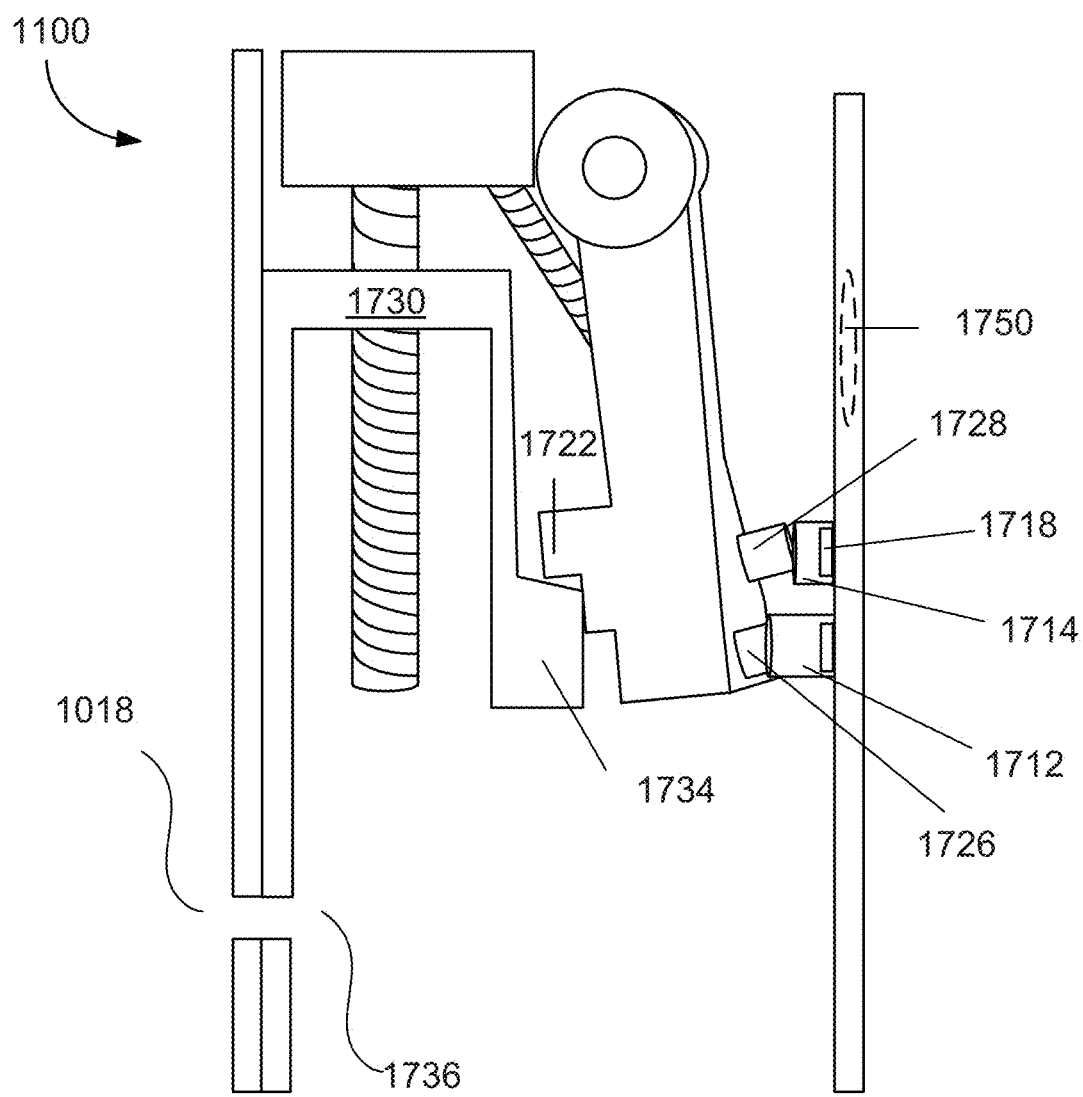
Figure 19C:
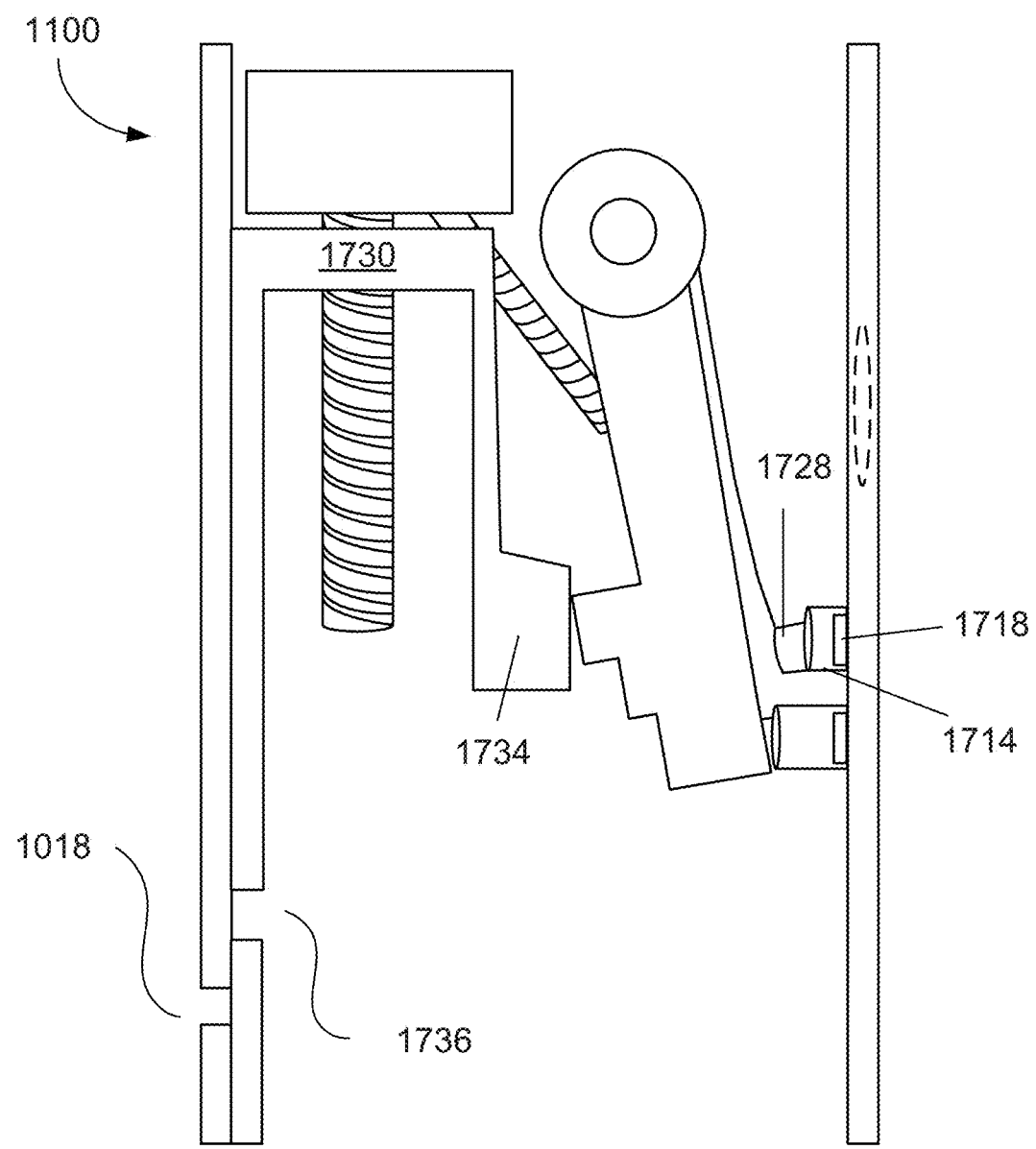

While the foregoing description is made with regard to a valve system having one open position and one closed position (e.g., a two-stage valve system), the disclosure is not limited in this sense. Rather, the concepts described above with regard to a two stage valve system can be implemented with a valve system have more than two stages (e.g., three stages, four stages, five stages, etc.). For example, FIGS. 17A-19C illustrate cross-sectional views of a three-stage valve system 1700. FIGS. 17A, 18A and 19A illustrate different views of components of valve system 1700 in the same position. FIGS. 17B, 18B and 19B illustrate different views of components of valve system 1700 in the same position. FIGS. 17C, 18C and 19C illustrate different views of components of valve system 1700 in the same position.

As shown in FIGS. 17A-19C, valve system 1700 includes an actuation system 1710, a trigger 1720, a gate 1730 and a biasing system 1740. Actuation system 1710 includes a first wax pot 1712, a second wax pot 1714, a first heating system 1716 and a second heating system 1718. Trigger 1720 includes a first lip 1722, a second lip 1724, a first peg 1726 and a second peg 1728. Gate 1730 includes a gate leg 1732 and a protrusion 1734. Gate leg 1732 has an opening 1736. Biasing system 1740 includes a compression spring 1742 and a torsion spring 1744. In addition, the ingestible device includes a control unit 1750.

As shown in FIGS. 17A, 18A and 19A, in the first stage, protrusion 1734 engages first lip 1722, and first peg 1726 engages first wax pot 1712. Compression spring 1742 applies an upward force on gate 1730, and torsion spring 1744 applies a force on trigger 1720 in the counter-clockwise direction. The force applied by torsion spring 1744 is counter-acted by the solid wax in first pot 1712, and the force applied by compression spring 1742 is counter-acted by first lip 1722. Opening 1736 is not aligned with opening 1018.

FIGS. 17B, 18B and 19B illustrate the configuration in a second stage, after control unit 1750 sends a signal to first heating system 1716 to melt the wax in first pot 1712. In the second stage, trigger 1720 has moved counter-clockwise relative to its position in the first stage. First peg 1726 is positioned in first pot 1712 because the melted wax cannot prevent this movement. Further counter-clockwise movement of trigger 1720 is prevented by the engagement of second peg 1728 with the solid wax in second pot 1714. With the counter-clockwise movement of trigger 1720, first lip 1722 disengages from protrusion 1734, and gate 1730 moves upward so that opening 1736 in leg 1732 is aligned with opening 1018. Further upward movement of gate 1730 is prevented by the engagement of protrusion 1734 with second lip 1724.

FIGS. 17C, 18C and 19C illustrate the configuration in a third stage, after control unit 1750 sends a signal to second heating system 1718 to melt the wax in second pot 1714. In the third stage, trigger 1720 has moved counter-clockwise relative to its position in the second stage. Second peg 1728 is positioned in second pot 1714 because the melted wax cannot prevent this movement. Further counter-clockwise rotation is prevented by the engagement of first and second pegs 1726 and 1728, respectively with first and second pots 1712 and 1714, respectively. Protrusion 1734 is disengaged from second lip 1724, allowing the force of compression spring 1742 to move gate 1730 upward so that opening 1736 is no longer aligned with opening 1018.

Figure 20:
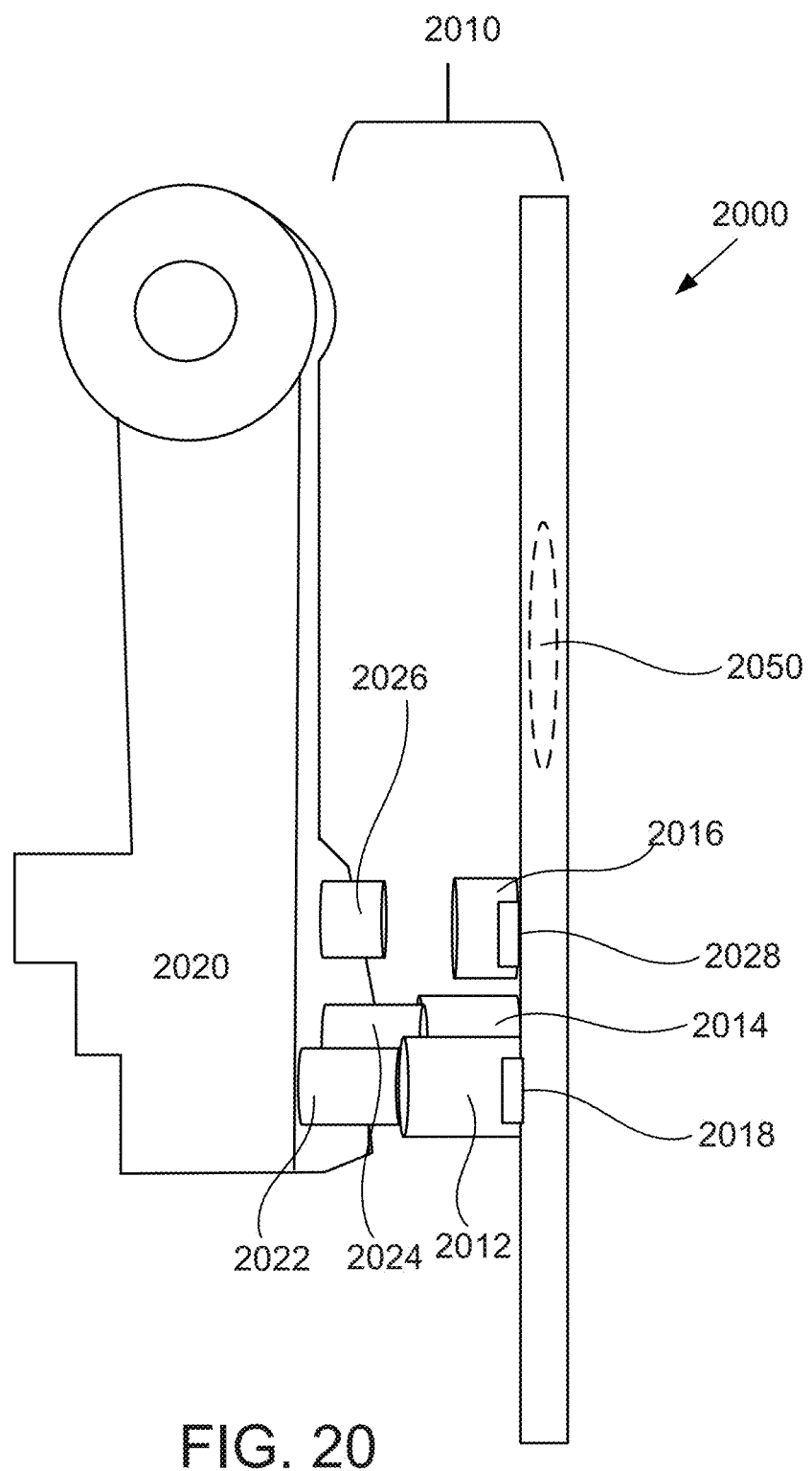
FIG. 20 illustrates a three-stage valve system in its first stage.

FIG. 20 illustrates another embodiment of a three stage valve system 2000 that can be used in an ingestible device. Valve system 2000 that is similar to valve system 1700 except that actuation system 2010 includes three includes wax pots 2012, 2014 and 2016, respectively, that define a triangle, and trigger 2020 includes three pegs 2022, 2024 and 2026, respectively, that define a corresponding triangle. Actuation system 2010 is controlled using a control unit 2050. Actuation system 2010 also includes a first heating system 2018 that heats the wax in pots 2012 and 2014 and so that pegs 2022 and 2024 enters their corresponding pot, causing valve system 2000 to move from its first stage to its second stage. Actuation system 2010 also includes a second heating system 2028 that heats the wax in pot 2016 so that pegs 2026 enters pot 2016, causing valve system 2000 to move from its second stage to its third stage.

In the foregoing discussion, embodiments actuating systems are described that include one or more wax pots and corresponding heating systems. But the disclosure is not limited to such actuating systems. Generally, any actuating system can be used that will provide an appropriate force to resist counter-clockwise movement of the trigger when desired and to remove that force when desired. Examples of such actuation systems include a pot with a silicon or wax seal. A control unit may be used to rupture the seal and allow counter clock-wise movement of the trigger. Additionally, or alternatively, the actuation mechanism may use dissolvable coating to that dissolves over time or in the presence of a substance. As the coating dissolves, the trigger may move further in the counter clock-wise direction. Other actuation mechanisms may also apply an attractive force rather than remove a resistive force. For example, the actuation mechanism may include magnetic pegs and slidable magnets The magnets may be located behind the pots or may slide to a position behind the pots when the valve system should change stages. As the magnets behind the pots slide into range of the magnetic trigger pegs, the trigger moves in the counterclockwise direction due to the attractive force between the magnetic peg and the magnets. The sliding mechanism to move the slidable magnets may be powered by an osmotic pump, a pressurized chamber, or any other applicable method of movement previously described in other embodiments.

In the discussion above, embodiments of triggers are disclosed that include one or more lips and one or more pegs. However, the disclosure is not limited to such triggers. In general, for example, any trigger design can be used that is capable of providing the step-wise movement of the trigger. Such trigger designs include, for example, a releasable latch coupling or a saw toothed engagement wall. A different embodiment may utilize a ball in socket joint to engage the trigger and gate, in which the "socket" is located on the trigger. It is to be noted that such designs need not be based on counter-clockwise movement and may be, for example, designed for the controlled movement of the trigger in one or more of various degrees of freedom. For example, rather than rotate, the trigger may be configured to slide laterally to push a peg of the trigger into a melted wax pot.

The discussion above describes embodiments of gates that include a protrusion and a leg with an opening. The disclosure is not limited to such designs. Generally, any appropriate arrangement can be used so long as it provides the desired step-wise controlled movement of an opening to the interior of the ingestible device. Exemplary designs include a gate that is capable of responding to or applying magnetic forces on the trigger. A saw toothed pattern may also provide a step-wise gate movement. Additionally, embodiments include a latch designed to releasably couple the gate to the trigger. A different embodiment may utilize a ball in socket joint in which the "ball" is located on the gate. Optionally, a gate can include one or regions that include one or more appropriate sealing materials positioned to cover the opening in the housing of the ingestible device when the gate is positioned to prevent fluid exterior to the ingestible device from entering the interior of the device via the opening in the housing of the ingestible device.

In the foregoing discussion, embodiments of biasing systems are described that include a compression spring and a biasing spring. However, the disclosure is not limited in this sense. In general, any biasing elements can be used to provide the counter-clockwise force to the trigger and/or to provide the upward force to the gate. Exemplary biasing elements include elastic bands, wherein a stretched elastic band acts similar to a stretched compression spring as described. Additional basing mechanisms may include magnets and/or magnetic forces to induce trigger or gate movement. For example, a magnet may be located above the gate, where, like the constant force of the stretched compression spring, the magnet also applies a constant attractive force on the gate.

Figure 21A:
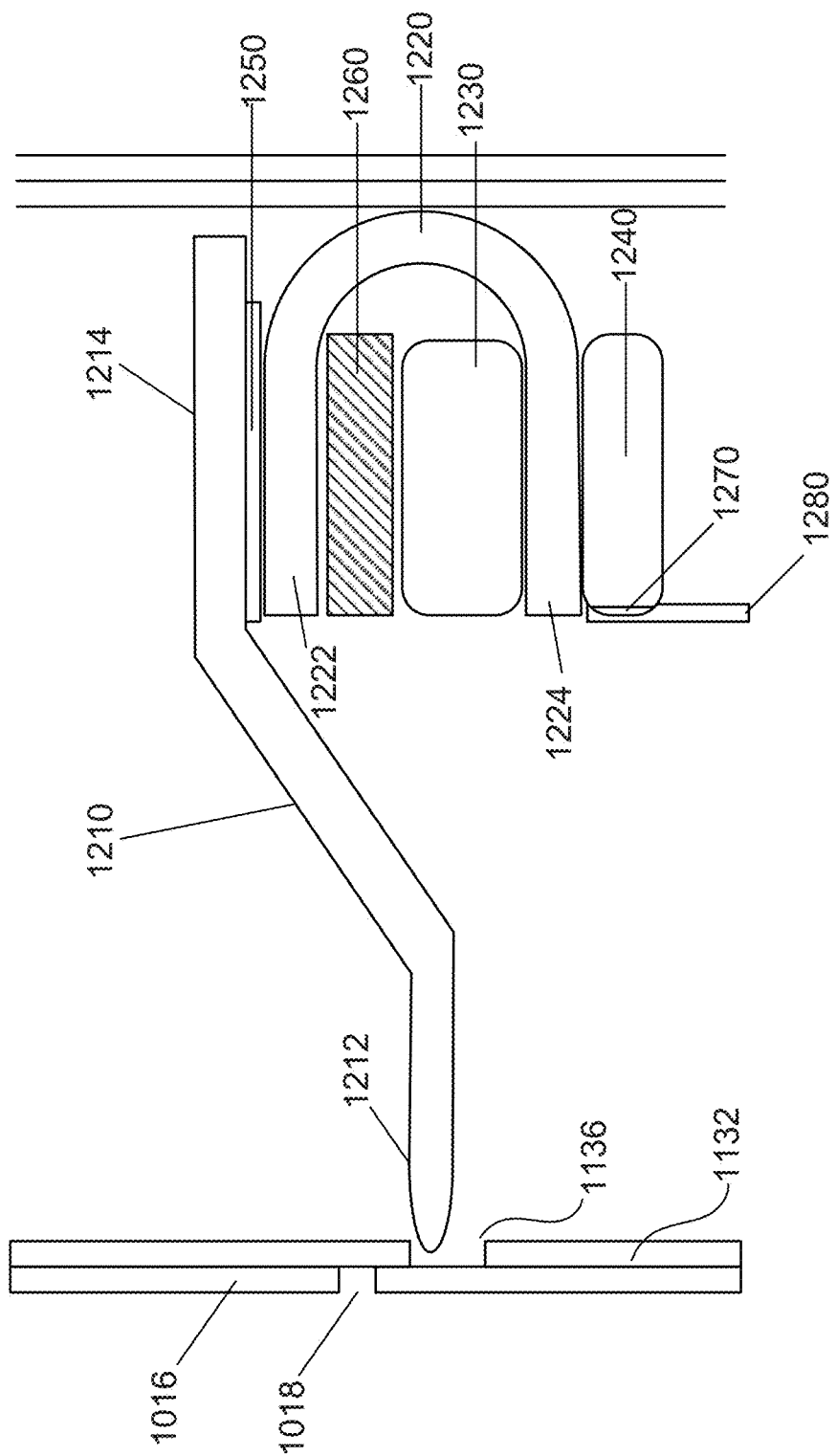
FIG. 21A illustrates a portion of an ingestible device including a sampling system and a two-stage valve system in its first stage.
Figure 21B:
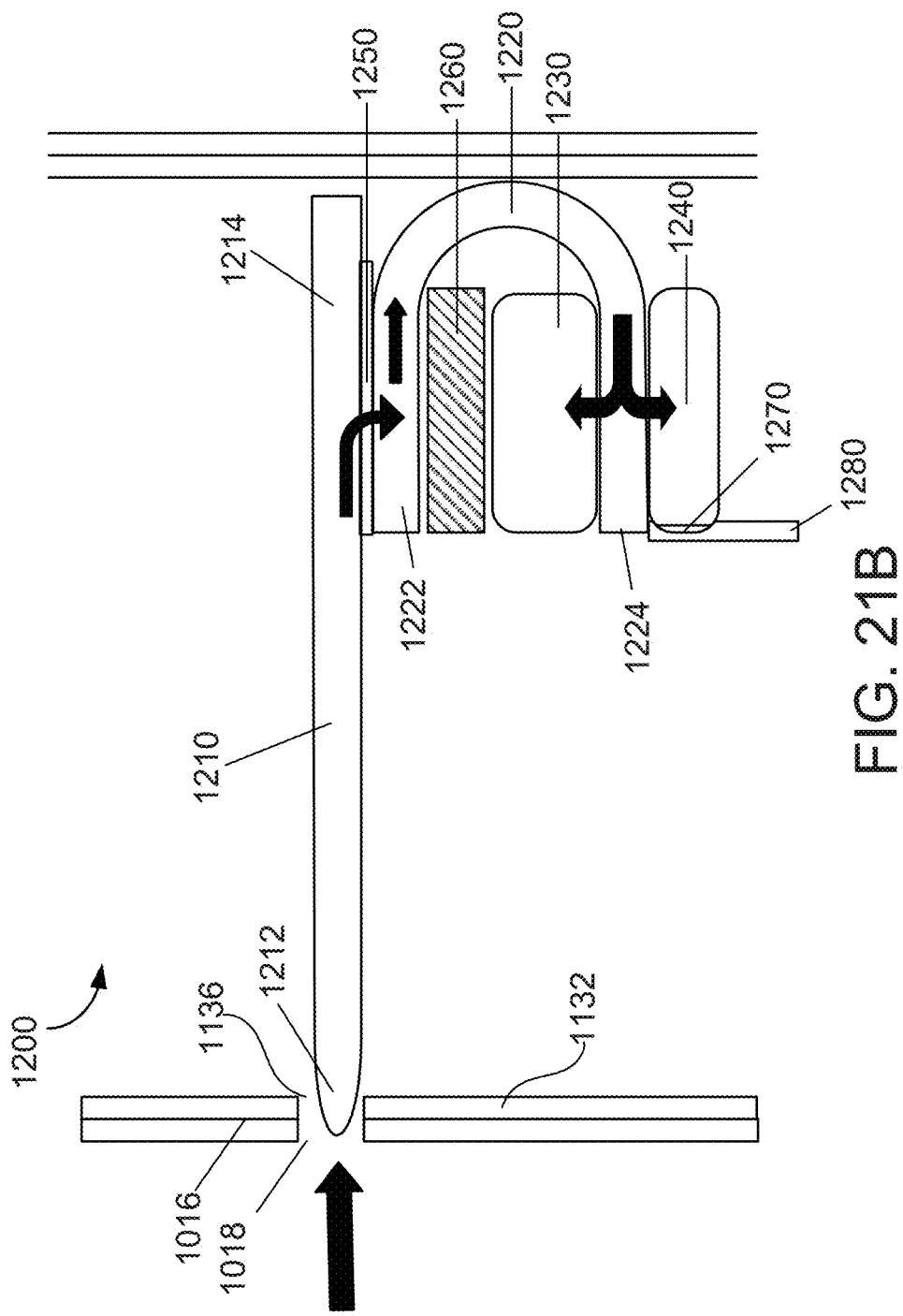
FIG. 21B illustrates a portion of an ingestible device including a sampling system and a two-stage valve system in its second stage.

As noted above in addition to a valve system, an ingestible device includes a sampling system. FIGS. 21A and 21B illustrate a partial cross sectional view of ingestible device 1000 with sampling system 1200 and certain components of valve system 1100. Sampling system 1200 includes a series of sponges configured to absorb fluid from an opening, move the fluid to a location within the housing, and prepare the fluid for testing. Preparation for testing may include filtering the fluid and combining the fluid with a chemical assay. The assay may be configured to dye cells in the filtered sample. The series of sponges includes a wicking sponge 1210, a transfer sponge 1220, a volume sponge 1230, and an assay sponge 1240.

Wicking sponge 1210 absorbs the fluid form the opening in the housing when the valve is open i.e. when the inlet and the housing are aligned. The wicking sponge transfers the fluid from the opening to a filter. Wicking sponge 1210 includes a wicking tongue 1212 extended towards the housing 1016. As shown in FIG. 21A, before actuation of the actuation system (FIGS. 13A, 14A, 15A), wicking tongue 1212 is not adjacent opening 1018 in wall 1016 of ingestible device 1000 so that wicking tongue 1212 does not absorb fluid exterior to ingestible device 1000. However, as shown in FIG. 21B, after actuation of the actuation system (FIGS. 13B, 14B, 15B), wicking tongue 1212 is adjacent opening 1018 so that wicking sponge 1212 absorbs fluid that passes through opening 1018, e.g., fluid from the GI tract. Fluid absorbed by wicking tongue 1212 can travel through wicking sponge 1210 to a distal end 1214 of wicking sponge 1210. The wicking sponge 1210 and wicking tongue 1212 may be made of a VF2 sponge, an Ahlstrom M13 sponge, MF/F material, a Carwild Ivalon Polyvinyl Alcohol material, or another suitable absorptive material. Optionally, the dimensions of the sponge material may be selected to enable all its desired functions while remaining precisely packaged within the capsule. In some embodiments, Carwild Ivalon Polyvinyl Alcohol material is cute to the dimensions 1.4 millimeters (height)×6 millimeters (width)×8.5 millimeters (length). In certain embodiments, one or more of the following parameters can be considered when selecting an appropriate material and/or its dimension: ability to load one more preservative materials; desired preservative material(s) to be loaded; capacity to hold one or more dried preservatives; ability to facilitate hydration of one or more dried preservative materials upon contact with one or more GI fluids; capacity to capture fluid (e.g., GI fluid); and swelling properties upon fluid uptake (generally, it is desirable to have little or no swelling upon fluid uptake).

A cell filter 1250 is located between distal end 1214 of wicking sponge 1210 and a first end 1222 of transfer sponge 1220. The cell filter 1250 is configured to prevent undesired cells, such as Hela cells, from entering one or more downstream sponges in sampling system 1200, particularly sponges used in testing. Excluding such undesired cells enhances the accuracy of various analytical results.

Fluid that passes from wicking sponge 1210 and through cell filter 1250 can enter transfer sponge 1220 via its first end first end 1222. Transfer sponge 1220 is configured to move the filtered fluid from cell filter 1250 to volume sponge 1230 and/or assay sponge 1240.

To allow transfer sponge 1220 to absorb a relatively large volume of fluid, transfer sponge 1220 is shaped (e.g., arc-shaped) to provide a relatively long distance between first end 1222 of transfer sponge 1220 and a second end 1224 of transfer sponge 1220. Second end 1224 contacts both volume sponge 1230 and assay sponge 1240 while preventing volume sponge 1230 and assay sponge 1240 from directly contacting each other. A barrier 1260 is located between first end 1222 and volume sponge 1230 to ensure that fluid absorbed in transfer sponge 1220 at first end 1222 travels to second end 1224 before being absorbed by volume sponge 1230. Although depicted as being arc-shaped, transfer sponge 1220 can have one or more different configurations, such as, for example, an extended straight line or multiple curves, depending, for example, on the desired volume of sample and/or desired transfer speed. In general, the shorter and/or thinner the path of transfer sponge 1220, the quicker the transfer speed from first end 1222 to second end 1224. The transfer sponge 1220 may be made of a VF2 sponge, an Ahlstrom M13 sponge, MF/F material, or another suitable absorptive material.

Volume sponge 1230 absorbs additional fluid for testing and is in fluid communication with assay sponge 1240 via second end 1224 of transfer sponge 1220. Volume sponge 1230 can be particularly useful when fluorescent or optical testing is used. In some embodiments, assay sponge 1240 and transfer sponge 1224 may not individually contain a sufficient volume of the sample to attain a confident test result. The volume of volume sponge 1230, assay sponge 1240, and second end 1224 of the transfer sponge 1220 sum to a sufficient testing volume for optical, and other, tests. Assay sponge 1240 contains a chemical assay that is used to test the sample or to prepare the sample for a test. Once assay sponge 1240 is saturated, the assay chemicals are free to flow from assay sponge 1240 and interact with sample absorbed by transfer sponge 1220 and volume sponge 1230. Volume sponge 1230 and the assay sponge 1240 may be made of a VF2 sponge, an Ahlstrom M13 sponge, MF/F material, or another suitable absorptive material. Preferably, the wicking sponge, wicking tongue, transfer sponge, and assay sponge are Ahlstrom M13 sponges, and the volume sponge is a VF2 sponge.

Cell filter 1250 can be made from any appropriate material and have any appropriate dimensions. Exemplary materials include polycarbonate (PCTE), polyethersulfone (PES), polyester (PETE) and polytetrafluoroethylene (PTFE). In some embodiments, the dimensions of cell filter 1250 can be about 9.5 millimeters by about 6.5 millimeters by about 0.05 millimeter.

Sampling system 1200 also includes a membrane 1270 located between assay sponge 1240 and a vent 1280 for gases to leave sampling system 1200. Membrane 1270 is configured to allow one or more gases to leave sampling system 1200 via an opening 1280, while maintaining liquid in sampling system 1200.

Figure 22:
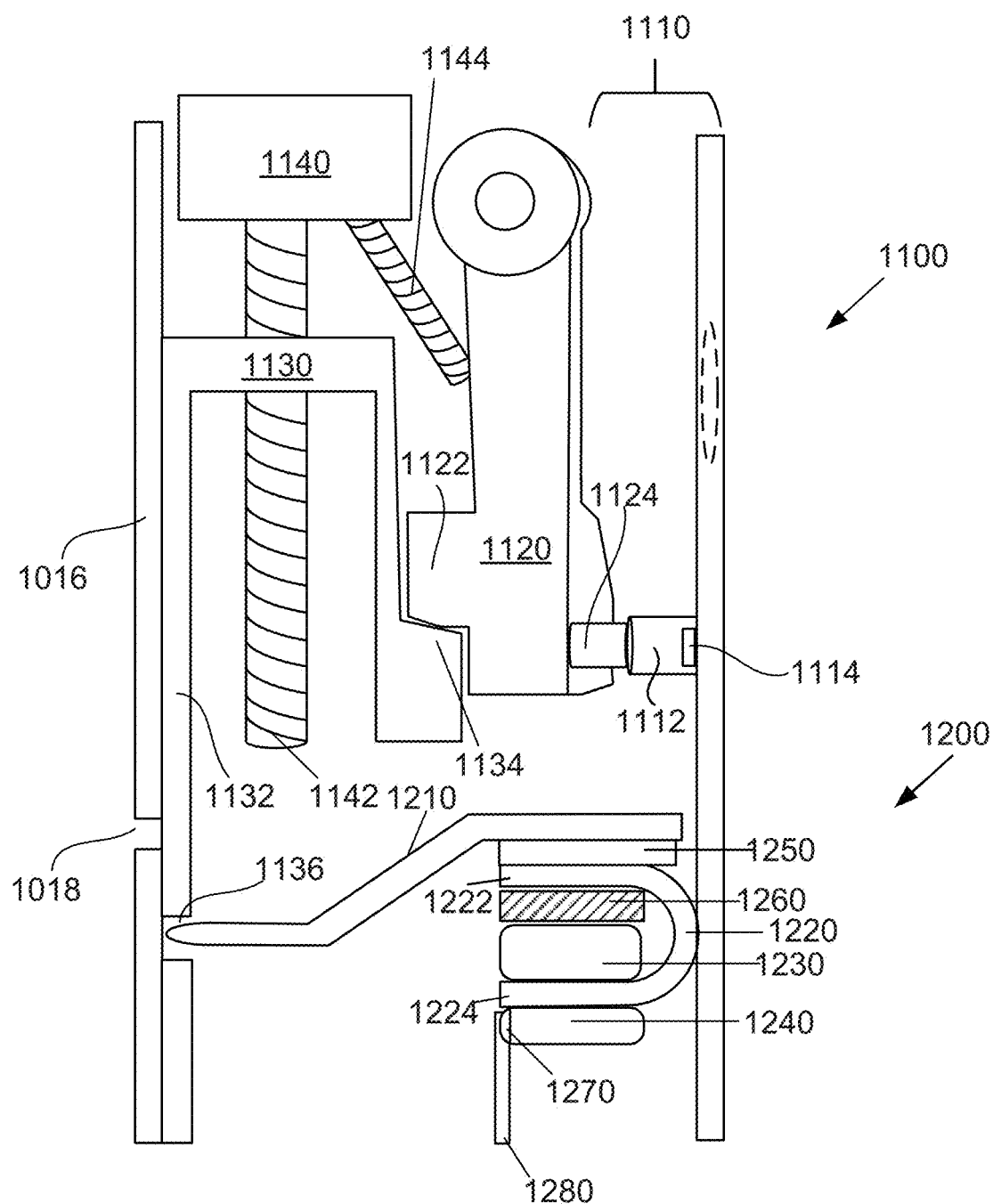
FIG. 22 illustrates an ingestible device including a sampling system and a two-stage valve system in its first stage.

FIG. 22 illustrates an embodiment of ingestible device 1000 with a relatively detailed view of both valve system 1100 and sampling system 1200. FIG. 22 shows valve system 1100 positioned prior to actuation of actuation system 1110 (e.g., when configured as shown in FIGS. 13A, 14A, 15A and 20A).

Figure 23:
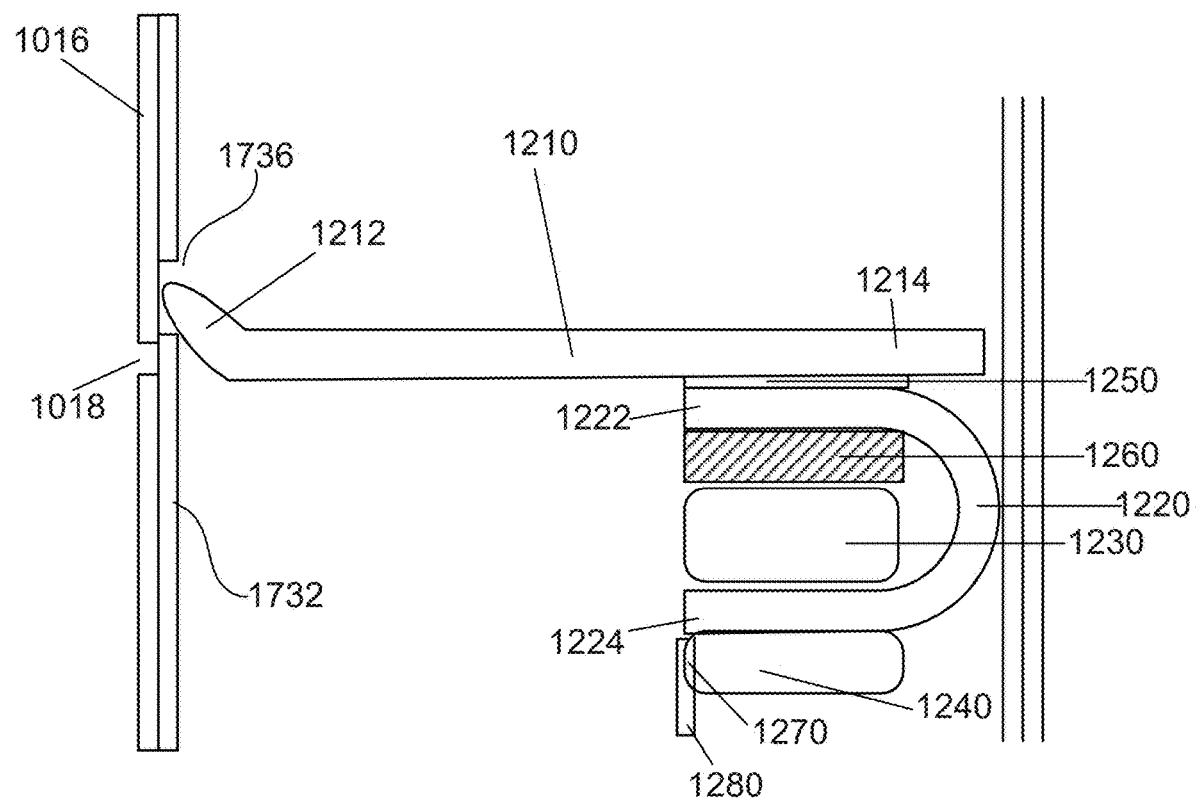
FIG. 23 illustrates an ingestible device including a sampling system and a portion of a three-stage valve system in third third stage.

FIG. 23 illustrates an embodiment of an ingestible device including sampling system 1200 and three-stage valve system 1700 positioned in its third stage.

Figure 24:
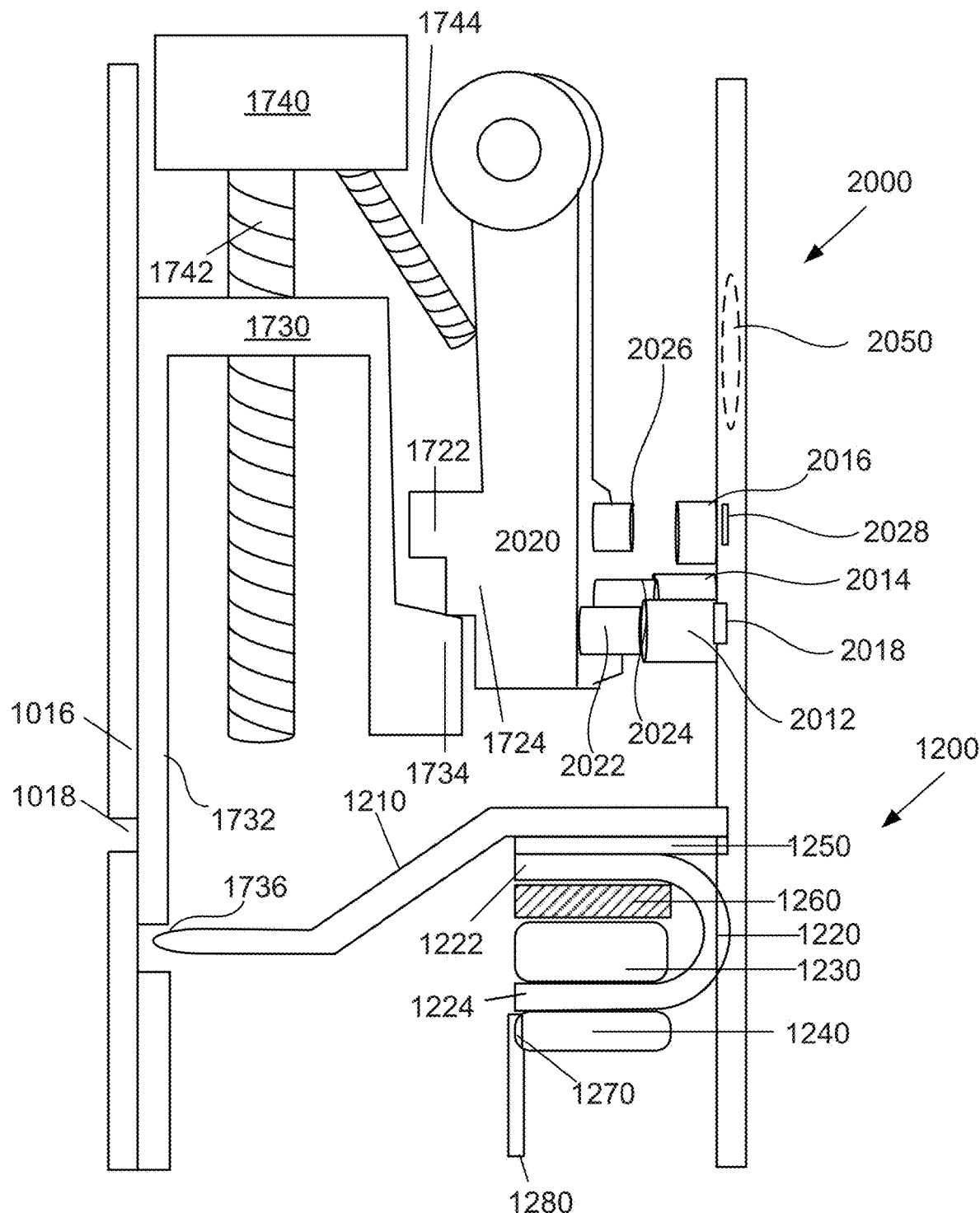
FIG. 24 illustrates an ingestible device including a sampling system and a three-stage valve system in third first stage.

FIG. 24 illustrates an embodiment of an ingestible device 1000 including sampling system 1200 and valve system 2000 positioned in its third stage.

Figure 25:
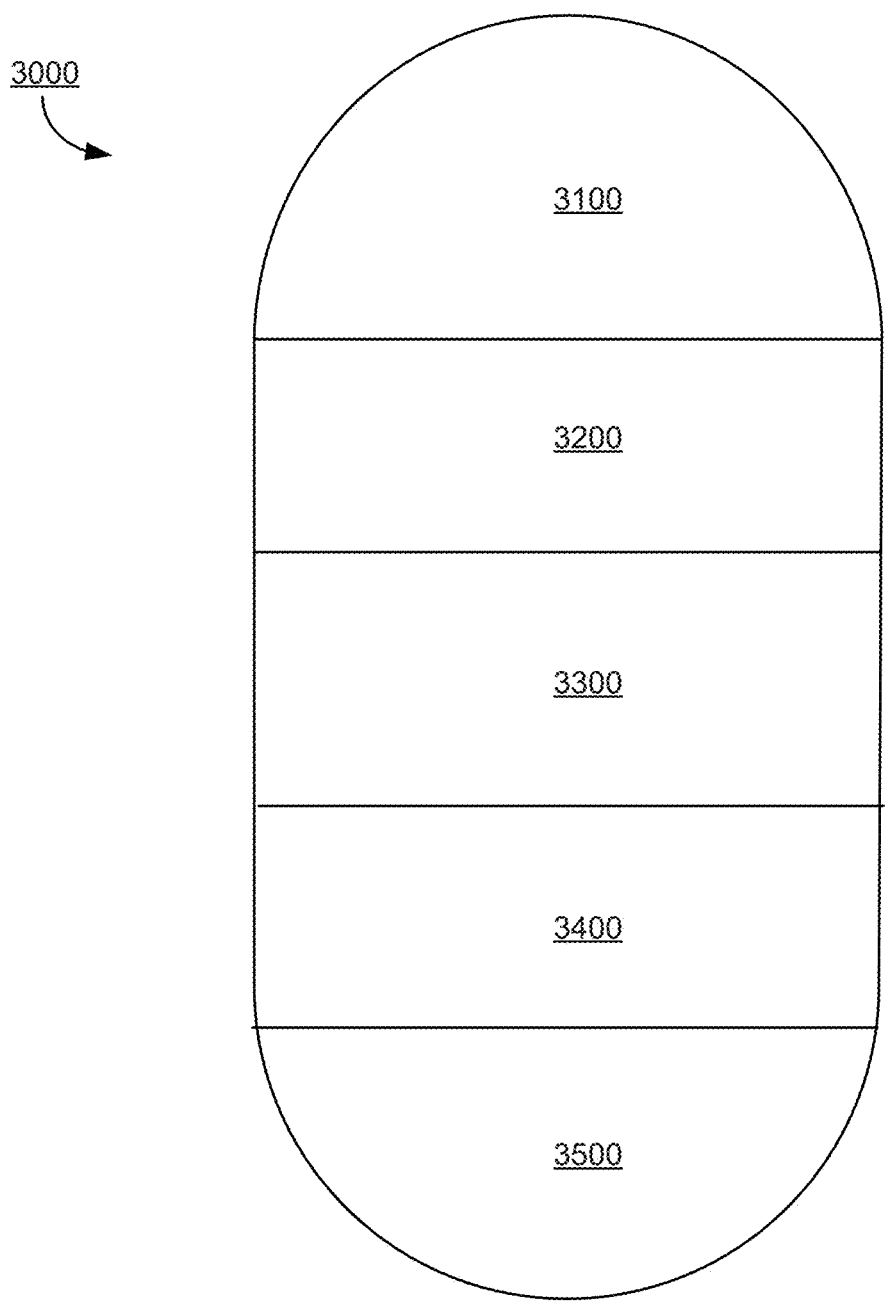
FIG. 25 is a highly schematic illustrate of an ingestible device.

FIG. 25 is a highly schematic illustration of an ingestible device 3000 that contains multiple different systems that cooperate for obtaining a sample and analyzing a sample, e.g., within the GI tract of a subject. Ingestible device 3000 includes a power system 3100 (e.g., one or more batteries), configured to power an electronics system 3200 (e.g., including a control system, optionally in signal communication with an external base station), and an analytic system 3500.

Exemplary analytical systems include assay systems, such as, for example, optical systems containing one or more sources of radiation and/or one more detectors. Such systems may use, for example, a light source that illuminates and a sample and a detector configured to detect light that is emitted by the sample (e.g., fluorescence spectroscopy), optical density (e.g., the portion of light that passes through the sample), and/or light that is diffracted by sample (e.g., diffraction optics). An analytical system may use, for example, ELISA (enzyme-linked immunosorbent assay). An analytical system may use, for example, LOCI (luminescent oxygen channeling). An analytical technique may involve incubating and/or diluting a sample before or during the analysis/assaying of the sample. An analytical technique may involve the use of staining/dyeing a live cell.

Ingestible device 3000 also includes a sampling system 3400 for taking in a sample from the environment exterior to ingestible device 3000, and a valve system 3300 that regulates the ability of a fluid to access sampling system 3400.

Figure 26:
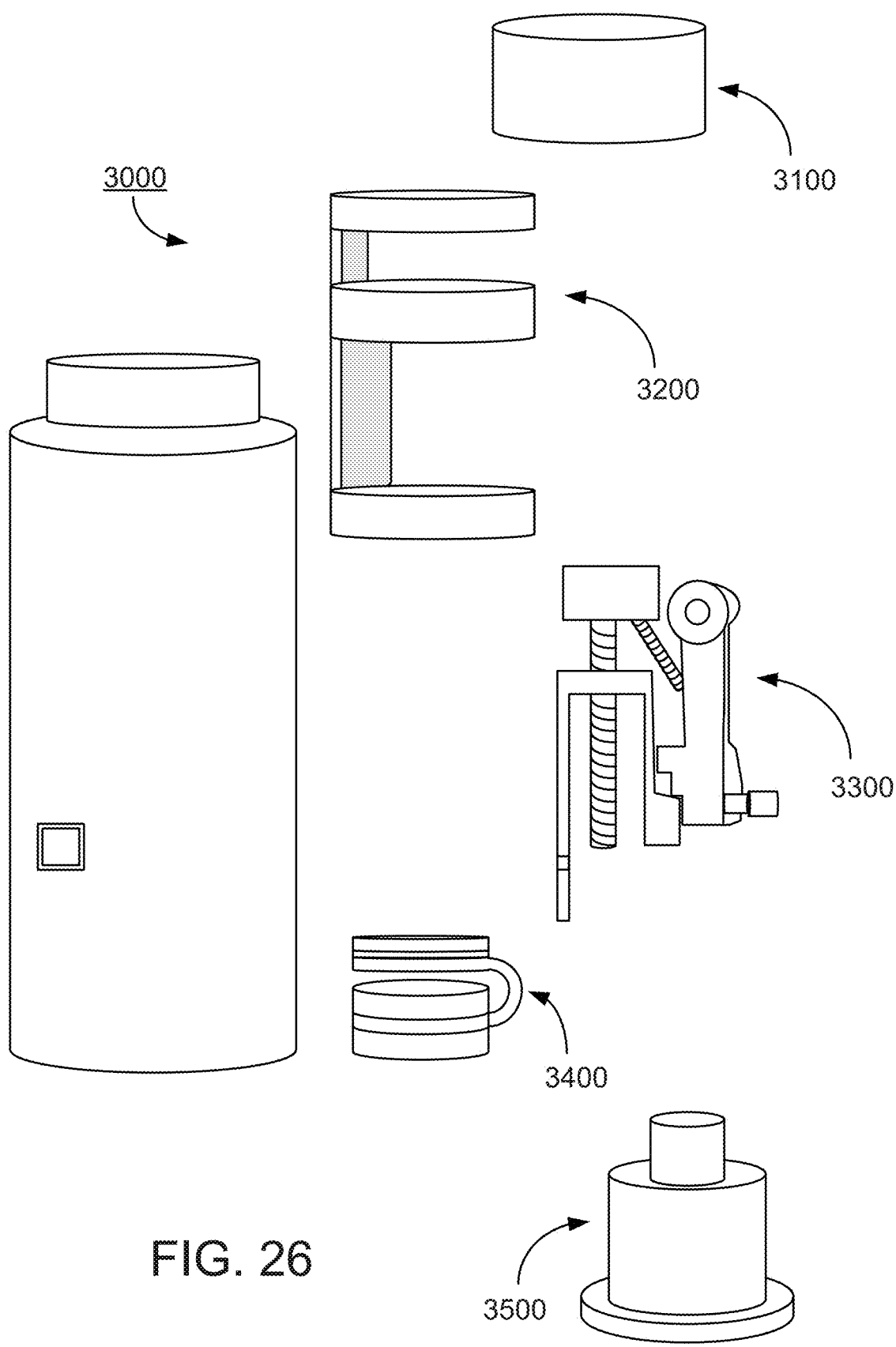
FIG. 26 is an exploded view of an ingestible device.

FIG. 26 provides an exploded view of the ingestible device 3000. FIG. 26 includes an exploded view of ingestible device 3000, showing a general configuration of the systems in FIG. 25. FIG. 26 includes power system 3100 (e.g., a stack of batteries), electronic system 3200 (e.g., a PCB and associated wiring), valve system 3300, sampling system 3400, and analytic system 3500.

Figure 27:
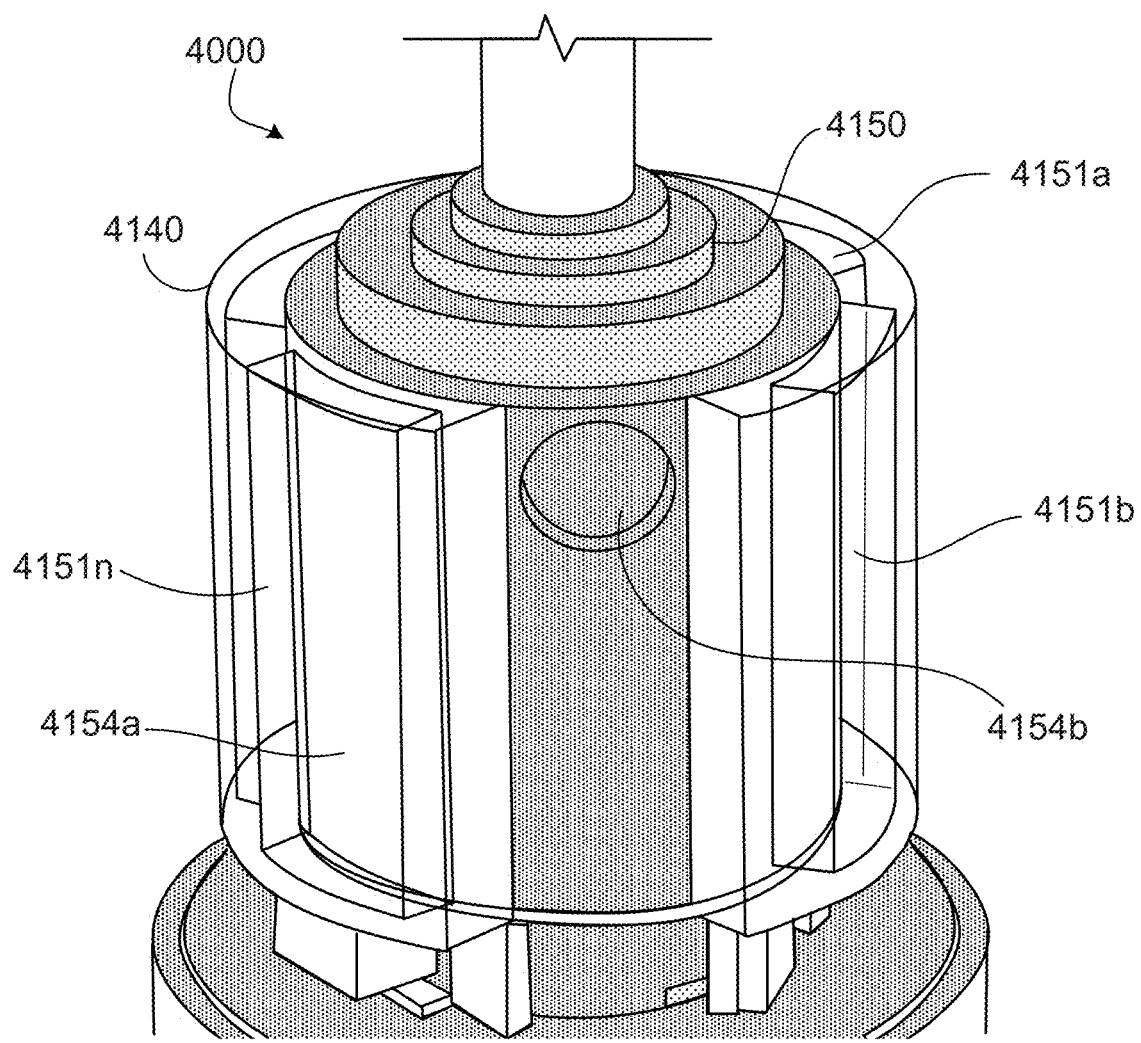
FIG. 27 illustrates a portion of an ingestible device with a port in an open position exposed to the exterior of device.

FIG. 27 illustrates a portion of an ingestible device 4000 with a port 4154b in an open position to the exterior of the ingestible device 4000. The ingestible device 400 may include a cylinder-shaped rotatable element 4150 that includes sampling ports 4154a-b on the wall of the rotatable element 4150. The sampling chamber 4150 is wrapped by a shell element 4140 with dividers to form a series of dilution chambers 4151a-n between the shell element 4140 and the rotatable element 4150. In operation, when the ingestible device 4000 determines the device itself arrives at a target location within the GI tract, the rotatable element 4150 may be rotated into an open position such that an aperture of the shell element 4140 is aligned with the port 4154b on the wall of the rotatable element 4150 and the port 4154b is exposed to the exterior of the ingestible device 4000 through the aperture. In this way, fluid from the GI tract can enter the port 4154b and occupy the volume defined by the port 154b. In the embodiment shown in FIG. 24, the port 4154b may be a depression on the surface of a rotatable element 4150 and a number of dilution chambers 4151a-n are positioned circumferentially around the axis of rotation of the rotatable element 4150. As previously discussed, each of the dilution chambers 4151a-n may store a dilution fluid. In one embodiment, the depression is a cylindrical depression. Optionally, the depression may be a rectangular depression, or any concave depression forming a regular or irregular shape. In another embodiment, the port 4154b may be connected to a chamber (not shown) within the rotatable element 4150 to create an enlarged space to store the GI fluid sample from the external environment of the ingestible device.

In some embodiments, the ingestible device 4000 may further include a controller and an actuator. The controller may determine that the ingestible device 100 is located at a target location of the GI tract, and then the actuator may trigger the rotation of the rotatable element 4150 to align the port 4154b at the open position to initiate the sampling. For example, the housing of ingestible device 4000 may have a pH-sensitive enteric coating to detect or otherwise be sensitive to a pH level of the environment external to the ingestible device 4000, based on which the controller may determine whether the ingestible device has arrived at a target location. For another example, the ingestible device 4000 may include an optical sensing unit that transmits an illumination to the environment and collects a reflectance, based on which, the regio-specific location of the ingestible device 4000 may be identified based on optical characteristics of the reflectance.

Figure 28:
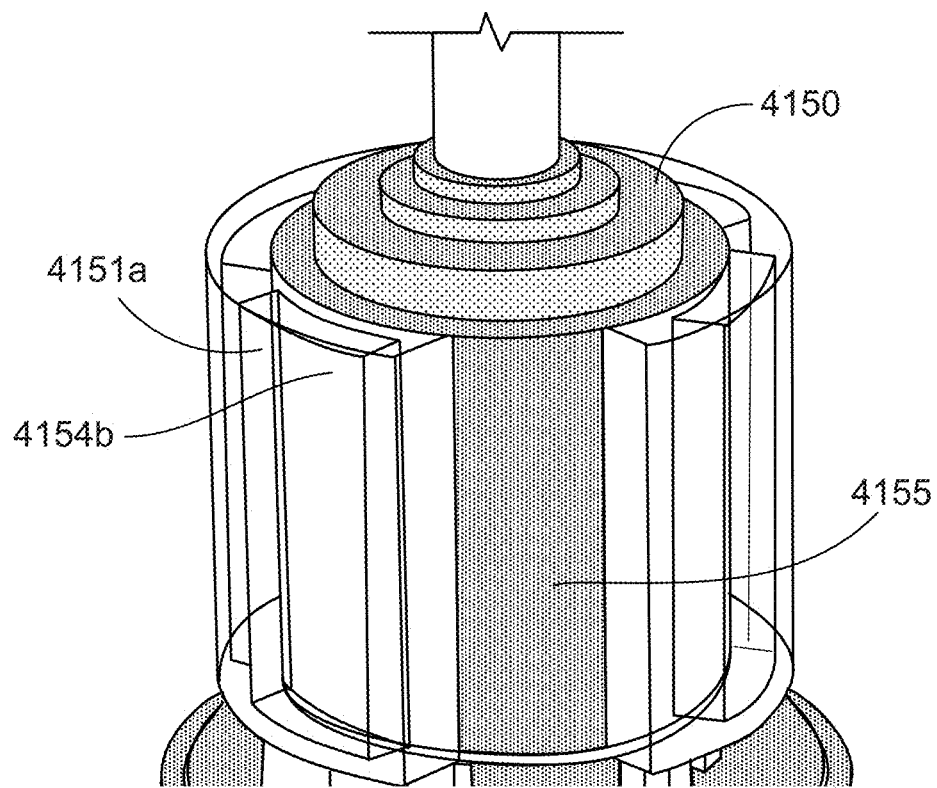
FIG. 28 illustrates a portion of an ingestible device with a port in a first position in fluid communication with a first incubation chamber.

FIG. 28 shows one embodiment of a portion of an ingestible device with a port 4154b at a first position aligned with a first dilution chamber 4151a. In operation, the rotatable element 4150 may be rotated to align the sampling port 4154b and the first dilution chamber 4151a such that the fluid sample from the GI tract stored within the volume of the sampling port 4154*b* can be combined with dilution fluid in the first dilution chamber to form a first dilution. The first dilution may then occupy the combined volume of the port 4154*b* and first dilution chamber 4151*a*. Optionally, the rotatable element 4150 may be subsequently rotated to a second position such that the port 4154*b* containing a portion of the first dilution is then moved to be aligned and in fluid communication with another dilution chamber, e.g., a second dilution chamber that is next to the first dilution chamber along the rotational direction. In this way, the first dilution stored within the port 4154*b* may then again be diluted with the dilution fluid stored within the second dilution chamber. Similarly, if the rotatable element 4150 keeps rotating and allows the port 4154*b* to be serially aligned with each dilution chamber, then the original GI fluid sample may be diluted serially and each dilution chambers 4151*a-n* may be left with a diluted GI fluid sample at a different dilution ratio.

Figure 29:
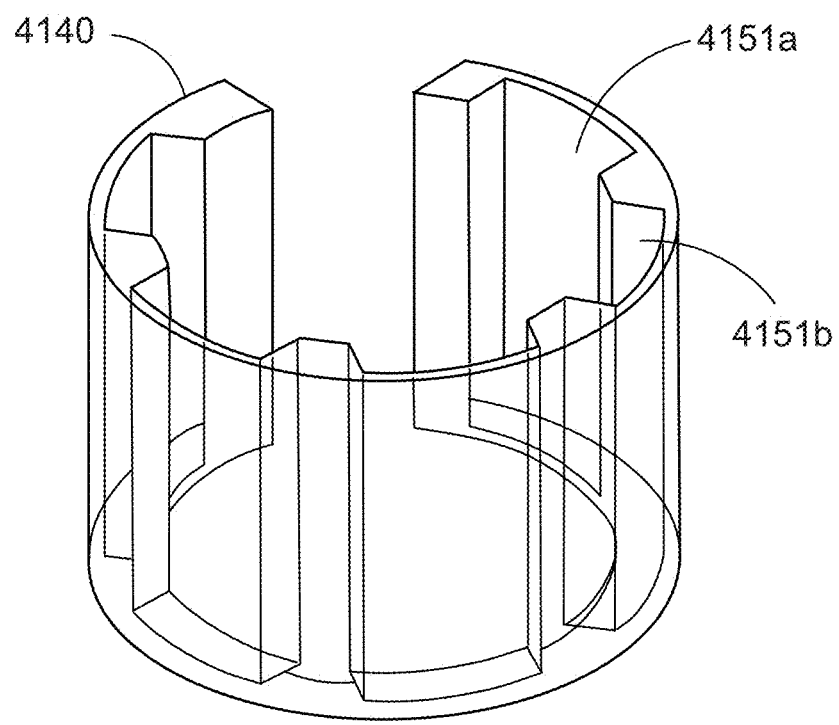
FIG. 29 illustrates a member forming part of a set of five incubation chambers suitable for an ingestible device.

FIG. 29 shows an embodiment of an element 4140 forming part of a set of five dilution chambers (e.g., including 4151*a-b*) for surrounding a rotatable element (e.g., 4150 in FIGS. 21-22) in an ingestible device as described herein. In one embodiment, the device may contain a single dilution chamber. Alternatively, the device may contain 2, 3, 4, 5, 6, 7, 8 or greater than 8 dilution chambers.

In some embodiments, each dilution chamber 4151*a-n* may be filled with a dilution fluid prior to the ingestible device 4000 being administered. In another embodiment, the dilution fluid may be stored in a separate reservoir (not shown) within the ingestible device 4000. At the time when the ingestible device 4000 is determined to be at a target location within the GI tract, a pumping mechanism may pump the dilution fluid into one or more dilution chambers 4151*a-b* via one or more outlet (not shown) of the reservoir.

In some embodiments, the shell element 4140 may have valves or pumps (not shown) between the dilution chambers 4151*a-n*. For example, the diluted fluid from a first dilution chamber may be pumped into a second dilution chamber via a valve between the two chambers.

Devices of the type depicted in FIGS. 27-29 optionally can include a sampling system as disclosed herein.

Figure 30:
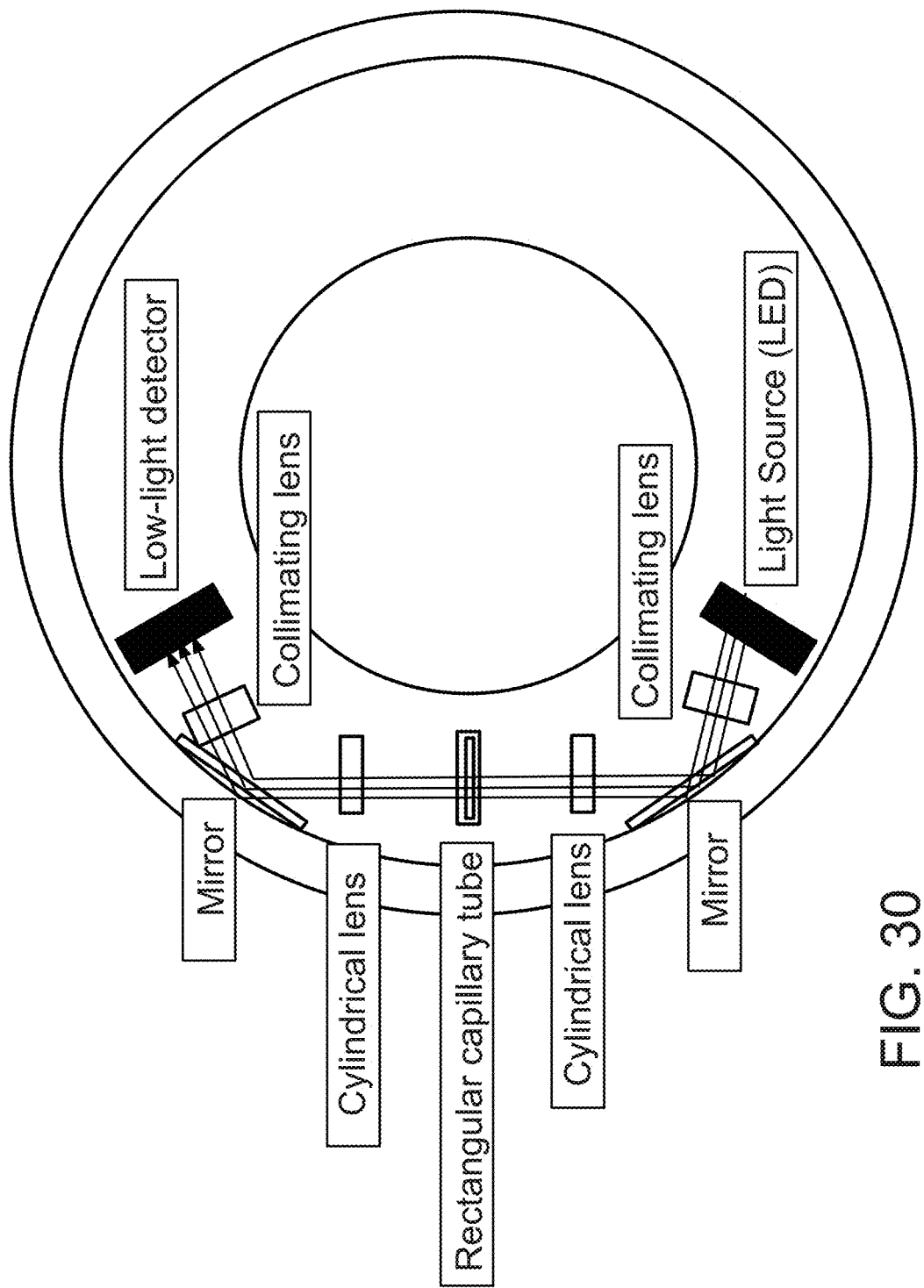
FIG. 30 illustrates a partial cross-sectional view of optics in an ingestible device.

In certain embodiments, an ingestible device includes a microscopic evaluation system. In some embodiments, bacterial cells in a sample may be first labeled with fluorescent dyes (such as those described herein), and the fluorescently-labeled cells may be imaged and counted by the microscopic evaluation using an ingestible device as described herein. In other embodiments, the fluorescently-labeled cells are counted as they pass through an onboard flow system (e.g., microfluidic single cell channeling). Examples of flow cytometry systems include hydrodynamic focusing, small diameter capillary tube flow, and rectangular capillary tube flow. As described herein, live bacteria cells are labeled, and the principles of flow cytometry are used to quantify labeled cells. Generally speaking, the photons from an incident laser beam are absorbed by the fluorophore and raised to a higher, unstable energy level. Within less than a nanosecond, the fluorophore re-emits the light at a longer representative wavelength where it is passed through a series of dichroic filters. This reemitted light can be collected and interpreted as proportional to the number of labeled bacteria cells. In some embodiments, a sheath fluid is not used as part of the flow system to help accommodate the volume restrictions of the device. In some embodiments, a rectangular capillary tube is used to achieve a sufficiently large cross-sectional area and relatively thin inspection area. The flow cytometry optical system operates parallel to the fluidics system and serves to observe the redirection of light passing through the cell and delivers information about the bacterial cells. In some embodiments, rather than using a conventional laser and spherical lenses to focus the light to a point, an LED and cylindrical lenses are used to focus the light to a line across a rectangular capillary tube. In other embodiments, collimating lenses are used to make the light source parallel, while cylindrical lenses are used to refine the inspection area. An exemplary optical configuration for this arrangement can be seen in FIG. 30. In some embodiments, optical filters can be added to permit the use of fluorophores. The characteristic wavelength of reemitted light from the fluorophores can be isolated and detected with the use of dichroic, bandpass, and short or long wave pass filters. Generally, multiple dichroic lenses and photomultipliers are used, however, due to space limitations, only a single side-scatter detector and forward scatter detector may be used in certain embodiments.

One of the design challenges of integrating flow cytometry into the device is to provide a pumping mechanism. Without moving fluid, individual bacteria cells cannot be identified and accounted for by flow cytometry within a fixed volume of fluid. In some embodiments, a gear motor is to move fluid through the device. For example, a micromotor comprising a planetary gearhead (e.g., with a 25:1 reduction) can provide the desired amount of torque to create fluid flow. In another embodiment, a series of piezoelectric resistors embedded in the surface of a microfabricated plate is used to create flow. In yet another embodiment, a micropump that includes a pair of one-way valves and uses a magnetic pump membrane actuated by an external magnetic field is used to create flow.

Figure 31:
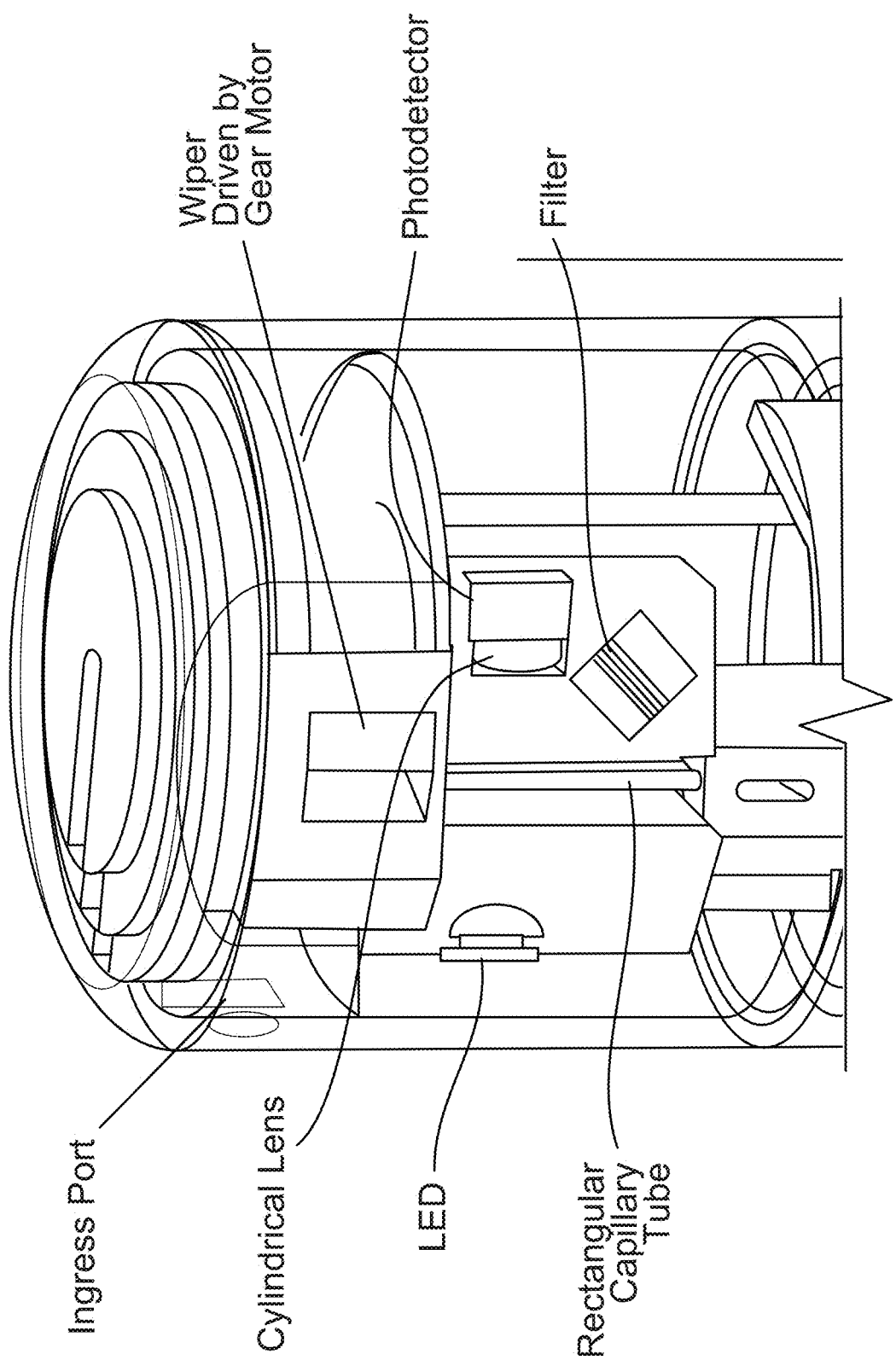
FIG. 31 illustrates components of the optics and flow chamber systems in an ingestible device.

In some embodiments, the system architecture comprises an opening and sealing mechanism combined with a rotary wiper which creates a pressure driven flow via a gear motor. The gear motor can be used for other functions in the device. As shown in FIG. 31, the components of the optics and flow chamber systems fit within the device. In some embodiments, the sample fluid is absorbed via a flexible membrane at the top of the capsule. In some embodiments, the gear motor has 270° of permissible travel which serves to open and fill the fluid chamber. During closure, the motor closes the ingress port while simultaneously pushing the fluid through the rectangular capillary tube where the optical system is located. The threaded component allows the flexible membrane to close and seal the ingress channel without changing the wiper height. In some embodiments, the volume of the sample chamber is 25 µL, 50 µL, 75 µL or more. In some embodiments, two or more samples are taken from the GI tract to procure a sufficient sample size. Referring to FIG. 31, an LED on the left side of the capillary tube and the two low-light detectors on the right for capturing forward and side scatter are shown. Once the fluid passes through the capillary tube, it exits the capsule via a one-way valve. In certain embodiments, the flow system allows for the detection of cell size and internal cell complexity, in addition to cell quantitation.

The foregoing discussion is not exhaustive with respect to various ingestible device designs, either with respect to sampling componentry or absorbent (sponge) design.

As an example, while ingestible devices have been described that include one or more optical systems incorporated into the ingestible device, in some embodiments, an ingestible device does not include an optical system. Optionally, such ingestible devices may also not include any other analytical componentry. In embodiments of an ingestible device which do not include an optical system and/or other analytical componentry, there may be more room inside the ingestible device to store one or more samples.

Exemplary ingestible devices are provided in U.S. Ser. No. 14/460,893, which is incorporated by reference herein.

Figure 32:
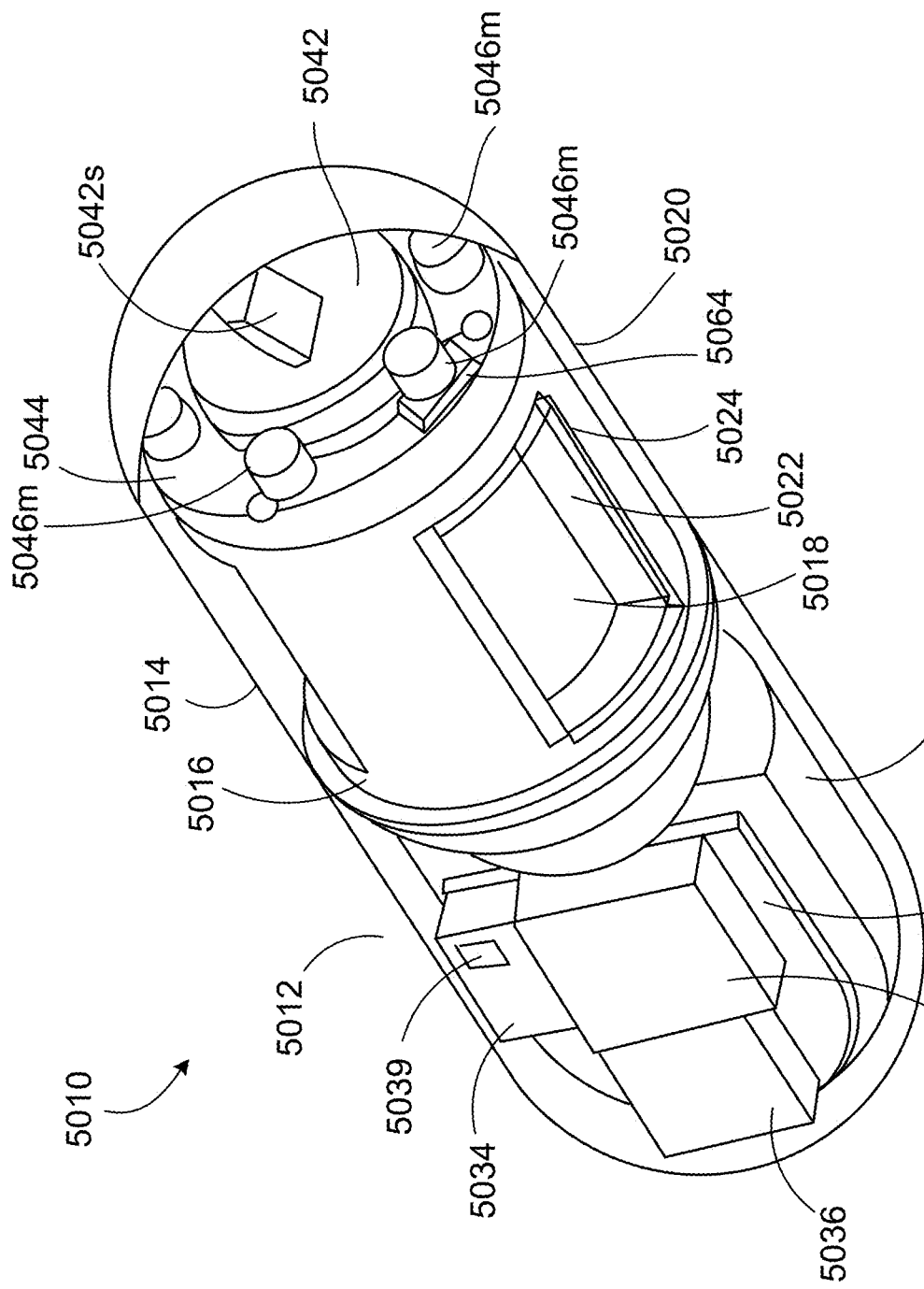
FIG. 32 shows a partial view of an ingestible device

FIG. 32 shows a partial view of an exemplary embodiment of an ingestible device 5010 in which a portion of the enclosure of ingestible device 5010 has been removed. Ingestible device 5010 may be used for collecting substances. Ingestible device 5010 may generally be in the shape of a capsule, like a conventional pill. Accordingly, the shape of ingestible device 5010 provides for easier ingestion and is also familiar to healthcare practitioners and patients.

The structure of ingestible device 5010 includes first portions and second portions 5012 and 5014. First portion 5012 includes control electronics, a power supply, and a communication system. Second portion 5014 is generally configured to interact with the GI tract, such as, for example but not limited to, sample collection, substance delivery and environmental monitoring. Second portion 5014 includes a storage sub-unit 16 with one or more chambers 5018 and a chamber enclosure 5020 that encloses or overlays a storage sub-unit 5016. Each chamber 5018 has a corresponding chamber opening 5022. Chamber enclosure 5020 has an access port 5024. In this example embodiment, ingestible device 5010 includes three chambers 5018, but there can be other embodiments that have one, two or more than three chambers 5018.

FIGS. 33A-33C illustrate operation of ingestible device 5010. Generally, chamber enclosure 5020 operates as a "closed-loop" revolver mechanism. Chamber enclosure 5020 rotates, in a controlled manner, to align the access port 5024 with each of chamber openings 5022 for collecting, at targeted locations, samples of the contents in the GI into corresponding chamber 5018, and/or for delivering substances stored in chambers 5018 to targeted locations within the body.

Generally, during collection of samples, the rotation of chamber enclosure 5020 may be described as a "closed-loop" revolver mechanism because each chamber opening 5022 is exposed only once during the passage of ingestible device 5010 within the body in order to avoid cross-contamination of the collected samples. In other words, in some embodiments, chamber enclosure 5020 ideally rotates only once when collecting samples during each usage of ingestible device 5010 so that access port 5024 aligns with each of chamber openings 5022 serially and only once. That is, during collection of samples, access port 2224 does not bypass any chamber opening 5022 and also does not return to a previous chamber opening 5022 during its rotation.

In some embodiments, chamber enclosure 5020 can rotate in a bidirectional motion before completing one revolution and/or perform multiple revolutions during one usage of the ingestible device 5010 so that at least one chamber opening 5022 is exposed multiple times. A chamber opening 5022 may need to be exposed multiple times if its corresponding chamber stores solids or semi-solid reagents, sensors or cleaning agents for cleaning the GI tract.

As illustrated in FIG. 33A, shown therein generally is ingestible device 5010 in an open position 5010a in which access port 5024 on chamber enclosure 5020 is aligned with a chamber opening 5022. In this configuration, ingestible device 5010 may collect substances through chamber opening 5022. In other words, the contents of the GI tract may be forced into exposed chamber 5018 through muscular contractions (e.g., peristalsis).

Thereafter, chamber enclosure 5020 may rotate to seal chamber opening 5022. FIG. 33B shows ingestible device 5010 with a partially open/partially closed position 5010b in which access port 5024 has been rotated such that chamber enclosure 5020 partially seals chamber opening 5022.

FIG. 33C shows ingestible device 5010 in a closed position 5010c, in which the chamber enclosure 5020 has been rotated a distance such that access port 5024 completely seals chamber opening 5022. If chamber enclosure 5020 has not rotated one revolution, chamber enclosure 5020 may continue to rotate in the same direction in order to align access port 5024 with another chamber opening 5022 depending if ingestible device 5010 has been configured to perform another operation (i.e. sampling or distribution).

In another example embodiment, chamber enclosure 5020 may be stationary and storage sub-unit 5016 may instead rotate to align its one or more chamber openings 5022 with access port 5024. Rotating storage sub-unit 5016 instead of chamber enclosure 5020 may provide greater control over the rotation motion and a more constant motion since storage sub-unit 5016 would not be subjected to a varying viscosity arising from the contents in the GI tract. This arrangement, however, may limit a volume of at least one of chambers 5018.

In some embodiments, chamber enclosure 5020 or storage sub-unit 5016 may rotate in a predetermined sequence of bidirectional rotational motions. As described above, when storage sub-unit 5016 is configured to rotate instead of chamber enclosure 5020, the volume of at least one of chambers 5018 can be limited. In order to avoid having to limit the volume of the chambers 5018, non-recess areas that may be used to separate different chambers 5018 in storage sub-unit 5016 may be minimized in volume or removed. Ingestible device 5010 can rotate in a first direction for aligning access port 5024 with one of the two adjacent chambers. Ingestible device 5010 can be configured to rotate in a second direction that is opposite to the first direction in order to avoid cross contamination between samples collected into or substances released from those two adjacent chambers.

Ingestible device 5010 may be used for collecting usable samples from the contents of the GI tract (e.g., 100 µL sized samples) and maintaining each sample in isolation from one another until the samples are extracted.

In some embodiments, ingestible device 5010 may also be configured to conduct in-vivo measurements. Ingestible device 5010 is introduced into the body with some of chambers 5018 being empty and some of chambers 5018 carrying at least one reagents. At a predefined location in the body, ingestible device 5010 is configured to collect a sample from the GI tract and to store the sample into a chamber carrying at least one reagent. After collection, in-vivo analysis may be conducted based on how the collected sample interacts with the reagent inside chamber 5018. For example, ingestible device 5010 may use a biochemistry assay, such as an enzyme-linked immunosorbent assay (ELISA), for performing in-situ experiments on collected samples. Alternatively, peripherals can be included into chambers 5018 for changing the dynamics of several in-vivo analysis and measurements. The peripherals may include a light source, a receiver, a transducer, a heater, and the like. In general, the in-vivo experiments vary according to the type of information that is being sought.

FIG. 34 illustrates an exploded view of the components of ingestible device 5010 in one example embodiment. First portion 5012 of ingestible device 5010 includes an end closure 5030, and electronic components embedded on a main printed circuit board (PCB) 5032 including a communication subsystem having communication peripherals 5034 and a transceiver 5036, a main microcontroller (i.e. processor) 5038, a power supply 5040 and other peripheral components described in further detail below. Second portion 5014 of ingestible device 5010 generally includes a motor 5042, storage sub-unit 5016, a secondary PCB 5044, an encoding magnet arrangement 5046m and the chamber enclosure 5020. Generally, by placing main PCB 5032 and secondary PCB 5044 in distinct regions inside ingestible device 5010, they may be prevented from experiencing the same electrical or physical hazards. Motor 42 is inserted into a motor compartment 5054 that is located in the center of storage sub-unit 5016. PCB 5044 is annular and includes one or more peripheral electronic components (e.g., a capacitor 5062 and a resistor 4060, which can be used as a pull-up resistor), and a sensor 5064. 5039 is a magnetic switch. 5042s is a shaft. 5056 are access holes.

End enclosure 5030 provides a hollow space defined by an inner wall 5048 that is cylindrical with a domed end portion. End enclosure 5030 also includes engagement members 5050 for aligning and releasably engaging with storage sub-unit 5016 to releasably lock end enclosure 5030 in place during operation. In particular, engagement members 5050 releasably engage complementary structures 5052 in storage sub-unit 5016. When end enclosure 5030 locks with storage sub-unit 5016, end enclosure 5030 overlaps with a rear of storage sub-unit 5016 and creates a seal. In some embodiments, the overlap between end enclosure 5030 and storage sub-unit 5016 may span a width of 3 millimeters.

Some or all of the sponges of the above-described sampling systems may contain one or more preservatives (see discussion above). Typically, the assay sponge and/or the volume sponge 1230 and/or the transfer sponge contain one or more preservatives. Typically, the preservative(s) are selected based on the analyte of interest, e.g., an analyte (such as a nucleic acid or protein biomarker) for a GI disorder.

Examples of such GI orders include inflammatory bowel disease, Crohn's disease (e.g., active Crohn's disease, refractory Crohn's disease, or fistulizing Crohn's disease), ulcerative colitis, indeterminate colitis, infectious colitis, microscopic colitis, drug or chemical-induced colitis, diverticulitis, ischemic colitis, pseudomembranous colitis, hemorrhagic colitis, hemolytic-uremic syndrome colitis, collagenous colitis, colitis associated with disorders of innate immunity as in leukocyte adhesion deficiency-1, gastritis, peptic ulcers, stress ulcers, bleeding ulcers, gastric hyperacidity, dyspepsia, gastroparesis, Zollinger-Ellison syndrome, gastroesophageal reflux disease, short-bowel (anastomosis) syndrome, mucositis (e.g., oral mucositis, gastrointestinal mucositis, nasal mucositis and proctitis), necrotizing enterocolitis, esophagitis, a hypersecretory state associated with systemic mastocytosis, basophilic leukemia, hyperhistaminemia, Celiac disease (e.g., nontropical Sprue), enteropathy associated with seronegative arthropathies, chronic granulomatous disease, food allergies, enterocolitis (e.g., Helicobacter pylori-infected chronic active gastritis), other forms of gastrointestinal inflammation caused by an infectious agent, irritable colon syndrome, small intestinal bacterial overgrowth (SIBO) and pouchitis. "Inflammatory Bowel Disease" or "IBD" is a chronic inflammatory autoimmune condition of the gastrointestinal (GI) tract. Although the cause of IBD remains unknown, several factors such as genetic, infectious and immunologic susceptibility have been implicated. IBD is much more common in Caucasians, especially those of Jewish descent. A chronic inflammatory autoimmune condition of the gastrointestinal (GI) tract presents clinically as either ulcerative colitis (UC) or Crohn's disease (CD). Both IBD conditions are associated with an increased risk for malignancy of the GI tract. "Crohn's disease" ("CD") is a chronic transmural inflammatory disease with the potential to affect any part of the entire GI tract, and UC is a mucosal inflammation of the colon. Both conditions are characterized clinically by frequent bowel motions, malnutrition, and dehydration, with disruption in the activities of daily living. CD is frequently complicated by the development of malabsorption, strictures, and fistulae and may involve repeated surgery. UC, less frequently, may be complicated by severe bloody diarrhea and toxic megacolon, also involving surgery. The most prominent feature Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease involve surgery at some point, but subsequent relapse is common and continuous medical treatment is usual. Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils. "Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be involved for acute, severe or chronic, unremitting ulcerative colitis. A "symptom" of a disease or disorder (e.g., inflammatory bowel disease, e.g., ulcerative colitis or Crohn's disease) is any morbid phenomenon or departure from the normal in structure, function, or sensation, experienced by a subject and indicative of disease.

Biomarkers

A biomarker as described herein can be a nucleic acid, such as DNA or RNA, a protein, a small molecule, or a bacterium. Biomarkers as described herein are present in the GI tract, and can be used to detect a disease in the GI tract of a subject, e.g., an inflammatory disease. Biomarkers can also be used to monitor the progress or remission of a disease of the GI tract, e.g., an inflammatory disease. The biomarkers can be collected from any portion of the GI tract, e.g., the biomarkers can be collected form the distal small bowel to the proximal large bowel of a subject. In some embodiments, the biomarkers are produced by the cells of the subject in the GI tract. In some embodiments, the biomarkers are produced by a microorganism, e.g., a bacterium, in the GI tract. In exemplary embodiments, the biomarkers described herein are present or produced in the intestinal mucosa, thereby indicating intestinal inflammation.

In some embodiments, the biomarker is a small molecule. A small molecule is an organic compound of low molecule weight (<100 daltons, approximately). The conditions within an ingestible device, as disclosed herein, can be formulated to be improve the capacity of the device to retain small molecules. In some embodiments, one or more small molecules enter a device as disclosed herein in the GI tract, and are contacted with one or more preservatives, e.g., a mixture of preservatives that stabilize small molecules and inhibit their degradation. In some embodiments, the small molecule biomarker is a small molecule drug, e.g., a small molecule drug used to treat an inflammatory disease. In some embodiments, the small molecule biomarker is cyclosporine.

In some embodiments, the biomarker is a nucleic acid. In some embodiments, one or more nucleic acid molecules enter a device as disclosed herein in the GI tract, and are contacted with one or more nucleic acid preservatives, e.g., a mixture of preservatives that stabilize nucleic acids and inhibit their degradation. In some embodiments, the nucleic acid is a DNA molecule. In some embodiments, the nucleic acid is an RNA molecule. There are many types of nucleic acid molecules known in the art that can be a biomarker, as described herein. In some embodiments, the nucleic acid biomarker can be a mRNA, a single-stranded RNA, a double-stranded RNA, an antisense RNA, a siRNA, a miRNA, a piRNA, a lincRNA, a tRNA, a ribozyme, a ribosomal RNA, or a snoRNA.

In some embodiments, the nucleic acid biomarker is a nucleic acid drug, e.g., a nucleic acid drug used to treat an inflammatory disease. In some embodiments, the nucleic acid biomarker is mongersen. Mongersen is a SMAD7 antisense oligonucleotide that can be used to treat inflammatory diseases of the GI tract, e.g., Crohn's disease and IBD.

Nucleic acid preservatives can be used to prevent or reduce the rate of nucleic acid degradation or denaturation, and/or increase the stability of nucleic acids, e.g., to maintain nucleic acid structure. In some embodiments, the nucleic acid preservative is nuclease inhibitor (deoxyribonuclease inhibitor). In some embodiments, the nucleic acid preservative is a ribonuclease inhibitor. Nuclease inhibitors and ribonuclease inhibitors are known in the art, and have been described in, e.g., U.S. Pat. No. 6,224,379, herein incorporated by reference in its entirety. In some embodiments, the nucleic acid preservative mixture can include EDTA, sodium citrate, an ammonium sulphate. In some embodiments, the RNA preservative mixture includes 2 mL of 0.5M EDTA, 1.25 ml of 1 M sodium citrate, 35 g of ammonium sulphate, and 46.8 mL of dH20. In some embodiments, the RNA preservative is an RNAlater™ stabilization solution (ThermoFisher Scientific), as described in U.S. Pat. No. 7,056,673, which is herein incorporated by reference in its entirety. In some embodiments, an RNA preservative can include one or more of triphenylmethane dyes (such as methyl green, crystal violet, pararosaniline, or tris-(4-aminophenyl)methane), cresyl violet, polyamines, and cobalt ions. In some embodiments, an RNA preservative can include one or more of spermine, spermidine, 1,10-diamino-4,7-diazadecane, 1,11-diamino-4,8-diazaundecane, 1,13-diamino-4,10-diazatridecane, 1,14-diamino-4,11-di-azatetradecane, 1,15-diamino-4,12-diazapentadecane, 1,16-diamino-4,13-diazahexadecane, 1,17-diamino-4,14-diaza-heptadecane, 1,18-diamino-4,15-diazanonadecane, 1,19-diamino-4,16-diazaeicosane, and 1,20-diamino-4,17-diazaheneicosane.

In some embodiments, the biomarker is a protein. In some embodiments, one or more proteins enter a device as disclosed herein in the GI tract, and are contacted with one or more preservatives, e.g., a mixture of preservatives that stabilize proteins and inhibit their degradation.

In some embodiments, the protein biomarker is a cytokine. The term "cytokines" refers to a broad group of secreted small proteins, typically less than 30 kD, that are involved in cell signaling in a variety of cellular and tissue contexts. Many cytokines modulate the immune system and are involved in inflammation and autoimmune disease. Cytokines can have pro-inflammatory or anti-inflammatory functions. Cytokines are produced by many different cell types, including immune cells, such as, e.g., macrophages, lymphocytes (e.g., B lymphocytes, T lymphocytes), monocytes, mast cells, endothelial cells, fibroblasts, T helper cells, and stromal cells. Exemplary types of cytokines include, without limitation, chemokines, interferons, interleukins, lymphokines, monokines, and tumor necrosis factors.

In some embodiments, the protein biomarker is a chemokine. Chemokines are chemotactic cytokines that can function to regulate the immune system by inducing chemotaxis or chemokinesis in immune cells during inflammation, e.g., leukocytes, monocytes, macrophages, T lymphocytes, mast cells, eosinophils, and neutrophils. For example, chemokines can activate and mobilize white blood cells in acute and chronic inflammation. Chemokines can be divided into four classes: alpha (CXC), beta (CC), gamma (C), and delta (CX3C). Chemokines can include, but are not limited to, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, CCL1, CCL2, CCL3, CCL3L1, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, XCL2, and CX3CL1. Chemokine receptors include CXCR1, CXCR2, CXCR3, CXCR4, CXCR5, CCR1, CCR2, CCR3, CCR4, CCR5, CCR6, CCR7, CCR8, CCR9, CCR10, CCR11, CX3CR1, and DARC. In some embodiments, the protein biomarker is a chemokine of the alpha, beta, gamma or delta family. In some embodiments, the protein biomarker is CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, CCL1, CCL2, CCL3, CCL3L1, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, XCL2, or CX3CL1. In some embodiments, the protein biomarker is a receptor that interacts with a chemokine, i.e., a chemokine receptor.

In some embodiments, the protein biomarker is an interferon (IFN). Interferons are proteins produced by a variety of cells, e.g., such as T cells and fibroblasts, to regulate the immune system in response to infection or cancerous cells. IFNs are divided into three classes: type I, type II, and type III IFNs. Interferons can also be classified as alpha, beta, gamma, tau, or omega interferons. Interferons can include, but are not limited to, IFNA1, IFNA2, IFNA4, IFNA5, IFNA6, IFNA7, IFNA8, IFNA10, IFN13, IFNA14, IFNA16, IFNA17, IFNA21, IFNG, IFNB1, IFNW, IFNE1, and IFNK. In some embodiments, the protein biomarker is a type I, type II, or type III interferon. In some embodiments, the protein biomarker is a, alpha, beta, gamma, tau, or omega interferon. In some embodiments, the protein biomarker is IFNA1, IFNA2, IFNA4, IFNA5, IFNA6, IFNA7, IFNA8, IFNA10, IFN13, IFNA14, IFNA16, IFNA17, IFNA21, IFNG, IFNB1, IFNW, IFNE1, or IFNK. In some embodiments, the protein biomarker can be interferon-γ.

In some embodiments, the protein biomarker is an interleukin. Interleukins modulate the immune system, and are involved in a wide variety of biological process, such as promoting the development and differentiation of T and B lymphocytes and hematopoietic cells. Interleukins are produced by many different cell types, including immune cells, such as, for example, leukocytes, T lymphocytes, e.g., CD4 T lymphocytes, monocytes, macrophages, and endothelial cells. Interleukins can be divided into families, including the interleukin 1, interleukin 2, interleukin 3, interleukin 4, interleukin 5, interleukin 6, interleukin 7 and 9, interleukin 8, interleukin 10, interleukin 11, interleukin 12, interleukin 13, interleukin 15, and interleukin 17 families. In some embodiments, the protein biomarker is a protein of interleukin family 1, 2, 3, 4, 5, 6, 7 and 9, 8, 10, 11, 12, 13, 15, or 17. Interleukins can include, but are not limited to, IL-1, IL-2, IL-3, IL-4, IL-5, IL-6, IL-7, IL-8 (CLCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36 and IL-37. In some embodiments, the protein biomarker is a protein of interleukin family 1, 2, 3, 4, 5, 6, 7 and 9, 8, 10, 11, 12, 13, 15, or 17. In some embodiments, the protein biomarker is IL-1, IL-2, IL-3, IL-4, IL-5, IL-6, IL-7, IL-8 (CLCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36 or IL-37.

In some embodiments, the protein biomarker is a lymphokine. Lymphokines are produced and secreted by lymphocytes, such as T cells, when lymphocytes contact antigens. Lymphokines regulate the immune response, and are involved in, e.g., attracting and activating immune cells, e.g., macrophages, lymphocyte transformation, and cell-mediated immunity. Lymphokines include, but are not limited to IL-2, IL-3, IL-4, IL-5, IL-6, granulocyte-macrophage colony-stimulating factor (GM-CSF), and interferon-γ. In some embodiments, the protein biomarker is GM-CSF.

In some embodiments, the protein biomarker is a tumor necrosis factor. The tumor necrosis factor (TNF) superfamily of cytokines are involved in a large variety of biological processes, including immune regulation and apoptosis. Tumor necrosis factors include, but are not limited to, TNF alpha (TNF, TNF a), lymphotoxin-alpha (LTA, LT-alpha, TNF-β), lymphotoxin-beta, (LTB, LT-beta, TNFC), CD40 ligand (CD40L, gp39, TNFSF7), CD70 (CD27L, TNFSF7), TNFSF4 (OX40L), TNFSF8 (CD30L), Fas ligand (FASL, FASLG), extodysplasin A (EDA), TNFSF9 (4-1BBL), TNF-related apoptosis inducing ligand (TNFSF10, TRAIL), TNFSF11, TNFSF12, TNFSF13, TNFSF13B, TNFSF14, TNFSF15, and TNFSF18. In some embodiments, the protein biomarker is TNF alpha (TNF, TNF a), lymphotoxin-alpha (LTA, LT-alpha, TNF-β), lymphotoxin-beta, (LTB, LT-beta, TNFC), CD40 ligand (CD40L, gp39, TNFSF7), CD70 (CD27L, TNFSF7), TNFSF4 (OX40L), TNFSF8 (CD30L), Fas ligand (FASL, FASLG), extodysplasin A (EDA), TNFSF9 (4-1BBL), TNF-related apoptosis inducing ligand (TNFSF10, TRAIL), TNFSF11, TNFSF12, TNFSF13, TNFSF13B, TNFSF14, TNFSF15, or TNFSF18.

In some embodiments, the protein biomarker is an integrin or a ligand to an integrin. In some embodiments, the protein biomarker is α4β7 integrin. In some embodiments, the protein biomarker is mucosal addressin cell adhesion molecule-1 (MAdCAM-1). The β1 integrin competes with β7 integrin for binding to α4 integrin on T cells. Expression of α4β7 integrin on T cells promotes the preferential trafficking of T cells to sites in the intestines, such as Peyer's patches. α4β7 integrin binds to the mucosal vascular addressin MAdCAM-1, which helps to direct leukocytes, such as T cells, into mucosa of the GI tract. MadCAM is expressed specifically on the venules of the mesenteric lymph node in the intestinal walls, and in Peyer's patches (PP). MadCAM s unregulated on the intestinal venules during inflammation.

In some embodiments, the protein biomarker is a monokine. Monokines are produced by immune cells, such as macrophages and monocytes, and help mediate the immune system, e.g., by attracting neutrophils via chemotaxis.

In some embodiments, the protein biomarker is an immunoglobulin. In some embodiments, the protein biomarker is an autoantibody associated with an autoimmune or inflammatory disease, e.g., an autoantibody associated with celiac disease, such as, but not limited to, tissue transglutaminase, gliadin, and endomysial antibodies. In some embodiments, the protein biomarker is anti-tissue transglutaminase antibody (tTG). Tissue transglutaminase is an enzyme that is abundant in the endothelial cells of the small intestines. The abnormal activation or dysregulation of tissue transglutaminase is associated with diseases such as celiac disease and inflammatory disorders. Anti-tissue transglutaminase antibodies are present in subjects who are allergic to dietary gluten. In some embodiments, the protein biomarker is anti-gliadin antibody (GP). Gliadin is a prolamin that is found in wheat, and is a component of gluten that can be antigenic to subjects with a celiac disease or a gluten allergy. Gliadins can be classified as a gliadin, gliadin, or γ gliadin. IgA, IgG, or IgE autoantibodies can be produced that bind to each type of gliadin in subjects with celiac disease or with a gluten sensitivity. In some embodiments, the protein biomarker is anto-endomysial antibody (EMA). The presence of EMA IgA antibodies correlates with gluten-sensitivity, celiac disease, and dermatitis herepeiformis.

In some embodiments, the protein biomarker is a protein or peptide drug, e.g., a protein or peptide drug used to treat an inflammatory disease. In some embodiments, the protein biomarker is a therapeutic antibody or other protein that binds to a protein involved in inflammatory disease, e.g., a therapeutic antibody that targets a cytokine. In some embodiments, the protein biomarker is a therapeutic antibody or other protein that targets and binds to tumor necrosis factor alpha (TNFα). In some embodiments, the protein biomarker is infliximab, adalimumab, certolizuman pegol, golimumab, or entanercept, or an antigen-binding portion thereof. In some embodiments, the protein biomarker is an antibody or other protein that binds to a therapeutic antibody or antigen-binding portion thereof, e.g., an antibody that binds to a therapeutic antibody or antigen-binding portion thereof that is used to treat inflammatory or autoimmune diseases of the GI tract. In some embodiments, the protein biomarker is an antibody or other protein that binds to a therapeutic antibody or antigen-binding portion thereof that targets and binds to TNFα, e.g., the protein biomarker is an antibody that binds to infliximab, adalimumab, certolizuman pegol, golimumab, or entanercept, or an antigen-binding portion thereof.

In some embodiments, the protein biomarker is secretory IgA. Secretory IgA is the predominant immunoglobulin isotype present in mucosal secretions, and is important for maintaining the immune barrier in the gastrointestinal tract. Secretory IgA helps to control the intestinal milieu in response to bacteria, parasites, and viruses. Elevated levels of fecal secretory IgA are associated with an upregulated immune response in the GI tract, and can therefore indicate inflammation.

In some embodiments, the protein biomarker is a protein that is not an immunoglobulin (e.g., not an antibody or autoantibody).

In some embodiments, the protein biomarker is a fecal biomarker. Fecal biomarkers are known in the art, see, e.g., Lehmann et al., *Ther. Adv. Gastroenterol.*, 8(1):23-26, 2015, herein incorporated by reference in its entirety. In some embodiments, the protein biomarker is produced and secreted by neutrophils in the intestinal mucosa in response to gastrointestinal inflammation, e.g., inflammation caused by IBD.

In some embodiments, the protein biomarker is calprotectin. Inflammation caused by IBD results in an influx of neutrophils to the intestinal mucosa of the gastrointestinal tract. Calprotectin is a 24 kDa dimer of calcium binding proteins S100A8 and S100A9. Calprotectin is a pro-inflammatory protein, and the concentration of calprotectin is proportional to the intensity of neutrophils in the gut mucosa. Elevated levels of faecal calprotectin indicates the migration of neutrophils to the intestinal mucosa, and can serve as a marker for intestinal inflammation caused by, for example, IBD, Crohn's Disease, or ulcerative colitis (see Lehmann et al., Ther. Adv. Gastroenterol., 8(1):23-26, 2015). Elevated levels of calprotectin can also be used to differentiate between IBD and IBS.

In some embodiments, the protein biomarker is S100A12. S100A12 is a specific neutrophilic protein that is upregulated during active IBD. Release of S100A12 from intestinal mucosa correlates with inflammation, and fecal levels of S100A12 can be used to diagnose IBD.

In some embodiments, the protein biomarker is lactoferrin. Lactoferrin is an iron-binding protein expressed by activated neutrophils, and mucosal epithelial cells. Elevated levels of faecal lactoferrin is indicative of inflammation in the gastrointestinal system caused by, e.g., chronic IBD, ulcerative colitis, and Crohn's disease (see Kane et al., *Am J Gastroenterol.* 98(6):1309-14, 2003; Lehmann et al., Ther. Adv. Gastroenterol., 8(1):23-26, 2015).

In some embodiments, the protein biomarker is M2-pyruvate kinase (M2PK). M2PK is a multifunctional protein that is present in undifferentiated and proliferating tissues. Fecal M2PK levels are increased in active IBD, and M2PK has been shown to be capable of differentiating between IBD and IBS.

In some embodiments, the protein biomarker is neopterin. Neopterin is an intermediate metabolite of biopterin that is released from macrophages. Levels of neopterin are higher in active IBD than in inactive disease, and neopterin concentration levels correlate with mucosal lesion severity.

In some embodiments, the protein biomarker is a metalloproteinase (MMP). Metalloproteinases belong to a family of zinc-dependent endopeptidases. MMPs such as MMP-9 are secreted by activated neutrophils in IBD, and in ulcerative colitis biopsies, MMP-1, MMP-2, MMP-3, and MMP-9 concentrations are elevated.

In some embodiments, the protein biomarker is a myeloperoxidase (MPO). Myeloperoxidases are lysosomal proteins that are released by activated neutrophils during inflammation.

In some embodiments, the protein biomarker is a polymorphonuclear elastase (PMN elasetase). PMN elastase is released by activated neutrophils, and subjects with active IBD have higher concentrations of fecal PMN elastase than subjects with IBS or inactive IBD.

In some embodiments, the protein biomarker is alpha 1 antitrypsin (A1A). A1A is a linear glycoprotein predominantly synthesized in the liver, but is also made by intestinal macrophages, monocytes and epithelial cells. A1A is resistant to degradation in the gut, and is a marker for intestinal protein loss and permeability. A1A concentration levels have been shown to be useful for evaluating and monitoring chronic inflammatory intestinal diseases.

In some embodiments, the protein biomarker is eosinophilic protein X (EPX). EPX is released from activated eosinophils, including in the gastrointestinal tract.

Protein preservatives can be used to prevent or reduce the rate of protein degradation or denaturation, and/or increase the stability of proteins, e.g., to maintain protein structure. Preservatives can include, by way of example, protease inhibitors, surfactants (e.g., nonionic surfactants), emulsifiers, acids, parabens, esters and protein stabilizers.

In some embodiments, the preservative can prevent or reduce the digestion or degradation of proteins by one or more proteases. In some embodiments, the preservative can be a protease inhibitor. In some embodiments, the protease inhibitor is a serine protease inhibitor, a metalloprotease inhibitor, an aminopeptidase inhibitor, a cysteine peptidase inhibitor, or an aspartyl protease inhibitor. In some embodiments, the protease inhibitor can prevent or reduce digestion by proteases such as, but not limited to, trypsin, chymotrypsin, plasmin kallikrein, thrombin, papain, cathepsin B, cathepsin L, calpain and staphopain, endoproteinase Lys-C, Kallikrein, and thrombin. In some embodiments, the protease inhibitor can be 4-(2-aminoethyl)benzenesulfonyl fluoride hydrochloride (AEBSF, CAS 30827-99-7), aprotinin (CAS 9087-70-1), bestatin (CAS 58970-76-6), E-64 (CAS 66701-25-5), leupeptin (CAS 103476-89-7), pepstatin A (CAS 26305-03-3), or N-p-Tosyl-L-phenylalanine chloromethyl ketone (TPCK). In some embodiments, the protein biomarker preservative includes 4-(2-aminoethyl)benzenesulfonyl fluoride hydrochloride (AEBSF, CAS 30827-99-7), aprotinin (CAS 9087-70-1), bestatin (CAS 58970-76-6), E-64 (CAS 66701-25-5), leupeptin (CAS 103476-89-7), pepstatin A (CAS 26305-03-3), DMSA, and bovine serum albumin, and, optionally, N-p-Tosyl-L-phenylalanine chloromethyl ketone (TPCK).

In some embodiments, the preservative can be a protein stabilizer such as, for example, Trehalose or Dextran.

A preservative as disclosed herein can be an acid. In some embodiments, the preservative can be an acid with a pKa between 3 and 7. In some embodiments, the preservative can be citric acid, or sorbic acid.

In some embodiments, the preservative can be a surfactant such as a polysorbate. Exemplary polysorbates include, for example, polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), sorbitan monolaurate, sorbitan monopalmitate, sorbitan monostearate, sorbitan tristearate, and sorbitan monooleate.

In some embodiments, the preservative is a paraben, parahydroxybenzoate, or ester of parahydroxybenzoic acid (4-hydroxybenzoic acid). In some embodiments, the preservative can be propyl paraben.

In some embodiments, the preservative can include dimethyl sulfoxide (DMSA). In some embodiments, the preservative can include bovine serum albumin.

The preservative can be a mixture of two or more of a protease inhibitor, a surfactant, an emulsifier, an acid, a paraben, and an ester. For example, a preservative as described herein can include a mixture of two or more protease inhibitors. In some embodiments, a preservative as described herein can include a mixture of one or more protease inhibitors, and one or more acids. In some embodiments, a preservative as described herein can include a mixture of one or more protease inhibitors, one or more acids, and an ester, e.g., a paraben. In some embodiments, a preservative as described herein can include a mixture of one or more protease inhibitors, one or more acids, one or more esters, and one or more surfactants. In some embodiments, the preservative can include the HALT™ protease inhibitor cocktail (Thermo Fisher). In some embodiments, the preservative can include the HALT™ protease inhibitor cocktail (Thermo Fisher) and TPCK. In some embodiments, the preservative can be bactericidal to preserve a protein biomarker. In some embodiments, the preservative mixture that is bactericidal includes citric acid (CAS 77-92-9), sorbic acid (CAS 110-44-1), propylparaben (CAS 94-13-3), tween 80 (CAS 9005-65-6), ethanol, bovine serum albumin, and TPCK (CAS 402-71-1).

In some embodiments, a preservative mixture containing one or more protease inhibitors can be contacted with a protein in the gastrointestinal tract to stabilize the protein. In some embodiments, the protein is an immunoglobulin. In some embodiments, the protein is an IgA or IgM. In some embodiments, the protein is a secretory IgA. In an exemplary embodiment, a preservative mixture containing AEBSF, aprotinin, bestatin, E-64, leupeptin and pepstatin A protease inhibitors (HALT™, Thermo Fisher), and N-p-Tosyl-L-phenylalanine chloromethyl ketone (TPCK, Sigma Aldrich) can be used to stabilize one or more immunoglobulin proteins in the gastrointestinal tract, e.g., secretory IgA.

In some embodiments, a preservative mixture containing one or more protease inhibitors, acids, parabens, and surfactants can be contacted with a protein in the gastrointestinal tract to stabilize the protein. In some embodiments, the protein is not an immunoglobulin. In an exemplary embodiment, a preservative mixture containing AEBSF, aprotinin, bestatin, E-64, leupeptin and pepstatin A protease inhibitors (HALT', Thermo Fisher), N-p-Tosyl-L-phenylalanine chloromethyl ketone (TPCK, Sigma Aldrich), citric acid, sorbic acid, propyl paraben, polysorbate 80 (Tween 80), BSA can be used to stabilize one or more non-immunoglobulin proteins in the gastrointestinal tract, e.g., a cytokine, calprotectin, S100A12, lactoferrin, M2-pyruvate kinase, neopterin, a metalloproteinase, a myeloperoxidase, polymorphonuclear elastase, and/or alpha 1 antitrypsin eosinophilic protein X.

In some embodiments, one or more internal controls are included in an ingestible device, as described herein, that is used to collect one or more biomarker analytes. The internal control can be used to monitor the stability and degradation of small molecules, nucleic acids, and/or proteins in the device over time. In some embodiments, the internal control can be a small molecule, a nucleic acid, and/or a protein. In some embodiments, the small molecule internal control can be 2,4 dinitrophenol (2,4, DNP), femocene, and/or a deuterium-labeled cholesterol. In some embodiments, the nucleic acid internal control can be a DNA internal control. In some embodiments, the nucleic acid internal control can be a RNA internal control. In some embodiments, the RNA internal control can be a G+C-rich (60%) RNA molecule with extensive secondary structure, based on a modified delta virus genome, as described in Dingle et al., J. Clin. Microbiol. 42(3):1003-1011, 2004, herein incorporated by reference in its entirety. In some embodiments, the protein internal control can be human serum albumin (HAS), fluorescein isothiocyanate, and/or biotin.

Microbial Preservatives

The devices and methods disclosed herein can also be used to collect a sample of microbial cells, e.g., bacterial cells, in the gastrointestinal (GI) tract of a subject, and the sampled cells can be analyzed to identify and quantify the cells. In some embodiments, the ingestible devices and methods disclosed herein use one or more preservatives that stabilize bacterial cells collected in the device, so that once the device exits the subject's body, an accurate assessment can be made as to the identity and number of bacteria present at the location of the GI tract where the bacteria were collected. The ingestible devices and methods disclosed herein can provide representative microbiome data at the site of bacterial cell collection in the GI tract.

Any microbe present in the gastrointestinal tract can enter an ingestible device as described herein. The microbe can be a bacterium, a fungus, or a protest. In exemplary embodiments, at least one bacterium enters an ingestible device as described herein. In some embodiments, the microbe is part of the normal microflora of the gastrointestinal tract. In some embodiments, analysis of the microbes that have collected in the ingestible device can provide information about the microflora of the gastrointestinal tract that can be predictive about the health of the gastrointestinal tract, and/or diagnose or predict a disorder of the gastrointestinal tract. For example, information about the abundance of certain types of bacteria relative to the bacteria present in a control sample, e.g., a sample from a subject with a healthy gastrointestinal tract, can be used to diagnose or predict a disorder, such as an inflammatory disorder. In some embodiments, a taxonomic shift in bacteria, or change in the abundance of certain types of bacteria, relative to the microbiome of a healthy subject can be used to predict a disease or disorder of the gastrointestinal tract, e.g., Crohn's disease, inflammatory bowel disease, ulcerative colitis, irritable bowled syndrome, or small intestinal bacterial overgrowth (see, e.g., Wright et al., Inflamm. Bowel Dis. 21(6):1219-1228, 2015; Kostic et al., Gastroenterology 146(6):1489-1499, 2014; Sartor and Mazmanian, Am. J. Gastroenterol. Suppl. 1:15-21, 2012). In some embodiments, at least one type of bacteria associated with an inflammatory and/or autoimmune disease of the gastrointestinal tract can be collected in the ingestible device.

As used herein, the terms "stabilize" or "stabilized" means that the cells remain in the same state or in a similar state as when they were collected in a device as described herein until the cells are later analyzed, such that the overall identity and number of cells has not changed or has changed little compared to when the cells were collected. As a result, the cells collected in the device are representative of the population of cells present at the site of collection, e.g., provide accurate cell counts found at the site of collection.

The devices and methods disclosed herein overcome challenges associated in deriving information about the microbiome based on the sampling of bacteria in the GI tract. A significant challenge in sample analysis is the delay that occurs between the sampling of bacteria in the GI tract using an ingestible device, e.g., the small bowel, and the recovery of the device once it exits the subject's GI tract. During this period of time, the bacterial samples are exposed to temperatures and conditions that facilitate the growth and multiplication of certain bacteria strains, while eliminating of other types of bacteria. As a result, once the ingestible device leaves the body, certain types of bacteria in the population present in the device, such as anaerobic strains, may be overrepresented relative to other types of bacteria, and the overall numbers of bacteria may not be representative of the population present in the GI tract. The devices and methods disclosed herein overcome this challenge by using preservatives to stabilize the bacteria population collected in the device, so that the types and numbers of bacteria present in the device after it exits the body are similar to the types and numbers of bacteria that were initially collected in the device in the GI tract.

In some embodiments, a sample of bacterial cells collected in an ingestible device is contacted with a preservative that stabilizes the bacteria sample, so that the sample can provide accurate information about the identity and cell count of bacteria for at least 30 days after the sample was collected. In some embodiments, a sample of bacterial cells can be collected and stabilized an ingestible device as disclosed herein, so that the sample can provide accurate information about the identity and cell count of bacteria for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In some embodiments, a sample of bacterial cells can be collected and stabilized in a device as disclosed herein, so that the sample can be provide accurate information about the identity and cell count of bacteria found at the site of collection after the device has transited through the GI tract, and has been recovered and analyzed.

Bacteria can be collected by a device as described herein in any location within the gastrointestinal tract of a subject. In some embodiments, bacterial cells are collected in two or more locations within the GI tract. In some embodiments, bacterial cells are collected in the upper gastrointestinal tract of a subject. In some embodiments, bacterial cells are collected in the large intestine. In some embodiments, the bacterial cells are collected in the small intestine. In some embodiments, bacterial cells are collected in the duodenum of a subject. In some embodiments, bacterial cells are collected in the jejunum of a subject. In some embodiments, bacterial cells are collected in the ileum of a subject. In some embodiments, bacterial cells are collected in the duodenum and the jejunum of a subject.

In some embodiments, a sample of bacterial cells is collected in the GI tract of a subject having, or suspected of having, small intestinal bacterial overgrowth (SIBO). SIBO results from excessive bacteria in the small intestine. Subjects having SIBO can vary in the presentation of disease. Symptoms can be mild in some subjects, resulting in indigestion and bloating, to more severe, causing chronic diarrhea, weight loss, and malabsorption. SIBO is often associated with another illness that affects the functioning of the small intestine, including disorders that affect the motility or movement of the small bowel, and disorders that affect the immune system, such as, but not limited to, irritable bowel syndrome, Crohn's disease, and achlorhydria. SIBO diagnosis involves an accurate quantification of cells found in a sample collected from the small intestines. A count of more than 1×105 CFU of bacteria in a fresh sample collected from the small intestines using endoscopy indicates the presence of SIBO.

In exemplary embodiments, the preservative prevents, inhibits, or reduces the growth and/or multiplication of bacteria. In some embodiments, the preservative permanently prevents, inhibits, or reduces the growth and/or multiplication of bacteria. In some embodiments, the preservative is one or more of a bacteriostatic, bacteriocidal, and/or fixative compound.

Bacteriostatic preservatives arrest the growth or multiplication of the bacteria. In some embodiments, the preservative kills the bacteria, thereby preventing growth and multiplication. Bactericidal kill bacteria. Bacteria enter a device as described herein in the GI tract of a subject, and are contacted with a bacteriostatic preservative that arrests bacterial growth and multiplication, or a bactericidal preservative that kills the bacteria. As a result, the numbers of bacteria in the device are representative of the bacterial microflora that was present in the GI tract at the time the bacteria first entered the device.

In some embodiments, the preservative can be a bacteriostatic food preservative, such as, but not limited to, sorbic acid, citric acid, propyl paraben, nisin, dimethyl dicarbonate, and ethylenediaminetetraacetic acid (EDTA). In some embodiments, the preservative can be sodium azide, hydroxyurea, fusidic acid, diazolidinyl urea, imidazolidinyl urea, salicylic acid, barium and nickle chloride, metallic copper, thimerosal, 2-phenoxyethanol, or ProClin™. In some embodiments, the preservative can be one or more of sorbic acid, citric acid, propyl paraben, nisin, dimethyl dicarbonate, ethylenediaminetetraacetic acid (EDTA), sodium azide, hydroxyurea, fusidic acid, diazolidinyl urea, imidazolidinyl urea, salicylic acid, barium and nickle chloride, metallic copper, thimerosal, 2-phenoxyethanol, and ProClin™.

In some embodiments, the preservative prevents or reduces nucleic acid degradation, in addition to preventing or inhibiting the growth and/or multiplication of bacteria. The preservation of nucleic acid integrity allows for the quantification of bacteria using PCR-based DNA or RNA analysis methods, e.g., 16S ribosomal RNA PCR and sequencing. In some embodiments, the preservative includes EDTA.

In some embodiments, the bactericidal preservative can include one or more of citric acid (CAS 77-92-9), sorbic acid (CAS 110-44-1), propylparaben (CAS 94-13-3), Tween 80 (CAS 9005-65-6), ethanol, bovine serum albumin, and TPCK (CAS 402-71-1). In some embodiments, the bactericidal preservative is a mixture of citric acid, sorbic acid, propyl-paraben, and Tween 80, e.g., the bactericidal preservative can include 2.5% (m/v) citric acid, 2.5% (m/v) sorbic acid, 2.5% (m/v) propyl-paraben), and 3.13% (m/v) Tween 80. In some embodiments, the bactericidal preservative is a mixture of sorbic acid, Tris, EDTA, Tween 80, and NaCl, e.g., the bactericidal preservative can include 2.0% (m/v) sorbic acid, tris, EDTA, 1.0% (m/v) Tween 80, and 1.0% (m/v) NaCl. In some embodiments, the bactericidal preservative is a heavy metal bactericidal mixture. In some embodiments, the bactericidal preservative is a mixture that includes barium chloride and nickel chloride. In some embodiments, the bactericidal preservative is thimerosal, e.g., a stabilizer that includes 0.1% thimerosal.

Bacterial cells collected and stabilized in an ingestible device as disclosed herein can be analyzed using materials and methods that are well-known in the art to identify and/or count the number of bacteria in a sample to obtain representative microbiome data at the site of collection. In some embodiments, 16S ribosomal RNA sequencing is used to analyze the bacteria stabilized and collected in the apparatus or device. Various methods of 16S ribosomal sequencing are known in the art, and can be used to analyze bacterial samples as described herein (see, e.g., Sanschagrin and Yergeau, J. Vis. Exp. 90:51709, 2014).

In some embodiments, bacterial cells collected and stabilized in an ingestible device can be counted and/or identified, and compared to bacterial cells obtained by endoscopic sampling, e.g., from small intestine aspirates obtained by endoscopy, such as duodenal aspirates. In some embodiments, bacterial cells are collected and stabilized from a subject having SIBO or suspected of having SIBO using an ingestible device as described herein, and the number of bacteria in the device is counted and compared to a control sample collected from the small intestine of a subject through endoscopy. The control sample can be a negative control, i.e., collected from a subject who is known not to have SIBO, or a positive control, i.e., collected from a subject known to have SIBO. A count of more than $1 \times 10^5$ CFU is considered SIBO when assessed on fresh samples collected through endoscopy.

EXAMPLES

Materials

Simulated Duodenal Juice ("SDJ"): SDJ was formulated by adding 2.5 mL of a first solution ("Solution 1") to 10 mL of a second solution ("Solution 2"). Solution 1 contained nine mg Pancreatin (Sigma Aldrich Cat. No. P1750), 65 mg bovine (ox) bile (Sigma Aldrich Cat. No. B3883), and 10 mL saline. Solution 2 contained five mg mucin (Sigma Aldrich Cat. No. M2378), and 10 mL saline. After mixing Solution 1 and Solution 2, the pH was adjusted to 6.5 to reflect the mean pH in fasting duodenal fluid samples. SDJ stock was aliquoted into sterile 15 mL conical tubes and frozen at −80° C. On each day of experimentation, SDJ stock was thawed at room temperature and used within 1 hour.

HALT Protease Inhibitor Cocktail: 100×HALT™ Protease inhibitor cocktail (Thermo Fisher Cat. No. 78430).

TPCK: TPCK (Sigma Aldrich Cat. No. T4376). 30 mM stock solution in 100% ethanol.

Cidal Mix 1 (CM1) stock solution: citric acid (Sigma Aldrich Cat. No. 251275), 50% stock w/v solution in water; sorbic acid (Sigma Aldrich Cat. No. S1626), 10% stock w/v solution in 100% ethanol; propyl paraben (Sigma Aldrich Cat. No. PHR1010), 33% stock w/v solution in 100% ethanol; and Tween® 80 (Sigma Aldrich Cat. No. P1754).

Bovine Serum Albumin (BSA): BSA (Proliant Cat. No. 7500802 Lot 12G54003). 1% stock w/v in PBS or water.

Immunoglobulin Preservative Solution: 4 mL solution containing 1×HALT, 20 µM TPCK in 1% BSA prepared by combining 40 µL 100×HALT, 2.66 µL 30 mM stock TPCK (Sigma Aldrich Cat. No. T4376), and 3.95 mL sterile distilled water containing 1% BSA.

Cytokine Preservative Solution: 4 mL solution containing 1×HALT, 0.3% cidal mix, 20 µM TPCK and 1% BSA prepared by combining 24 µL citric acid stock, 120 µL sorbic acid stock, 36 µL propyl paraben, 125 µL Tween® 80, 40 µL 100×HALT™, 2.66 µL 30 mM stock TPCK, and 3.65 mL sterile distilled water containing 1% BSA.

Absorbent Material: Carwild Ivalon PVA (P4) sponge shaved to 1.3+/−0.1 mm and cut to 6 mm×8.5 mm.

Protein Analytes (purified standards): Recombinant human IL6 (R&D systems Cat. No. 7270-IL025); IgA from human serum (Sigma Aldrich Cat. No. I1010-5MG); IgM from human colostrum (Sigma Aldrich Cat. No. 18260-5MG); and FITC-HSA-Biotin (Nanocs Cat. No. HS2—BNFC).

Extraction buffers: Epitope Diagnostics Inc. (from Quantitative fecal Calprotectin ELISA kit Cat. No. KT-849); and HyCult Biotech Extraction buffer (from Calprotectin Human ELISA kit Cat. No. HK379-02).

ELISA kits: Human IL6 Quantikine ELISA Kit (R&D systems Cat. No. D6050); Human IgA ELISA kit (Abcam Cat. No. ab196263); Human IgM ELISA kit (Abcam Cat. No. ab214568); and Internal Control ELISA Assay (Developed internally)

Internal Control protein: FITC-HSA-Biotin (Nanocs Cat. No. HS2—BNFC). 400 ug/mL working stock in filter sterilized PBS containing 0.1% BSA Blocking reagent: SuperBlock (PBS) Blocking Buffer (Thermo Fisher Cat No. 37515)

Capture antibody: Pierce Fluorescein Isothiocyanate Antibody (Thermo Fisher Cat No.: MIF2901). 10 µg/mL working stock in filter sterilized PBS.

Assay Diluent: BSA in filter sterilized PBS at 1% w/v.

Detection reagent: Pierce High Sensitivity Streptavidin—HRP (Thermo Fisher Cat No. 21130). 1:10,000 working stock in Assay Diluent.

Substrate reagent: QuantaRed Enhanced Chemifluorescent HRP Substrate (Thermo Fisher Cat No. 15159), prepared as indicated in product literature.

Wash Buffer: Tween 20 at 0.01% v/v in filter sterilized PBS.

HABA Biotin Blocking Solution: 825 µM working stock in ethanol.

Methods

Test wells were blocked with phosphate buffered saline (PBS) containing 1% BSA and plates were incubated at 4° C. for one. Wells were subsequently washed four times with PBS containing 0.01% Tween20. After washing, neat SDJ or heat-treated SDJ (both containing 1×HALT) was added to the test wells and spiked with IgA (2500 ng/ml), IgM (1250 ng/ml), or IL6 (30 ng/ml) in 0.1% BSA. 20 µl samples were harvested immediately after analyte addition. Samples were diluted 1:50 in each extraction buffer and centrifuged at 10,000×g for 20 minutes at 4° C. For IL6 detection, 100 µl supernatant was diluted 1:2 in ELISA diluent buffer. For IgA and IgM, 50 µl of extracted supernatant was diluted with 50 µl of antibody cocktail according to the IgA and IgM ELISA protocol. Experiments used neat SDJ (untreated) or heat-treated at 100° C./15 min (to eliminate heat-liable components that may hinder analyte detection in SDJ).

Commercially available human IL6, IgA and IgM ELISA kits were used to detect these analytes according to the manufacturer's instructions.

To detect IC, an ELISA assay was developed de novo. IC was an HSA protein conjugated to both FITC and Biotin. The rationale for using this protein was to capture/immobilize the IC protein via the FITC tag and then use the Biotin tag for detection.

The following describes the preparation of an internal control standard curve in duplicate. IC stock solution for these experiments (Nanocs Cat No. HS2-BNFC) was at 4 mg/ml. IC standard concentration range was 0 to 30,000 ng/mL.

Figure 35:
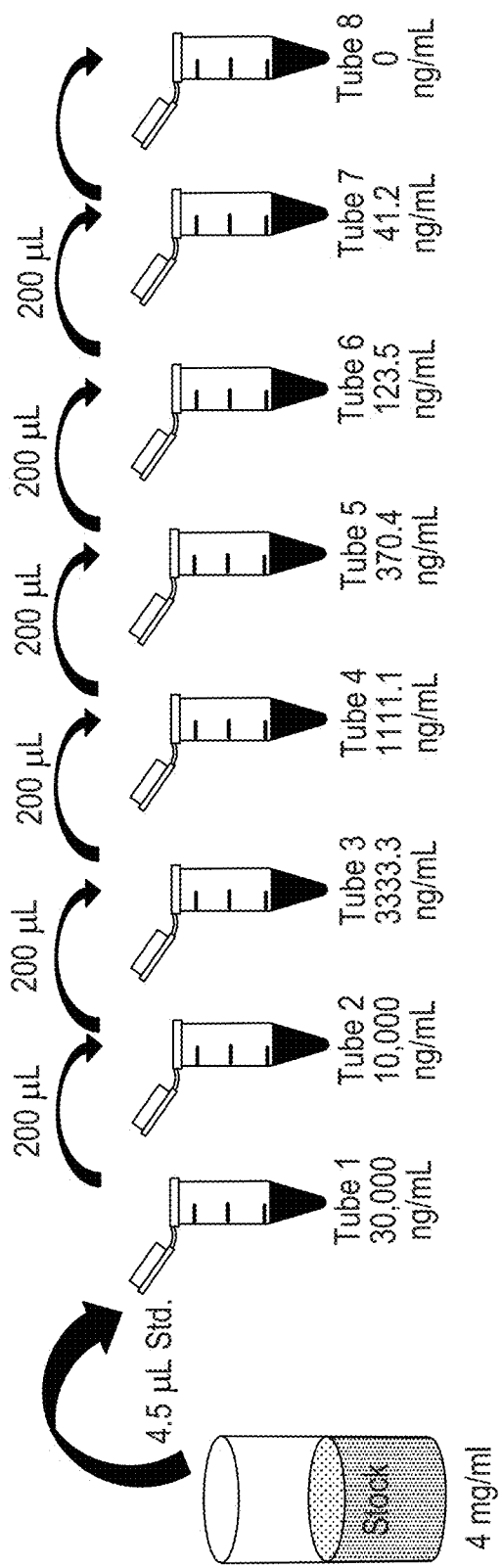
FIG. 35 depicts a dilution series.

1.) Label 8 tubes: standards 1-8.
2.) Add 595.5 µl of 1×PBS+1% BSA into tube 1. Add 400 µl of 1×PBS+1% BSA into the remaining tubes labeled 2-8.
3.) Pipette 4.5 µl of 4 mg/mL stock HSA stock solution into tube 1. This will serve as the highest concentration at 30.00 ng/mL of the standard curve. Prepare a 1:3 dilution series, as shown in FIG. 35. Mix each tube thoroughly before the next transfer. The 1×PBS+1% BSA solution serves as the zero standard.

The wells were coated with capture antibody as follows. The anti-FITC antibody was diluted to 10 µg/mL in PBS. 100 µL per well was plated in an ELISA plate. The plate was incubated at room temperature for 2 hours on a plate shaker set to 45 rpm or overnight at 4° C.

The wells were blocked as follows. SuperBlock blocking buffer was used to wash and block wells. Three exchanges of 300 µl were performed, flicking the plate contents into sink and knocking the plate on a hard surface to remove excess liquid. Incubation was not used with SuperBlock because blocking was immediate. SuperBlock was left in the wells until the samples and controls were ready for plating.

The samples and protein standards were added as follows. 100 µL of sample (or protein standard) was pipetted into each well in duplicate. For a positive control, FITC-HSA-Biotin was diluted to 1 µg/ml into 1×PBS+1% BSA. 1 ml of 0.5 µg/mL FITC-HSA-Biotin was prepared as follows. A working stock of HSA protein was prepared by diluting 1:10 of the initial stock solution of 4 mg/mL of protein to produce 0.4 mg/ml. 2.54 of 0.4 mg/mL HSA was added to an Eppendorf tube and the volume was brought up to 1 ml with 1×PBS+1% BSA. The plate was sealed and incubated for 2.5 hours at room temp on a plate shaker set to 45 rpm.

The plate was washed as follows. Each well was aspirated or emptied by inverting the plate and shaking the contents over a sink. The plate was blotted against clean paper towels to remove excess liquid. The plate was washed four times by adding 300 µl of 1×PBS+0.01% Tween 20. Liquid was completely removed at each step by blotting plate against clean paper towels.

Detection reagent and HABA were added as follows. Streptavidin-HRP was diluted in 1:10,000 in PBS+1% BSA with 20 µM HABA reagent and added 100 µl per well. For a full 96-well plate, 10 ml of diluted Streptavidin-HRP was prepared by pipetting 1 µl of Streptavidin-HRP stock solution (4.13 mg/ml) and 85 µl into 10 ml of 1×PBS+1% BSA. If less detection reagent was used, the appropriate volume was prepared for the number of samples being tested. The plate was incubated for hours at room temperature on a plate shaker set to 45 rpm.

HRP substrate was added as follows. The plate was washed once with 300 µl 1×PBS 0.01% Tween 20. The plate was washed three times with 300 µl 1×PBS only (ensure there is no Tween 20 in the wells before adding substrate because it could cause a high background signal). The substrate mix was made as follows. If, for example, 100 µl substrate was added to each well and there were about 100 wells, then this generated a solution of 10 ml. To prepare 10 ml of substrate solution, 5 ml of Enhancer solution, 5 ml of Stable Peroxide and 100 µl of ADHP were added to a 15 ml falcon tube. 100 µl of substrate was added and incubated for 15 minutes at room temperature on a plate shaker set at 45 rpm. A reading was made on GloMax in absorbance mode at 560 nm, then on fluorescence mode Emission 580-640, Excitation Filter 520 nm. The reaction was stopped with 10 µl stop solution and re-read, as appropriate.

Figure 36:
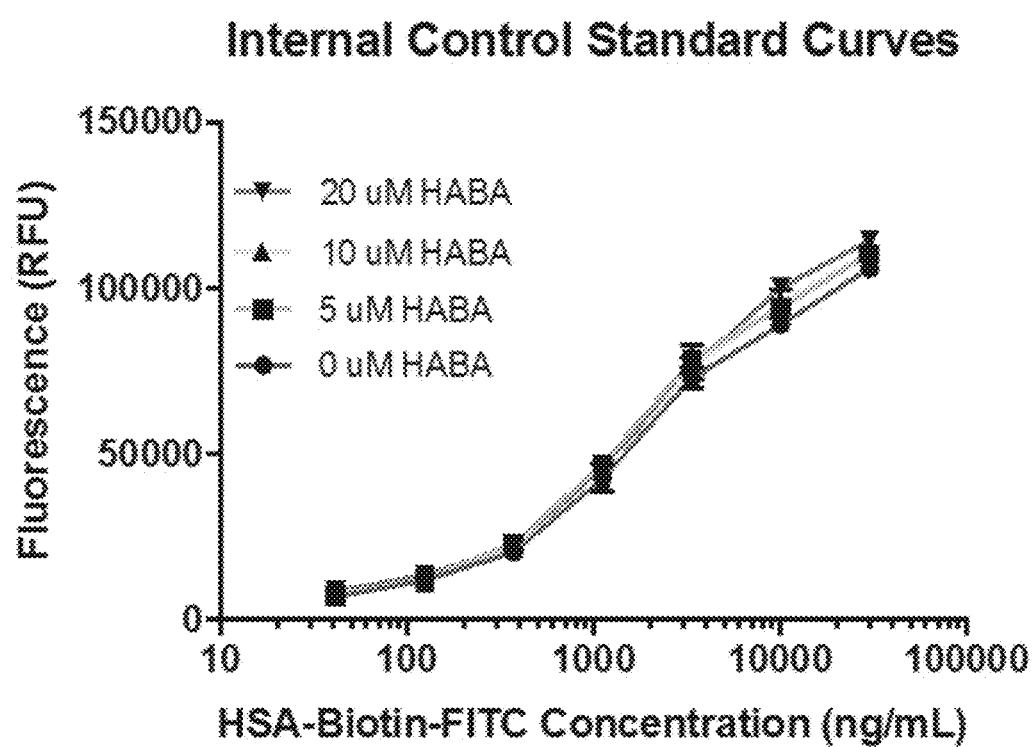
FIG. 36 shows ELISA data.

The internal control ELISA reagents and equipment were as follows.
BSA (Lampire Biological Laboratories Cat No. 7500804)
PBS, pH 7.4 (Thermo Cat No. 10010-023)
Tween® 20 (Sigma Cat No. P9416)
Reagent grade ethanol
Nunc-Immuno™ MicroWell™ 96 well solid plates, Max-iSorp™ (Thermo Fisher Cat No. 442404)
300 µl 8-channel pipettor
10 µl 8-channel pipettor
Single channel pipettors
Pipet tips
Reagent reservoirs
Light protective plate seals (TempPlate EXT Sealing Foil, USA Scientific Cat No. 2998-7100)
Orbital plate shaker The effects of varying concentrations of HABA on detection of IC protein were investigatged using a standard concentration curve. During the detection phase of the IC ELISA either 0, 5, 10, 20 µM HABA was mixed with Streptavidin-HRP. As shown in FIG. 36, the IC ELISA was functional and adding 2004 HABA improved IC signal detection.

Here, the method that was used for detecting IC after exposure to SDJ is described. The impact of the presence of protein preservatives used to detect IgA, IgM and IL6 in SDJ interfered with the IC ELISA detection. The stability of IC in SDJ following incubation at 37° C. for 72 hours was investigated.

Initially test wells were blocked with PBS containing 1% BSA to prevent IC protein from binding to the plastic surface on the test plate. Plates were incubated at 4° C. for 1 hour. Wells were subsequently washed 4× with PBS containing 0.01% Tween20. 100 µl of SDJ containing PBS only or 1×HALT−/+0.15% Cidal Mix 1 in PBS containing 1% BSA was spiked with 5 µg FITC-HSA-Biotin. 20 µl samples were taken at time 0 (immediately after analyte addition) and again after incubation at 37° C. for 72 hours. Samples were diluted 1:50 in Epitope extraction buffer and centrifuged at 10,000×g for 20 minutes at 4° C. The supernatant was assayed for the presence of IC by ELISA (as described above).

Figure 37:
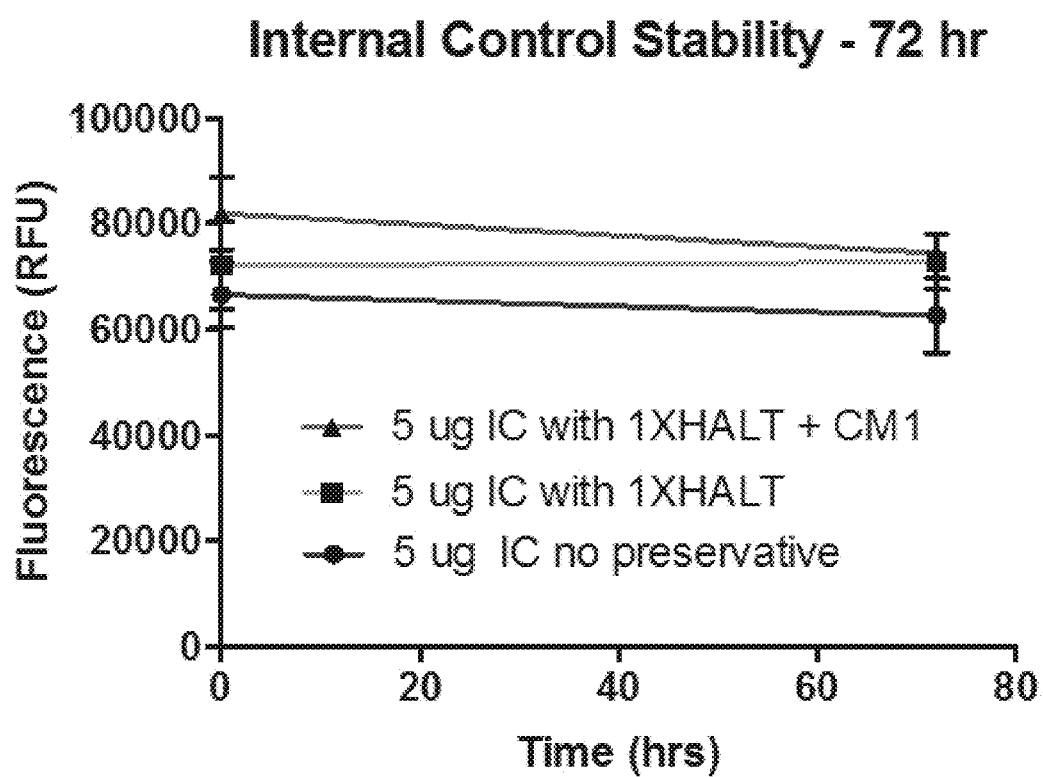
FIG. 37 shows ELISA data.
Figure 38:
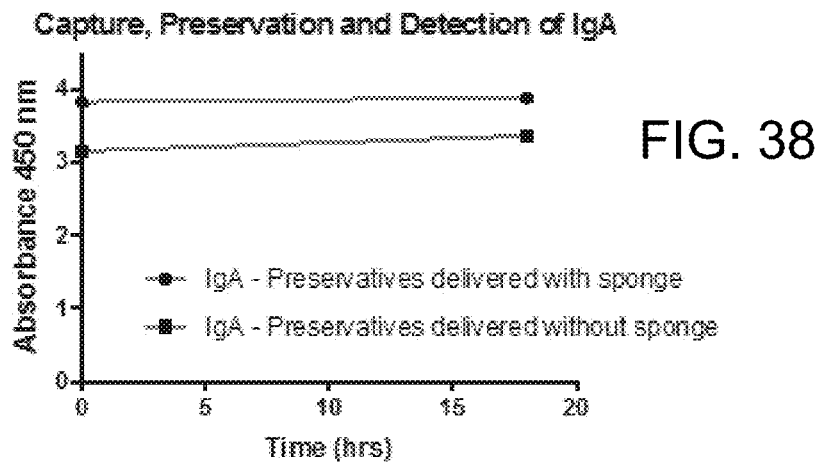
FIG. 38 shows ELISA data.
Figure 39:
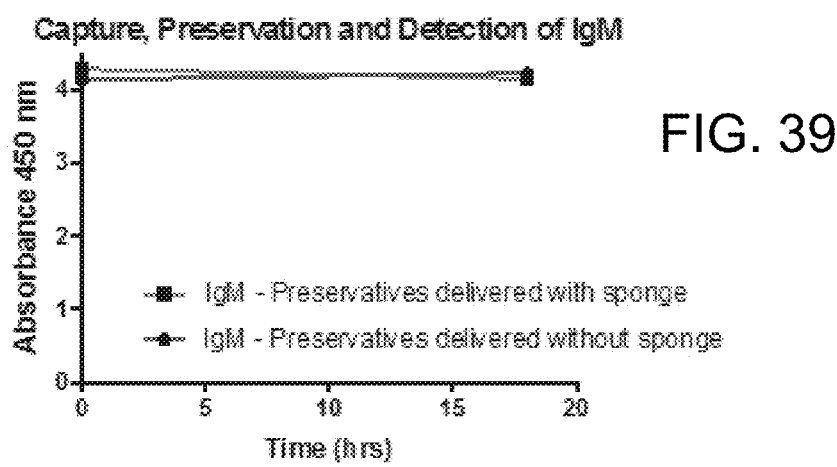
FIG. 39 shows ELISA data.
Figure 40:
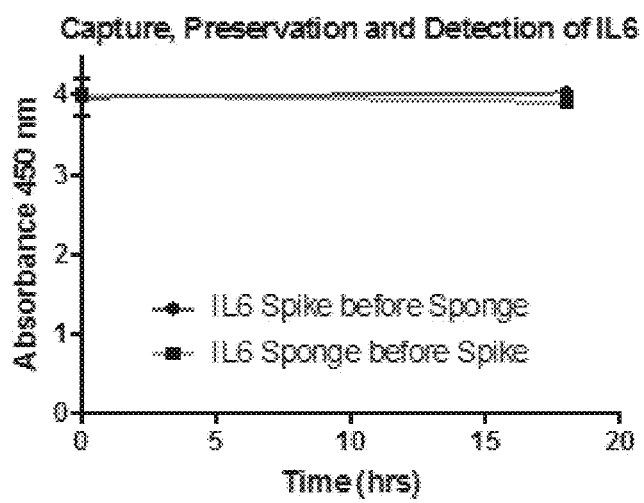
FIG. 40 shows ELISA data.

Results are depicted in FIG. 37. Epitope extraction buffer was effective at extracting IC from SDJ to enable detection of IC by ELISA. Detection of IC by ELISA was not significantly hindered by the presence of analyte preservatives in SDJ. The IC protein was relatively stable in SDJ and could be detected by ELISA following incubation at 37° C. for 72 hours.

Capturing and Preserving Biomarkers

A test system was established to investigate delivery of protein preservatives to a biorelevant surrogate matrix, which was SDJ. A two-step process was developed to load the absorbent material (see above) with preservative chemistries involved for analyte preservation. First, absorbent material was submerged in either 4 mL of Immunoglobulin Preservative Solution, see Section 5 for the preservation of IgA and IgM proteins in SDJ, or absorbent material was submerged in 4 mL of Cytokine Preservative Solution for the preservation of IL6. The absorbent material was soaked in preservative solution until saturation (five minutes). The absorbent material was removed and dried overnight at room temperature in a vacuum oven. Following drying, a tripartite internal control (IC) molecule including Fluorescein isothiocyanate conjugated to human serum albumin conjugated to Biotin (FITC-HSA-Biotin) was pipetted on top of the preservative-loaded absorbent material. Again, the absorbent material was dried overnight at room temperature in a vacuum oven. This served as a control protein during biomarker detection. The internal control was used to monitor any protein degradation process that may occur inside an ingestible as it transits the gut. In the experiments described here, the IC was applied to each absorbent material in a known amount prior to exposure to SDJ, then assayed after varied lengths of time thereafter. Through this method it was envisioned that the loss of the IC could be used as a marker for general protein degradation. The kinetics of degradation can be derived and used to back calculate/estimate the starting concentrations of other biomarkers of interest.

The following experiments demonstrate effective delivery of protein preservatives into SDJ matrix using the absorbent material. Experiments were set up as follows. Test wells were blocked with PBS containing 1% BSA to prevent protein analytes from binding to the plastic surface on the test plate. Plates were incubated at 4° C. for one hour. Wells were subsequently washed 4× with PBS containing 0.01% Tween20. The absorbent material loaded with Immunoglobulin Preservative Solution was submerged in 100 µL SDJ after the SDJ was spiked with IgA (2500 ng/ml) and IgM (1250 ng/ml). The absorbent material soaked in Cytokine Preservative Solution was submerged into SDJ either before or after spiking IL6 (1 µg/mL). SDJ containing optimum preservatives (in the absence of absorbent material) was spiked with IgA or IgM as positive controls. 20 µL samples were taken at time 0 (immediately after analyte and absorbent material addition) and again after incubation at 37° C. for 18 hours. Samples were diluted 1:50 in Epitope extraction buffer and centrifuged at 10,000×g for 20 minutes at 4° C. For IL6 detection, 100 µl of supernatant was diluted 1:2 in ELISA diluent buffer. For IgA and IgM detection, 50 µl of extracted sample was incubated with 50 µl of ELISA cocktail antibody according to the ELISA kit instructions.

It was determined that successful detection of IgA and IgM in SDJ was achieved using 1% BSA and 100×HALT only, and that successful detection of IL6 was achieved using 1% BSA, 100×HALT and 0.3% CM1.

The foregoing experiments were repeated with the 20 µL samples taken at time 0 (immediately after analyte and absorbent material addition) and again after incubation at 37° C. for 24 hours, 48 hours and 72 hours.

Figure 41:
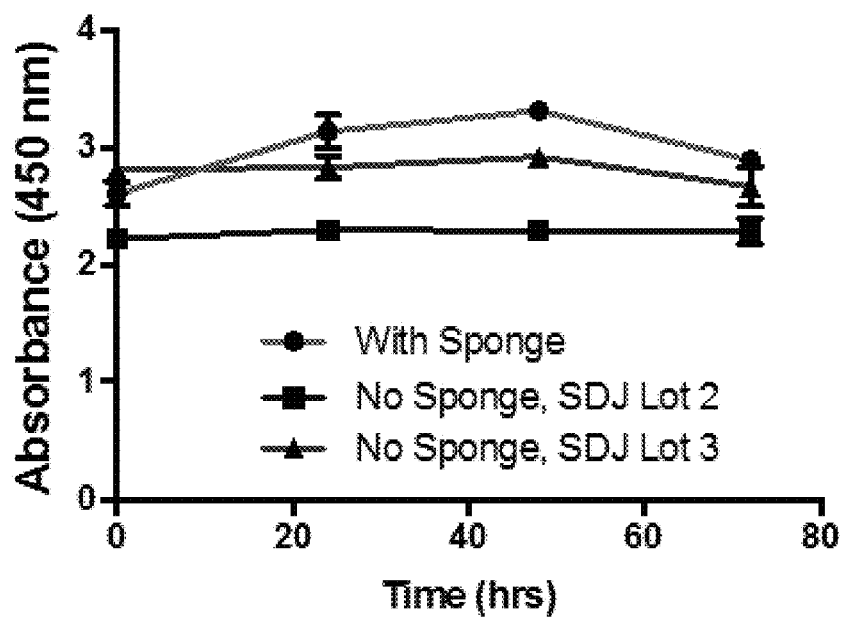
FIG. 41 shows ELISA data.
Figure 42:
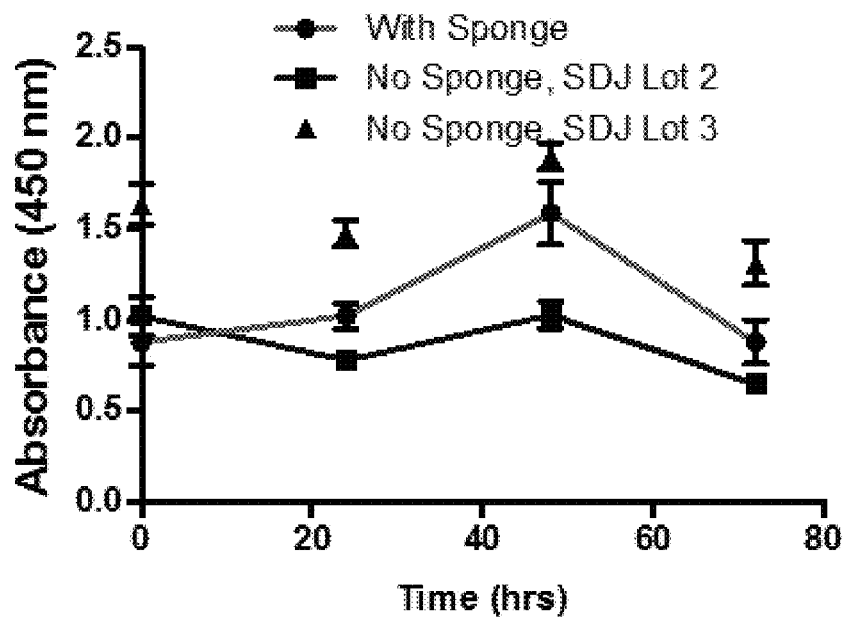
FIG. 42 shows ELISA data.
Figure 43:
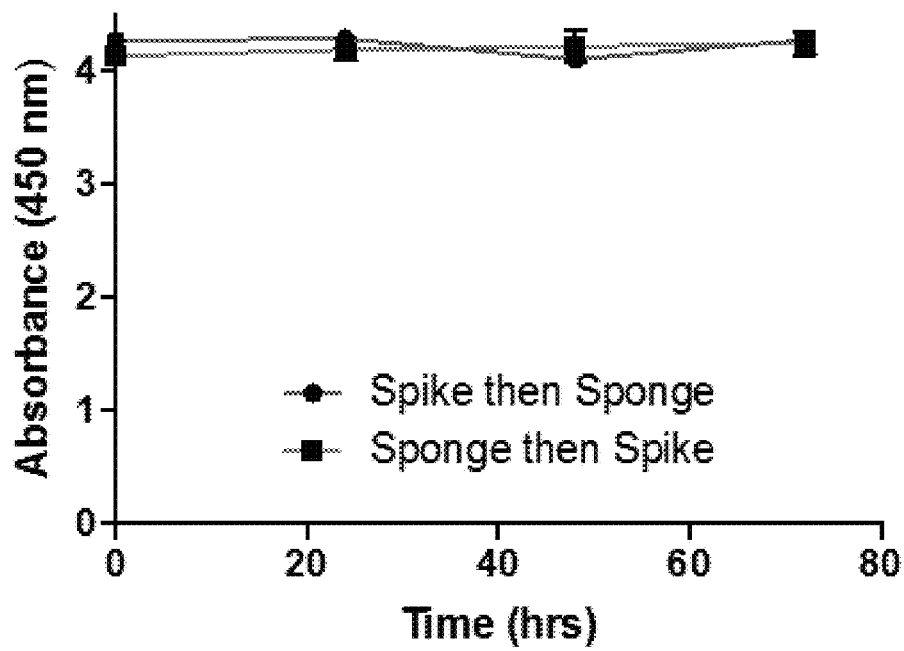
FIG. 43 shows ELISA data.
Figure 44:
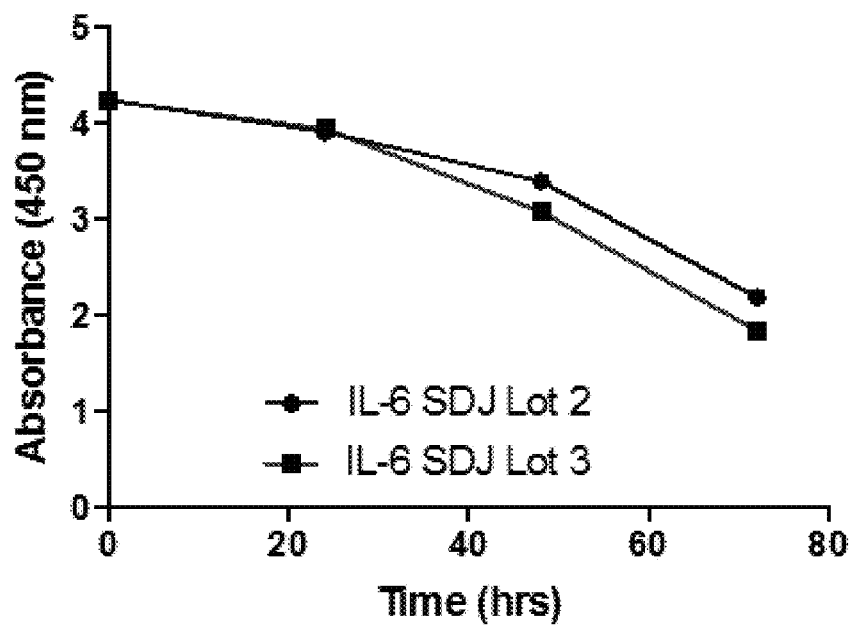
FIG. 44 shows ELISA data.

FIGS. 38-43 show that: 1) the absorbent material was successfully loaded with preservative mixes; 2) the preservative mixes were successfully delivered to a biorelevant matrix; 3) protein biomarkers were preserved for up to 72 hours by the preservative mixes; and 4) the absorbent material did not irreversibly bind to the biomarkers. FIGS. 41, 42 and 44 demonstrate consistency of biomarker preservation across two different lots of SDJ.

ELISA Assay Compatibility

ELISA assays can be very sensitive and relatively complex immunoassays that can be negatively impacted by certain conditions. For example, an upstream component to an assay could inhibit or alter results. These experiments were performed to characterize the impact of preservative cocktails on downstream biomarker assay methods and prompted a strategy of capturing materials for the immunoglobulin tests and the IL6 test in separate ingestible devices.

Figure 45:
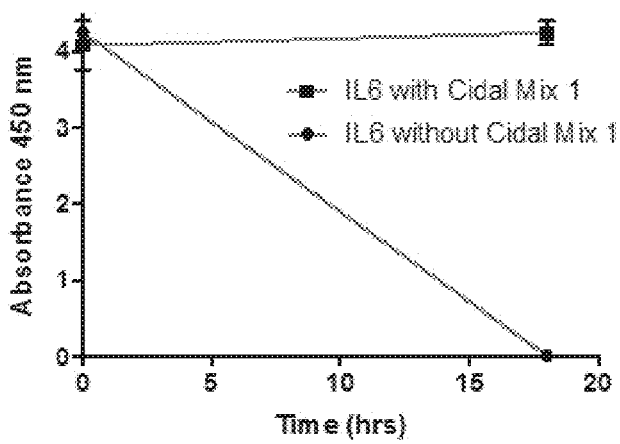
FIG. 45 shows ELISA data.
Figure 46:
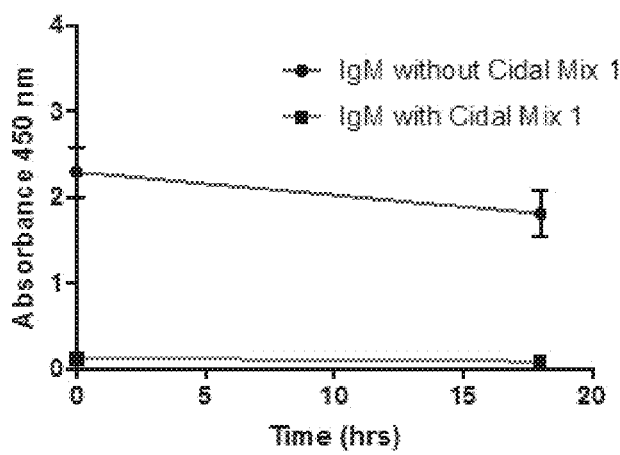
FIG. 46 shows ELISA data.
Figure 47:
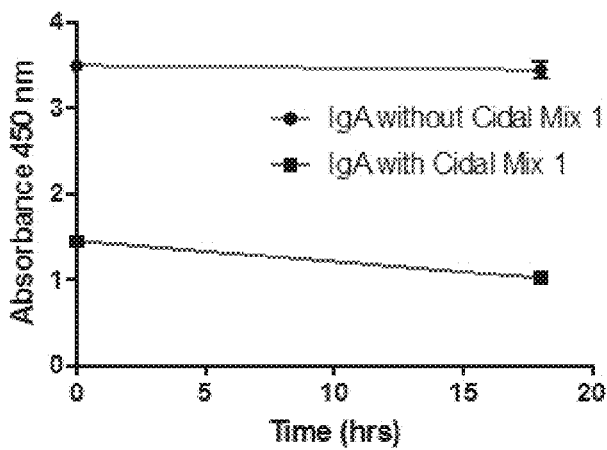
FIG. 47 shows ELISA data.

As shown in FIG. 45, using 0.3% Cidal Mix 1, 1×HALT and 1% BSA resulted in successful IL6 detection in SDJ. As shown in FIGS. 46 and 47, both IgA and IgM detection were inhibited by the presence of 0.3% Cidal Mix 1. Further investigation identified the sorbic acid and citric acid components in Cidal Mix 1 were responsible for the IgA and IgM ELISA assay inhibition.

Figure 48:
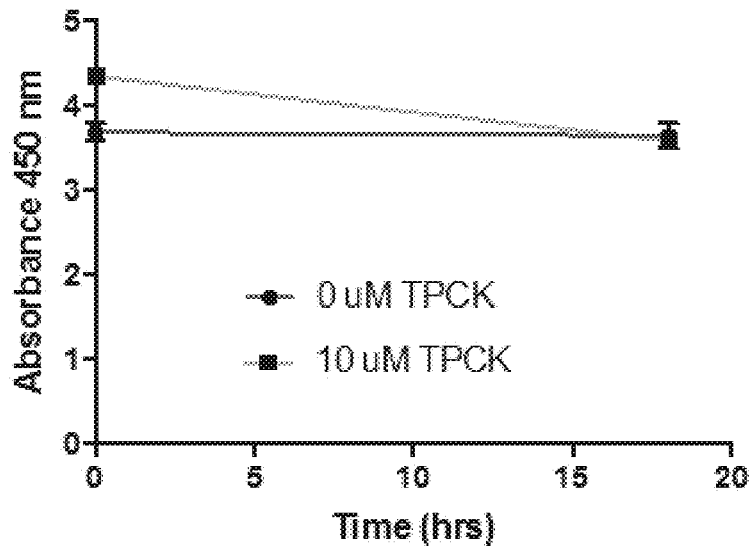
FIG. 48 shows ELISA data.
Figure 49:
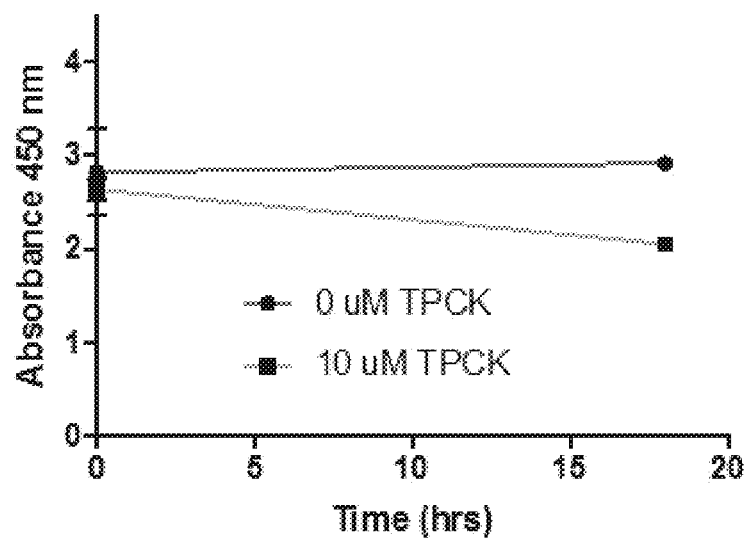
FIG. 49 shows ELISA data.
Figure 50:
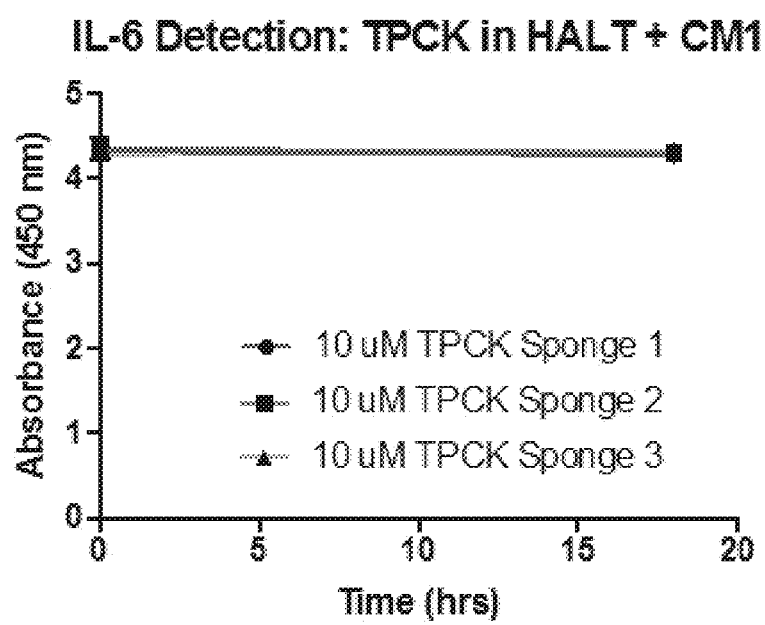
FIG. 50 shows ELISA data.

TPCK is a relatively stable and relatively irreversible inhibitor of serine proteases and was included in preservation mixes to provide additional protection against enzyme degradation. Studies were performed to determine the impact of TPCK's addition to the preservatives mixes. As shown in FIGS. 48-50, TPCK had no impact on the detection of IgA, IgM or IL-6, respectively.

Extraction of Protein Analytes in SDJ

Different extraction buffers and methods were tested to establish a protocol which yielded effective recovery of analytes from SDJ.

Figure 51:
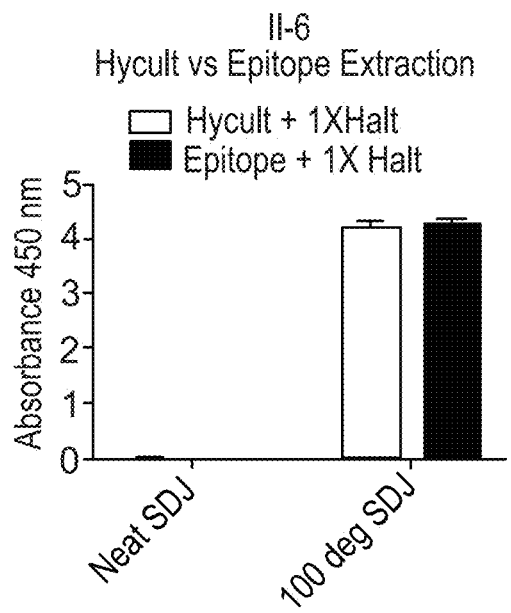
FIG. 51 shows ELISA data.
Figure 52:
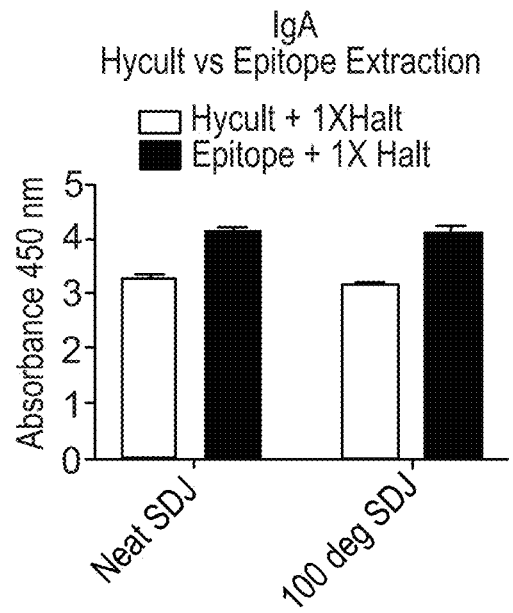
FIG. 52 shows ELISA data.
Figure 53:
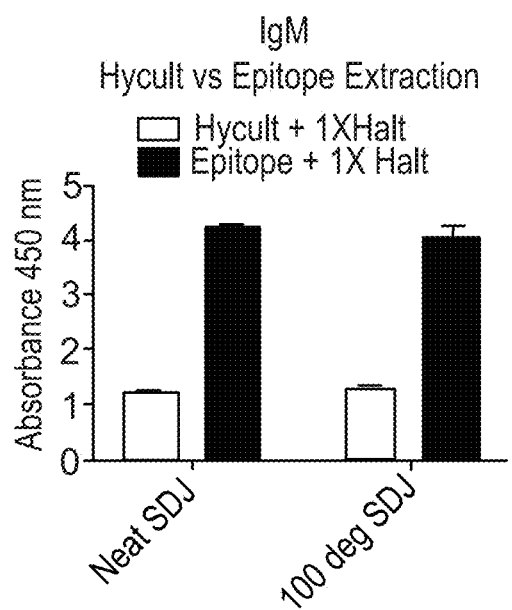
FIG. 53 shows ELISA data.
Figure 54:
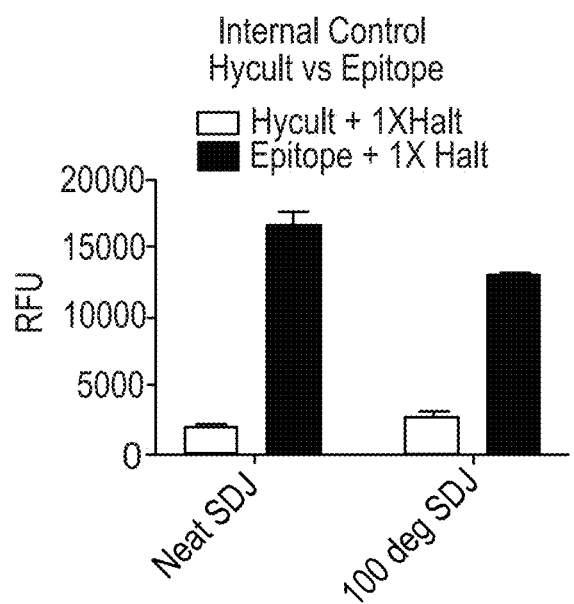
FIG. 54 shows ELISA data.

IgA protein was detected by ELISA following extraction using both HyCult and Epitope extraction buffers, with Epitope exhibiting superior results. IL6 signal was observed following extraction using both Epitope and Hycult extraction buffers. However, as shown in FIG. 51, IL6 was detected in heat treated SDJ. As shown in FIG. 52, IgA was detected in both neat SDJ and heat treated SDJ. Extraction of IgM from SDJ was effective with Epitope extraction buffer but not with Hycult extraction buffer. As shown in FIG. 53, IgM was detectable in both neat and heat treated SDJ following extraction with Epitope buffer. As shown in FIG. 54, IC was detectable in both neat and heat treated SDJ following extraction with Epitope buffer.

Evaluation of Sponge Materials

Figure 55:
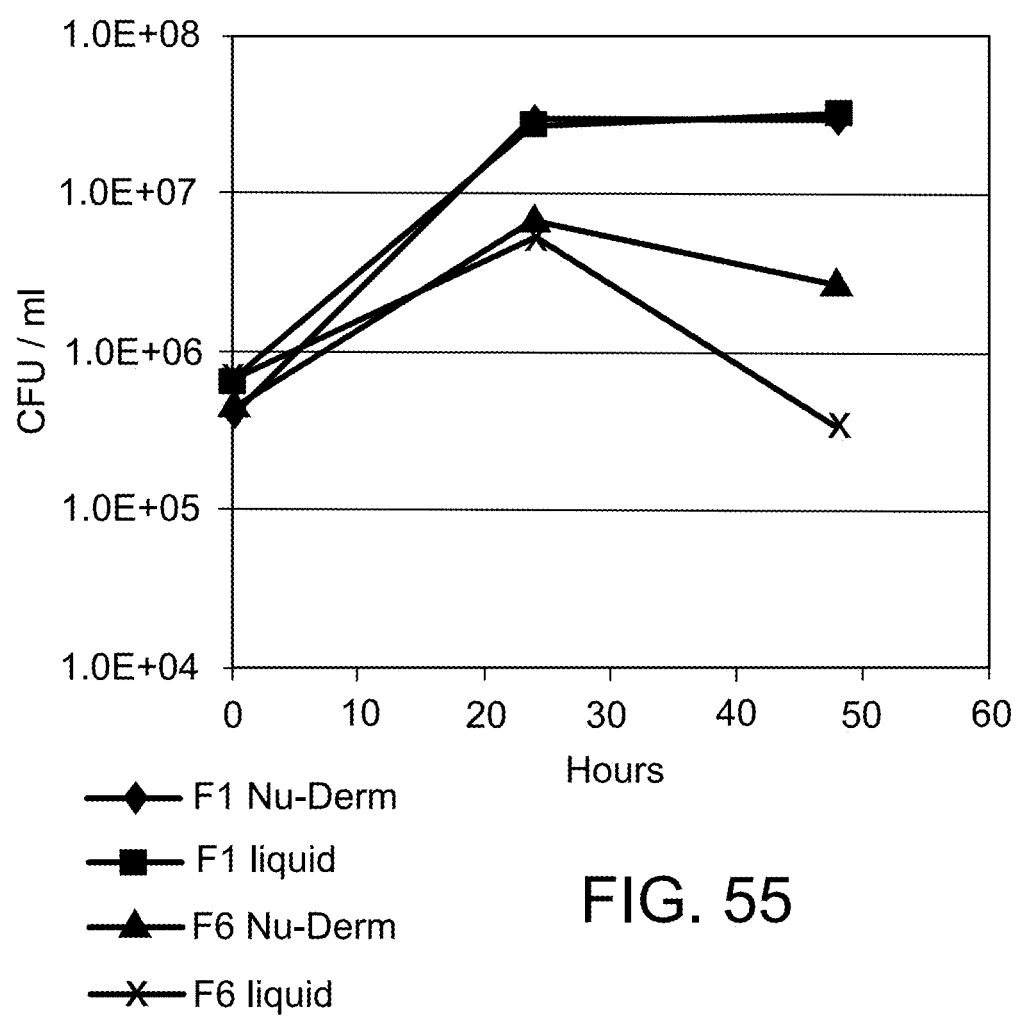
FIG. 55 shows data on bacteria amount as a function of time.

Sponges made of different absorbent materials were tested for their ability to retain bacteria over time, and to determine their suitability for use in an ingestible device. A sponge based on alginate, carboxymethyl cellulose, and collagene/cellulose was tested. In particular, the recovery of bacteria from sponges made from Promorgran™ (Systagenix), Aquacel™ (Convatec), Nu-DERM™ (Systagenix) was tested over time. Promorgran™ and Aquacel™ were rejected from consideration being because *Staphylococcus* and *Streptococcus* bacteria could not be recovered from these materials after they were seeded with bacteria. Nu-DERM™ was also rejected because gram positive strains could not be recovered after 24 hours of incubation, and gram negative strains were significantly reduced on this material over time. FIG. 55 shows the amounts of *Staphylococcus* (F1) and *Streptococcus* (F6) on Nu-Derm™ over time.

Figure 56A:
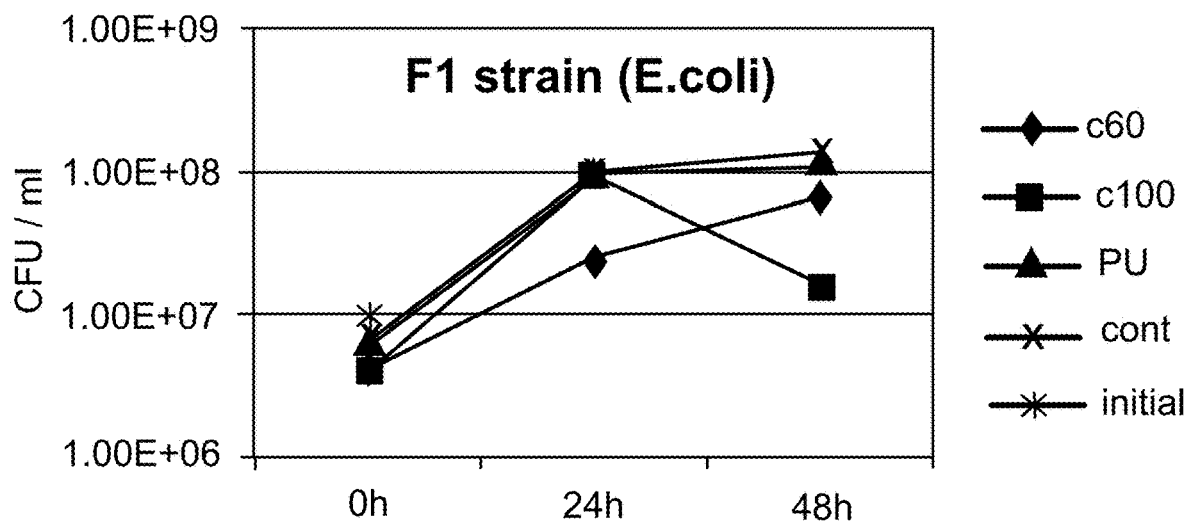
FIG. 56A-56C show bacteria recovery data.
Figure 56B:
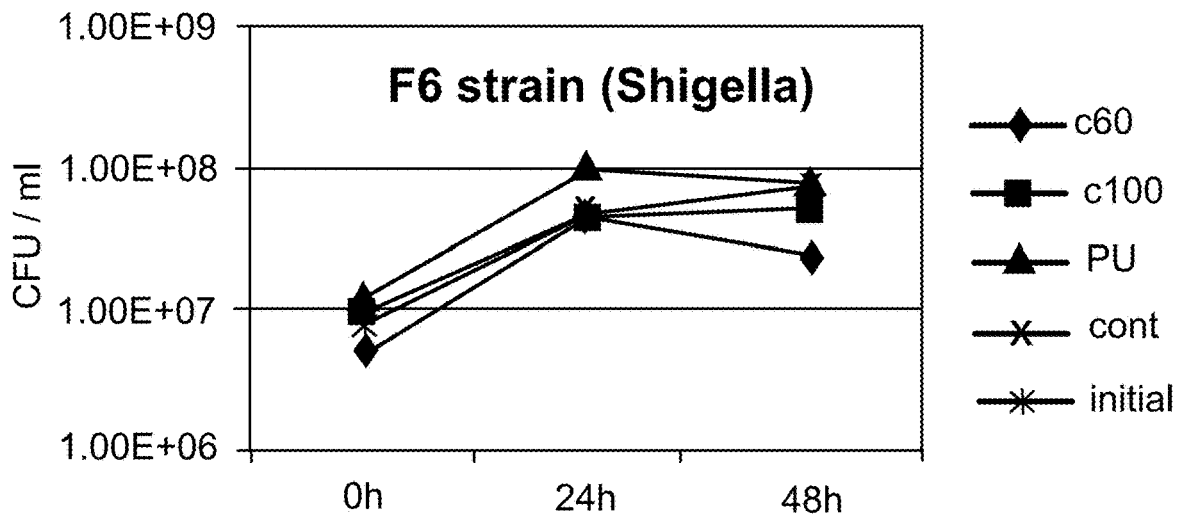
Figure 56C:
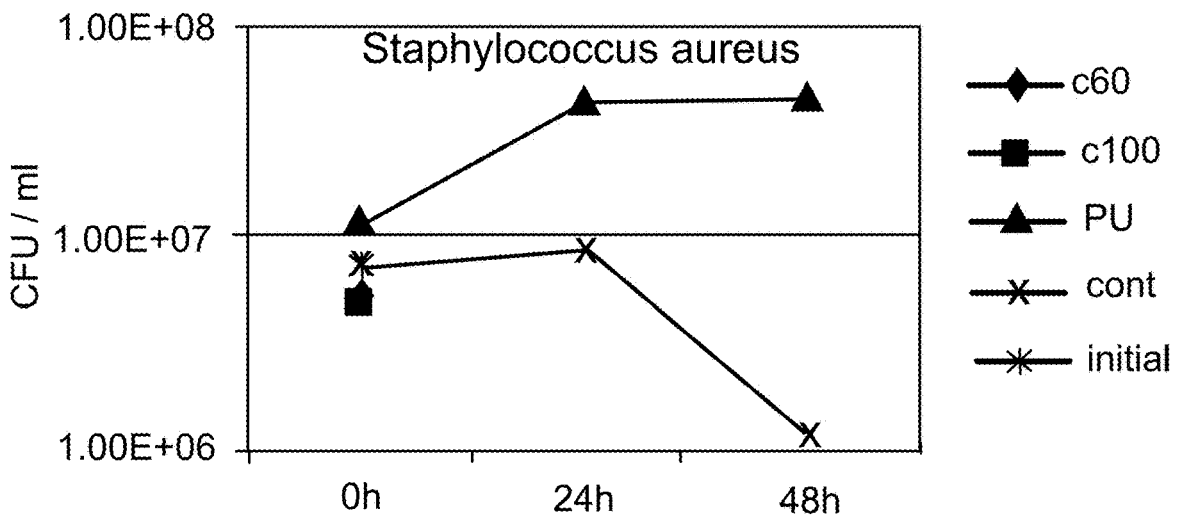

Non-degradable synthetic matrix sponges were also tested to determine if seeded bacteria could be recovered from them over time. Specifically, polyurethane (PU) and carbon sponges (C60 (60 ppi) and C100 (100 ppi)) were seeded with *E. coli* (F1), *Shigella* (F6), or *Staphylococcus aureus*, and the recovery of bacteria was then tested over the course of 48 hours. FIG. 56A-56C show that the polyurethane sponges allowed more effective recovery of all bacteria tested. Synthetic sponges made of polyurethane were also selected because they do not significantly change size upon hydration, and preservatives can be stably added to the sponge.

Figure 57:
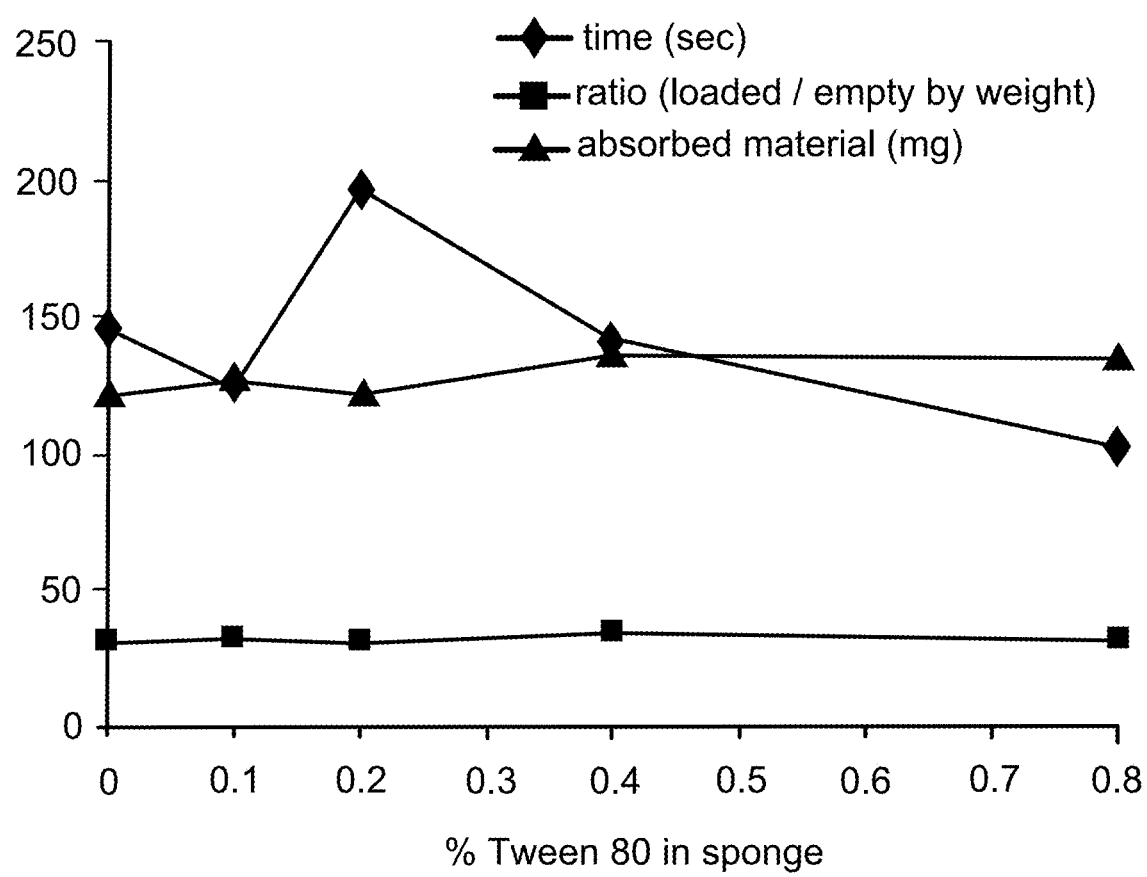
FIG. 57 shows data on fluid absorption.

The rate of saturation and final saturation weights for polyurethane sponges were then evaluated. Sponges were treated with Tween 80 and placed in a thin layer of porcine duodenal fluid, and then time to saturation and final weight were measured over time. FIG. 57 shows the absorption of duodenal fluid by tween 80 treated polyurethane sponges. Complete saturation of the absorbent material was reached within 3 minutes in all cases, and the weight of liquid absorbed is at least 30 times the weight of the sponge.

Chemical Stabilization of Bacterial Cells for Flow Cytometry

Figure 58:
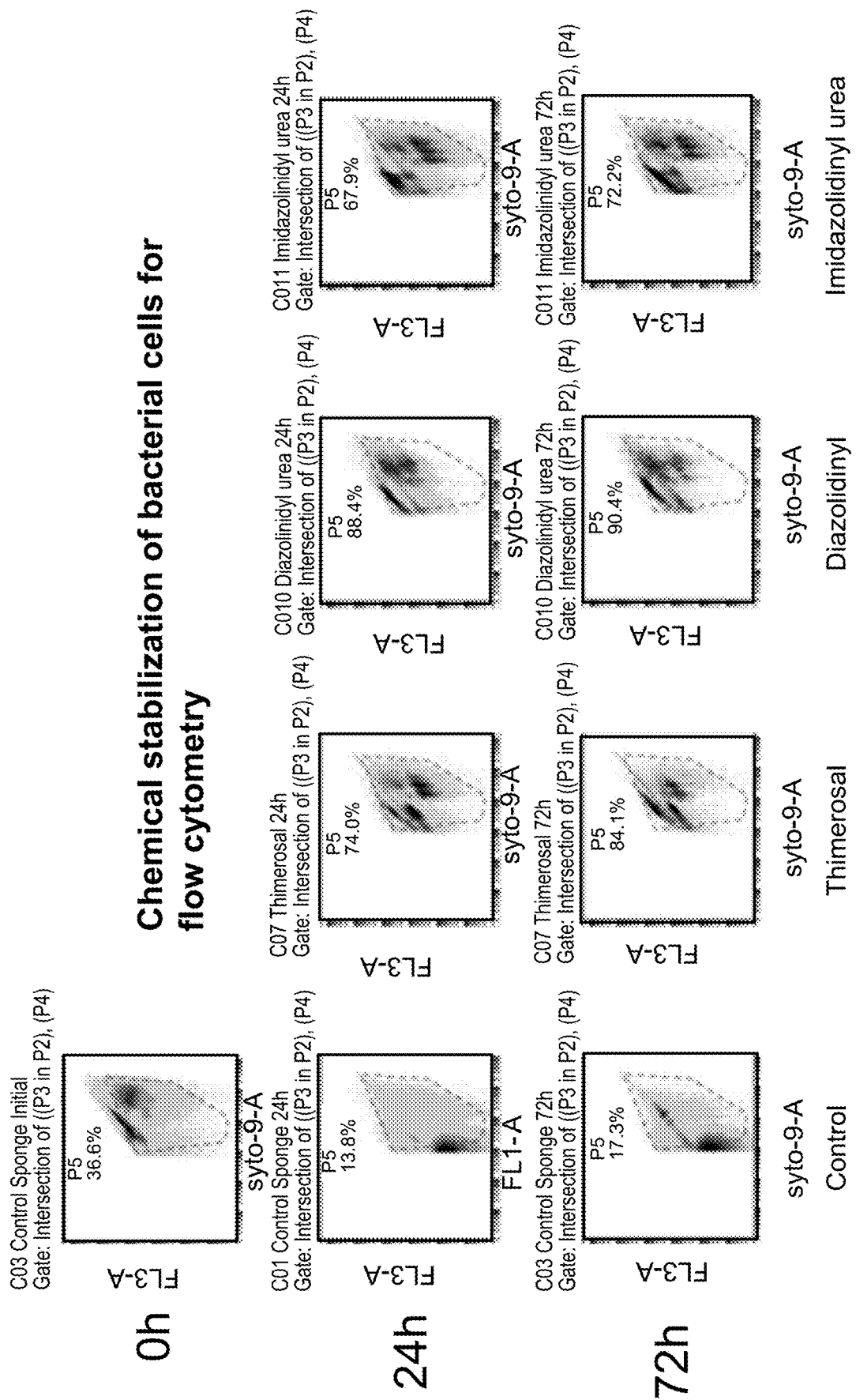
FIG. 58 shows data on inhibition/preservation of bacterial population.

Preservatives were tested on populations of bacteria to determine if they could stabilize bacterial cell counts over time. Bacteria cultures were seeded with thimerosal, diazolidinyl urea, or imidazolidinyl urea, and cell counts were measured over the course of 72 hours using flow cytometry. FIG. 58 shows that each of the preservatives can inhibit or preserve bacterial population growth for at least 72 hours. By contrast, control samples lacking preservative showed significant population growth over time.

Quantification of Stabilized Bacterial Samples by PCR and Flow Cytometry

To test the effectiveness of preservatives for stabilizing bacterial populations, multiple bacterial strains were seeded with a test preservative, and then bacteria were quantified over time using either PCR or FACS analysis. Test samples were prepared by inoculating strains of bacteria in culture, combining the strain cultures, and then diluting the combined cultures in simulated duodenal fluid. An absorbent material (polyurethane sponge) was then treated with a preservative, and the bacterial sample was then loaded onto the absorbent material containing the preservative, and incubated in a sealed tube at 37° C. for between 24 hours and up to 8 days. The sample was then recovered and bacterial cells were quantified. Porcine duodenal fluid and canine duodenal fluids were also tested using this assay. Porcine duodenal fluid and canine duodenal fluid were collected through laparotomy and biopsy of duodenal content.

Figure 59A:
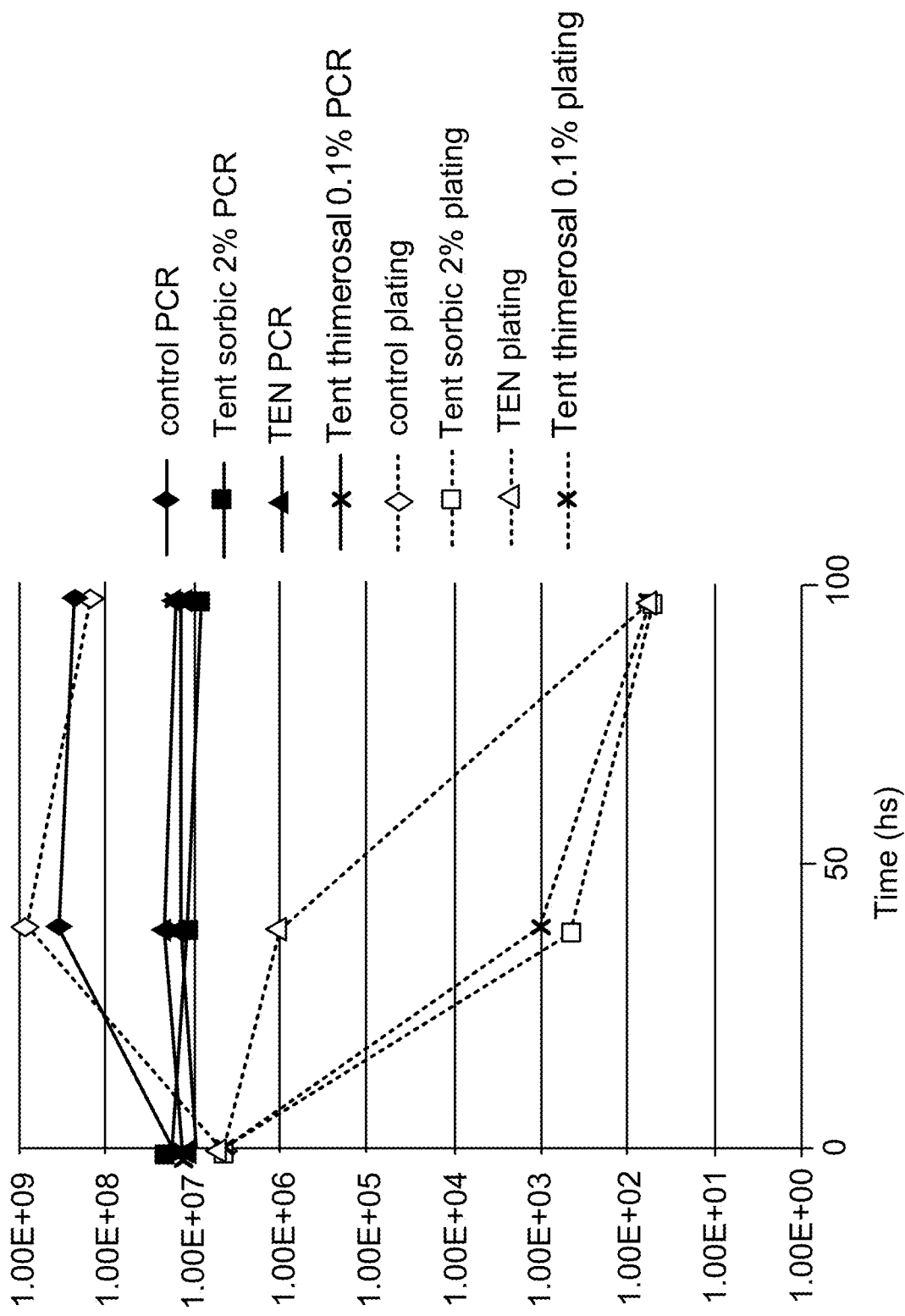
FIGS. 59A and 59B show data on reduction of viability of bacteria.
Figure 58:
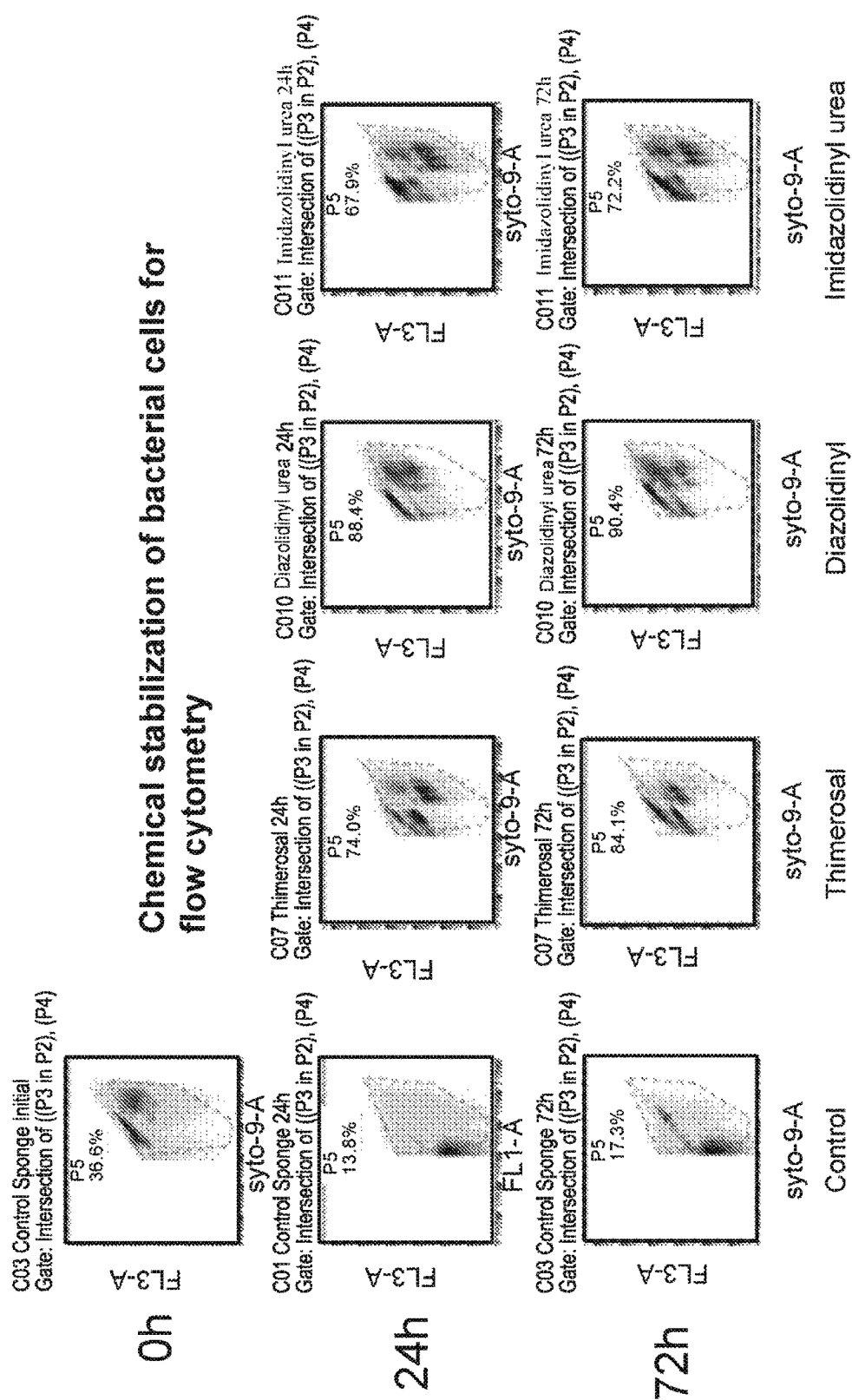
Figure 59A:
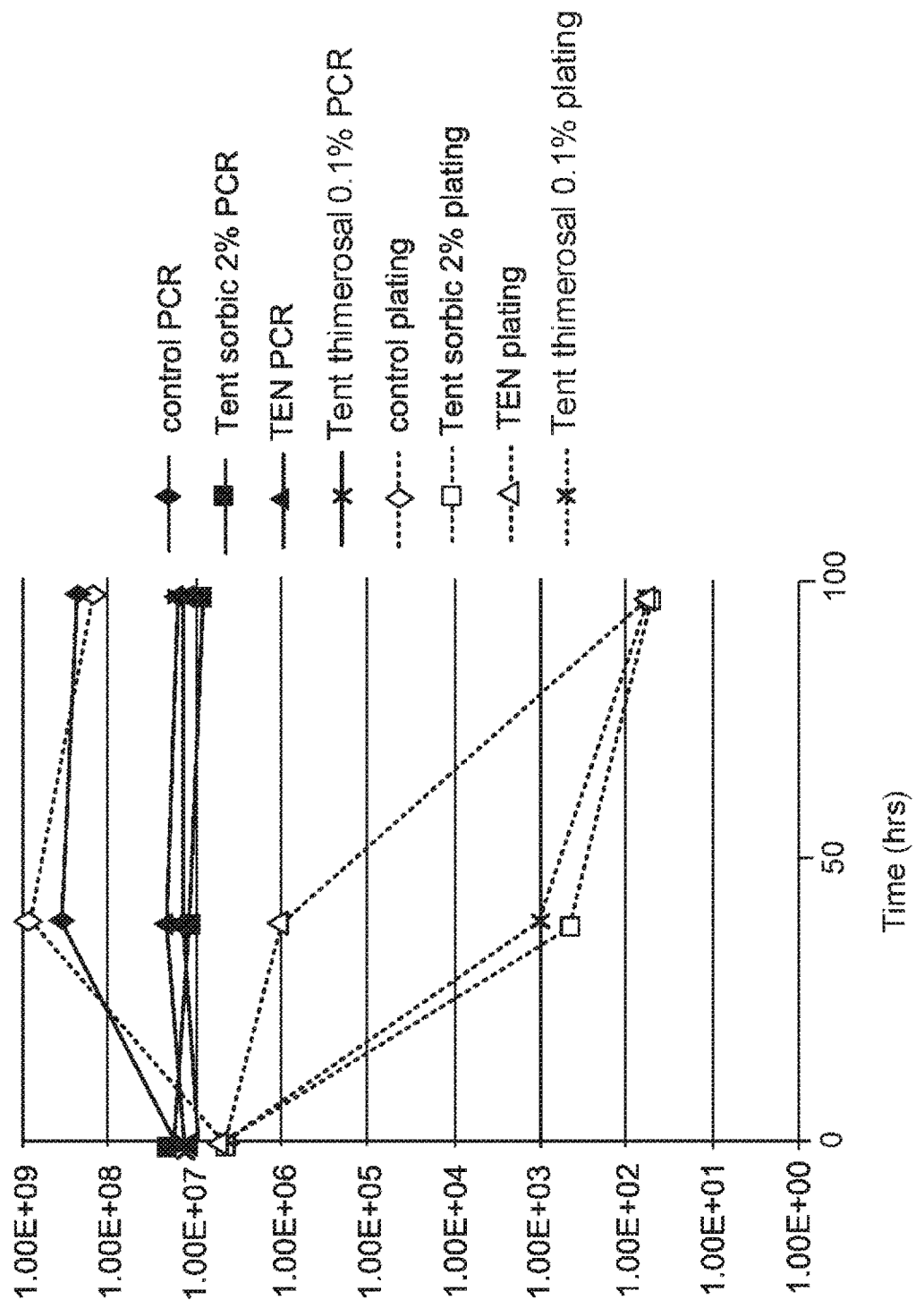
Figure 59B:
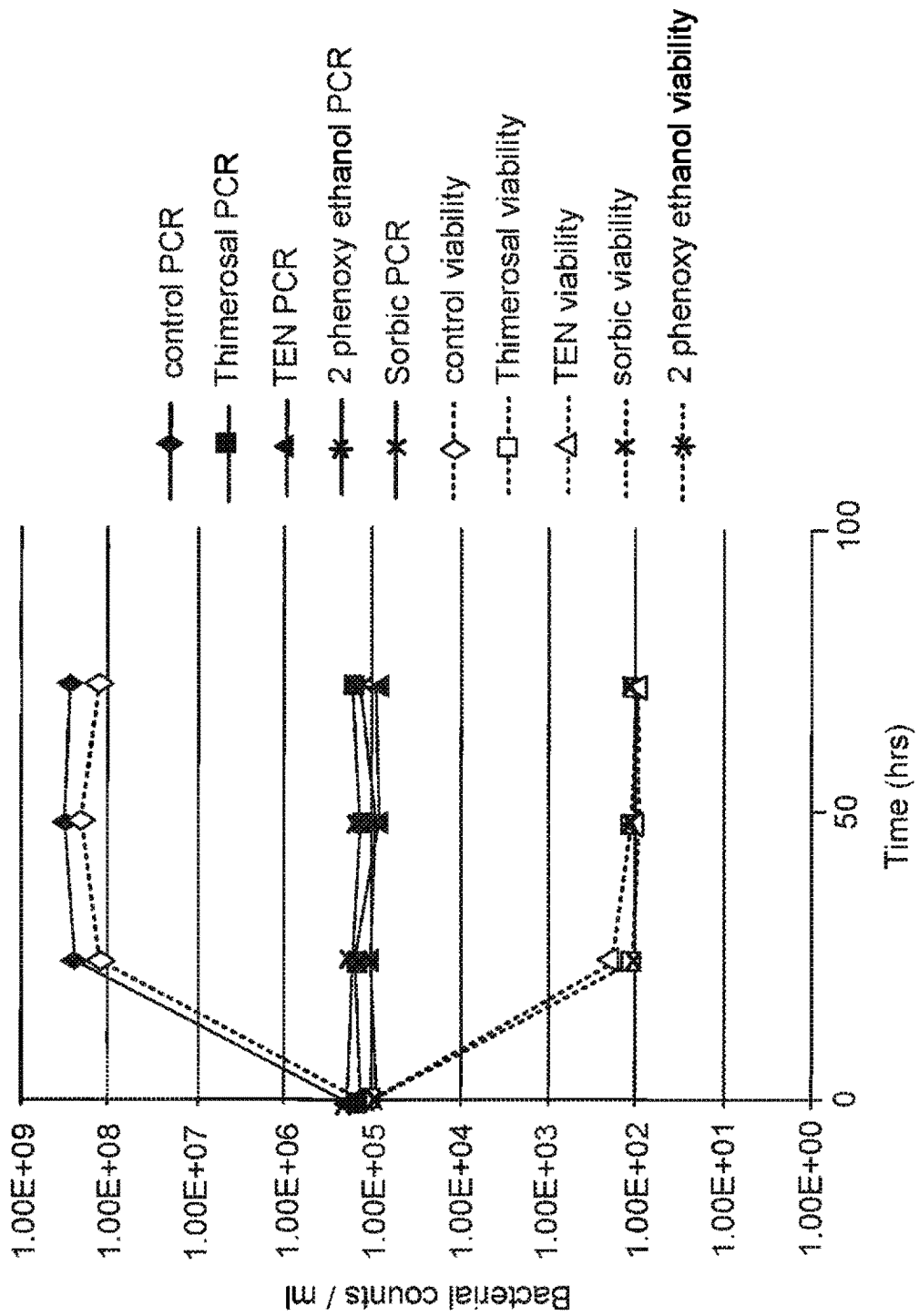

Bactericidal preservatives were added to cultures containing bacterial cells at $4.5 \times 10^6$ (high concentration) or at $8.6 \times 10^4$ (low concentration), and then cell counts were quantified using PCR or plating over time, and compared. The preservatives tested included TENT (Tris 50 mM, EDTA 50 mM, NaCl 1%, and Tween 80 2.5%), with sorbic acid, thimerosal, or 2-phenoxyethanol. FIGS. 59A and 59B show that the bactericidal preservatives reduce the viability of bacteria in both the high concentration and low concentration cultures.

Figure 60:
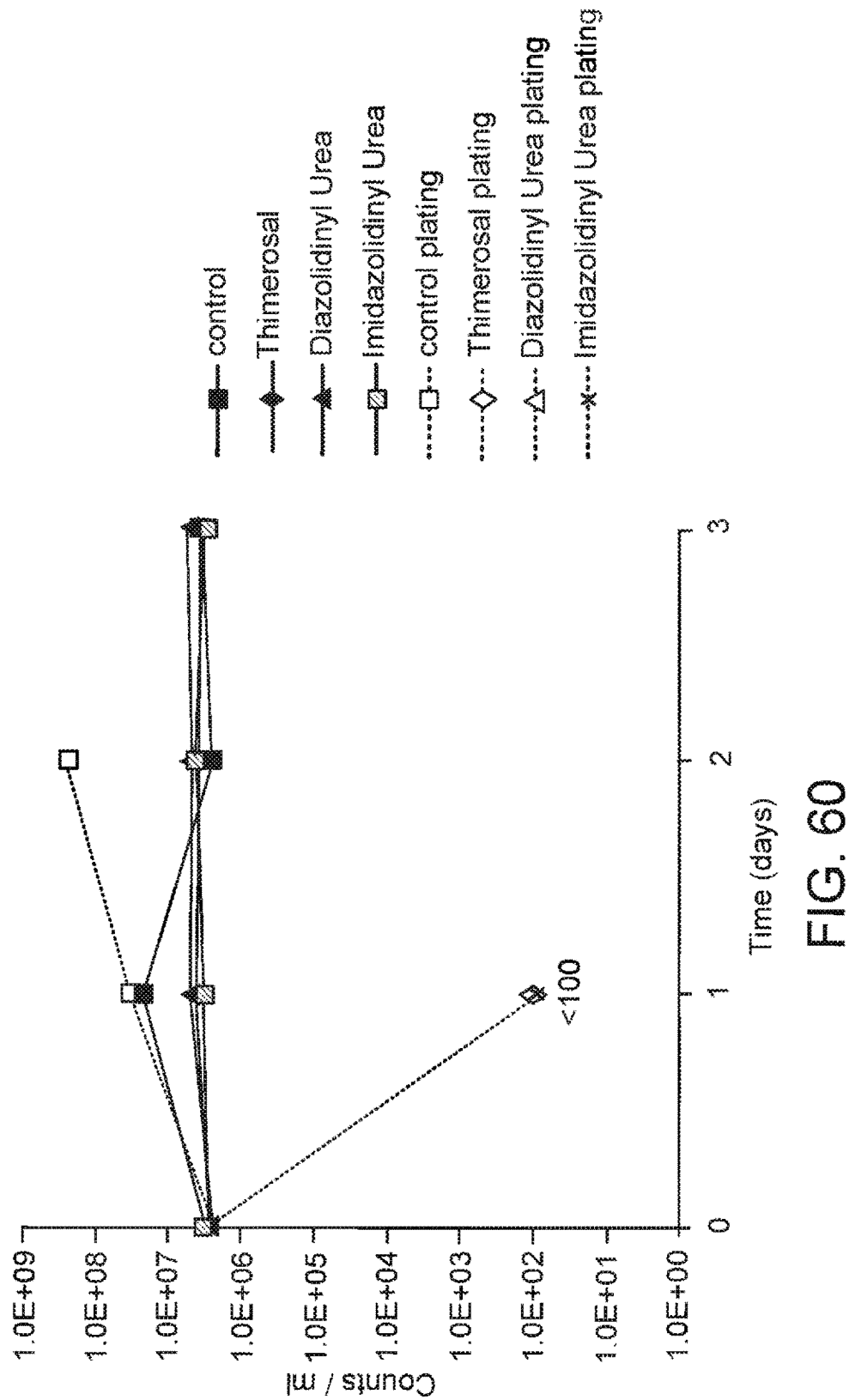
FIG. 60 shows data on reduction of viability of bacteria.

Bactericidal preservatives also significantly reduced viability of bacteria when measured by flow cytometry. Thimerosol, diazolidinyl urea, or imidazolinidyl urea were added to bacteria, and then cell counts were assessed over 3 days using with flow cytometry or cell plating. FIG. 60 shows that the bactericidal preservatives reduced the viability of bacteria over time.

In both the PCR and flow cytometry assays, the cell counts of the bacteria in the presence of bactericidal preservatives corresponded to the initial bacterial counts as assessed by plating (at time 0).

Other Embodiments

For illustrative purposes, the examples provided by above focus primarily on a number of different exemplary embodiments of an ingestible device. However, it is understood that variations in the general shape and design of one or more embodiments of the ingestible devices described herein (e.g., relation to the figures of devices) may be made without significantly changing the functions and operations of the device. Furthermore, it should be noted that the features and limitations described in any one embodiment may be applied to any other embodiment herein, and the descriptions and examples relating to one embodiment may be combined with any other embodiment in a suitable manner. For example, any of the valves described in relation to FIG. 7 may be used as the valves 214 and 216 described in relation to FIG. 2. As an alternate example, the absorptive material 310 and flexible membrane 314 described in relation to FIG. 3 may be incorporated into any of the various sampling chambers described in various embodiments of ingestible devices 100, 200, 600, and 702-706 in order to automatically seal the sampling chamber. Moreover, the figures and examples provided in disclosure are intended to be only exemplary, and not limiting. It should also be noted that the systems and/or methods described above may be applied to, or used in accordance with, other systems and/or methods, including systems and/or methods that may or may not be directly related to ingestible devices.

For illustrative purposes the disclosure focuses primarily on a number of different example embodiments of an ingestible device, and example embodiments of methods for obtaining a sample when the ingestible device within a GI tract. However, the possible ingestible devices that may be constructed are not limited to these embodiments, and variations in the shape and design may be made without significantly changing the functions and operations of the device.

At least some of the elements of the various embodiments of the ingestible device described herein that are implemented via software (e.g., software executed by control circuitry within PCB 120 (FIG. 2)) may be written in a high-level procedural language such as object oriented programming, a scripting language or both. Accordingly, the program code may be written in C, $C^{++}$ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software that to implement the functionality of at least one of the embodiments described herein. The program code, when read by the computing device, configures the computing device to operate in a new, specific and pre-defined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

What is claimed is:

1. An ingestible device, comprising:
   a sampling system, comprising:
      a first absorbent member;
      a second absorbent member different from the first absorbent member; and
      at least one preservative,
   wherein:
      the first absorbent member is configured to absorb a fluid,
      the sampling system is configured so that fluid that flows from an exterior of the ingestible device to an interior of the ingestible device enters the first absorbent member; and
      the sampling system is configured to allow fluid to flow from the first absorbent member to the second absorbent member.

2. The ingestible device of claim 1, wherein the at least one preservative is at least one analyte preservative.

3. The ingestible device of claim 2, wherein the at least one analyte preservative comprises a preservative for at least one of a nucleic acid, a small molecule, or a protein.

4. The ingestible device of claim 2, wherein the at least one analyte preservative comprises a preservative for at least one nucleic acid, small molecule, or protein that is a biomarker of at least one GI disorder.

5. The ingestible device of claim 2, wherein the at least one analyte preservative is a surfactant.

6. The ingestible device of claim 2, wherein the at least one analyte preservative is a stabilizer.

7. The ingestible device of claim 2, wherein the at least one analyte preservative comprises a member selected from the group consisting of a nuclease inhibitor, an RNase inhibitor, and a protease inhibitor.

8. The ingestible device of claim 2, wherein the at least one analyte preservative comprises an acid having a pKa of from three to seven.

9. The ingestible device of claim 2, wherein the at least one analyte preservative comprises a paraben.

10. The ingestible device of claim 5, wherein the surfactant comprises polysorbate.

11. The ingestible device of claim 6, wherein the stabilizer comprises trehalose or dextran.

12. The ingestible device of claim 9, wherein the paraben comprises a member selected from the group consisting of parahydroxybenzoate, an ester of parahydroxybenzoic acid, and propyl paraben.

13. The ingestible device of claim 7, wherein the at least one analyte preservative comprises a protease inhibitor.

14. The ingestible device of claim 13, wherein the protease inhibitor comprises a member selected from the group consisting of serine protease inhibitors, metalloprotease inhibitors, aminopeptidase inhibitors, cysteine peptidase inhibitor, and aspartyl protease inhibitors.

15. The ingestible device of claim 2, wherein the at least one analyte preservative comprises an acid.

16. The ingestible device of claim 2, wherein the at least one analyte preservative comprises at least one member selected from the group consisting of sorbic acid and citric acid.

17. The ingestible device of claim 1, wherein the at least one preservative comprises at least one bacteria preservative.

18. The ingestible device of claim 17, wherein the at least one bacteria preservative reduces bacterial growth and multiplication.

19. The ingestible device of claim 17, wherein the at least one bacteria preservative comprises a bactericidal or bacteriostatic preservative.

20. The ingestible device of claim 17, wherein the at least one bacteria preservative comprises a preservative for at least one bacterium associated with at least one GI disorder.

21. The ingestible device of claim 17, wherein the at least one bacteria preservative comprises a member selected from the group consisting of sorbic acid, citric acid, propyl paraben, nisin, dimethyl dicarbonate, ethylenediaminetetraacetic acid (EDTA), sodium azide, hydroxyurea, fusidic acid, diazolidinyl urea, imidazolidinyl urea, salicylic acid, barium and nickle chloride, metallic copper, thimerosal, 2-phenoxyethanol, and ProClin.

22. The ingestible device of claim 17, wherein the at least one bacteria preservative is sorbic acid, thimerosal, 2-phenoxyethanol, diazolinidyl urea, or imidazolinidyl urea.

23. The ingestible device of claim 2, wherein the at least one absorbent member comprises at least one analyte preservative in addition to the at least one bacteria preservative.

24. The ingestible device of claim 23, wherein the at least one analyte preservative is a nucleic acid preservative.

25. The ingestible device of claim 24, wherein the nucleic acid preservative is a DNAse inhibitor or an RNase inhibitor.

26. The ingestible device of claim 1, wherein the sampling system comprises a plurality of different preservatives.

27. The ingestible device of claim 1, wherein the sampling system further comprises a cell filter between the first and second absorbent members.

28. The ingestible device of claim 1, wherein the sampling system further comprises a cell filter.

29. The ingestible device of claim 1, wherein the fluid comprises a GI fluid.

30. The ingestible device of claim 1, wherein the sampling system is configured to fit within an ingestible device that does not include analytical instrumentation.

31. The ingestible device of claim 1, wherein the at least one preservative is at least partially absorbed in the second absorbent member.

32. A method, comprising:
   collecting a sample into the ingestible device of claim 1.

33. The method of claim 32, wherein the at least one preservative is at least partially absorbed in the second absorbent member.

* * * * *

UNITED STATES PATENT AND TRADEMARK OFFICE
CERTIFICATE OF CORRECTION

PATENT NO. : 10,588,608 B2
APPLICATION NO. : 15/680430
DATED : March 17, 2020
INVENTOR(S) : Mitchell Lawrence Jones et al.

It is certified that error appears in the above-identified patent and that said Letters Patent is hereby corrected as shown below:

On the Title Page

Page 2, Column 2 (Other Publications), Line 18, delete "-26," and insert -- -36, --;

In the Drawings

Replace Sheets 49, 50, 51 and 52 with attached Replacement Sheets;

In the Specification

Column 6, Line 41, delete "nickle" and insert -- nickel --;

Column 6, Line 44, delete "diazolinidyl" and insert -- diazolidinyl --;

Column 6, Line 45, delete "imidazolinidyl" and insert -- imidazolidinyl --;

Column 8, Line 38, delete "nickle" and insert -- nickel --;

Column 8, Line 41, delete "diazolinidyl" and insert -- diazolidinyl --;

Column 8, Line 42, delete "imidazolinidyl" and insert -- imidazolidinyl --;

Column 15, Line 12, delete "third third" and insert -- third --;

Column 15, Line 56, delete "FIG." and insert -- FIGS. --;

Column 36, Line 61, after "magnets" insert -- . --;

Column 36, Line 66, delete "counterclockwise" and insert -- counter-clockwise --;

Signed and Sealed this
Second Day of June, 2020

Andrei Iancu
*Director of the United States Patent and Trademark Office*

CERTIFICATE OF CORRECTION (continued)
U.S. Pat. No. 10,588,608 B2

Column 40, Line 59, delete "regio-specific" and insert -- regiospecific --;

Column 46, Line 31, delete "granulomatomas," and insert -- granulomatosis, --;

Column 47, Line 54, delete "dH20." and insert -- dH$_2$O. --;

Column 47, Line 56, delete "(ThermoFisher" and insert -- (Thermo Fisher --;

Column 48, Line 50, delete "CCL8, CCL9/CCL10, CCL11," and insert -- CCL8, CCL9, CCL10, CCL11, --;

Column 48, Line 37, delete "CCL8, CCL9/CCL10, CCL11," and insert -- CCL8, CCL9, CCL10, CCL11, --;

Column 49, Line 56, delete "extodysplasin" and insert -- ectodysplasin --;

Column 49, Line 64, delete "extodysplasin" and insert -- ectodysplasin --;

Column 50, Line 42, delete "anto-endomysial" and insert -- anti-endomysial --;

Column 50, Line 44, delete "herepeiformis." and insert -- herpetiformis. --;

Column 50, Line 54, delete "certolizuman" and insert -- certolizumab --;

Column 50, Line 55, delete "entanercept," and insert -- etanercept, --;

Column 50, Line 65, delete "certolizuman" and insert -- certolizumab --;

Column 50, Line 66, delete "entanercept," and insert -- etanercept, --;

Column 52, Line 6, delete "elasetase)." and insert -- elastase). --;

Column 53, Line 66, delete "femocene," and insert -- ferrocene, --;

Column 56, Line 9, delete "bacteriocidal," and insert -- bactericidal, --;

Column 56, Line 28, delete "nickle" and insert -- nickel --;

Column 56, Line 34, delete "nickle" and insert -- nickel --;

Column 59, Line 1, delete "30.00" and insert -- 30,000 --;

Column 60, Line 13, delete "investigatged" and insert -- investigated --;

Column 62, Line 24, delete "collagene/" and insert -- collagen/ --;

CERTIFICATE OF CORRECTION (continued)
U.S. Pat. No. 10,588,608 B2

Column 62, Line 26, delete "Promorgran™" and insert -- Promogran™ --;

Column 62, Line 28, delete "Promorgran™" and insert -- Promogran™ --;

Column 63, Line 32, delete "Thimerosol," and insert -- Thimerosal, --;

Column 63, Line 32, delete "imidazolinidyl" and insert -- imidazolidinyl --;

In the Claims

Column 65, Line 27, Claim 1, delete "fluid," and insert -- fluid; --;

Column 66, Line 32, Claim 21, delete "nickle" and insert -- nickel --;

Column 66, Line 36, Claim 22, delete "diazolinidyl" and insert -- diazolidinyl --;

Column 66, Line 36, Claim 22, delete "imidazolinidyl" and insert -- imidazolidinyl --.